(12) United States Patent
Black

(10) Patent No.: US 12,408,916 B2
(45) Date of Patent: Sep. 9, 2025

(54) SYSTEM AND METHOD FOR PERFORMING TISSUE TREATMENT USING POWERED TREATMENT DEVICES

(71) Applicant: Ashley Diana Black International Holdings, LLC, Pearland, TX (US)

(72) Inventor: Ashley D. Black, Pearland, TX (US)

(73) Assignee: Ashley Diana Black International Holdings, LLC, Pearland, TX (US)

( * ) Notice: Subject to any disclaimer, the term of this patent is extended or adjusted under 35 U.S.C. 154(b) by 181 days.

(21) Appl. No.: 18/076,308

(22) Filed: Dec. 6, 2022

(65) Prior Publication Data

US 2023/0200811 A1 Jun. 29, 2023

Related U.S. Application Data

(63) Continuation-in-part of application No. 17/545,920, filed on Dec. 8, 2021.
(Continued)

(51) Int. Cl.
*A61B 17/072* (2006.01)
*A61H 23/02* (2006.01)
(Continued)

(52) U.S. Cl.
CPC ....... *A61B 17/072* (2013.01); *A61H 23/0254* (2013.01); *A61N 5/0616* (2013.01);
(Continued)

(58) Field of Classification Search
CPC ..... A61B 17/068; A61B 17/072; A61B 90/00; A61B 2018/00708; A61H 7/00;
(Continued)

(56) References Cited

U.S. PATENT DOCUMENTS

| D21,551 S | 5/1892 | Young |
| 687,363 A | 11/1901 | Wirt |

(Continued)

FOREIGN PATENT DOCUMENTS

| AU | 655910 B3 | 1/1995 |
| CN | 2438449 Y | 7/2001 |

(Continued)

OTHER PUBLICATIONS

Amazon, "Mini Paddle Blaster", Date First Available: Oct. 27, 2020. https://www.amazon.com/Mini-Paddle Blaster-Cellulite-FasciaBlaster/dp/B08LZR7GWW/ref=cm_cr_arp_d_project_top?ie=UTF8 (Year: 2020).

(Continued)

*Primary Examiner* — Scott A Smith
(74) *Attorney, Agent, or Firm* — Foley & Lardner LLP

(57) ABSTRACT

A powered treatment device for restructuring and revitalizing fascia tissue. The powered treatment device may include a housing, an actuator, and a tissue treatment assembly. The actuator may be configured to rotate and may be coupled to and disposed substantially within the housing. The tissue treatment assembly may include a panel and a plurality of finger members. The plurality of finger member may be fixedly coupled to the panel at a proximal end of the respective finger members. The finger members may be rigid and extend away from the panel. Each one of the finger members may have a respective central axis that extends from the proximal end to a distal end of the respective finger member. At least one of the central axes may extend at least partly along a radial direction and/or a circumferential direction of the panel.

28 Claims, 84 Drawing Sheets

Related U.S. Application Data

(60) Provisional application No. 63/347,961, filed on Jun. 1, 2022, provisional application No. 63/286,536, filed on Dec. 6, 2021.

(51) Int. Cl.
*A61N 5/06* (2006.01)
*A61B 17/00* (2006.01)
*A61B 17/068* (2006.01)

(52) U.S. Cl.
CPC ..... *A61B 2017/0046* (2013.01); *A61B 17/068* (2013.01); *A61B 2017/07271* (2013.01); *A61H 2201/0157* (2013.01); *A61H 2201/5061* (2013.01); *A61N 2005/0644* (2013.01); *A61N 2005/0652* (2013.01)

(58) Field of Classification Search
CPC .... A61H 7/005; A61H 7/007; A61H 15/0078; A61H 15/02; A61H 23/00; A61H 23/02; A61H 23/04; A61H 2201/0157; A61H 2201/169; A61H 2201/5061; A61H 2201/5071; A61H 23/0254; A61N 2005/0644; A61N 2005/065; A61N 2005/0652; A61N 5/0616
USPC ......... 227/19, 175.1; 601/93, 113, 129, 136, 601/18, 46, 72, 84
See application file for complete search history.

(56) References Cited

U.S. PATENT DOCUMENTS

| | | |
|---|---|---|
| 912,016 A | 2/1909 | Miller |
| 965,564 A | 7/1910 | Coates |
| 1,002,509 A * | 9/1911 | Fitz .......................... A61J 19/00 4/258 |
| 1,018,939 A | 2/1912 | Sterrick |
| D55,452 S | 6/1920 | Chase |
| 1,523,979 A | 1/1925 | Ryan |
| 1,713,756 A | 5/1929 | Hassler |
| 2,168,975 A | 8/1939 | Dumont |
| D140,384 S | 2/1945 | Latshaw |
| 2,468,327 A | 4/1949 | Hartung |
| 2,480,023 A * | 8/1949 | Holden .................. A61H 7/002 15/159.1 |
| 2,972,347 A | 2/1961 | McNair |
| D197,889 S | 4/1964 | Hass |
| D208,894 S | 10/1967 | Wedermeyer |
| D213,690 S | 4/1969 | Eckstrom |
| D233,632 S | 11/1974 | Kirk |
| 3,856,002 A | 12/1974 | Matsumoto |
| 3,862,662 A | 1/1975 | Kern |
| D234,724 S | 4/1975 | Tavel |
| 3,906,940 A * | 9/1975 | Kawada .................. A61H 9/005 604/315 |
| 4,023,567 A | 5/1977 | Wessel |
| 4,091,805 A | 5/1978 | Clark |
| 4,173,217 A | 11/1979 | Johnston |
| D260,928 S | 9/1981 | Gueret |
| 4,345,757 A | 8/1982 | Lo Voi |
| D269,375 S | 6/1983 | Masuda |
| D270,279 S | 8/1983 | Hamilton |
| D272,090 S | 1/1984 | Hosid |
| 4,454,867 A | 6/1984 | Swanson |
| 4,493,315 A | 1/1985 | Iwahashi |
| D279,126 S | 6/1985 | Kaeser |
| D280,434 S | 9/1985 | McManaway |
| D280,664 S | 9/1985 | Ishida |
| D281,815 S | 12/1985 | Conn et al. |
| D282,007 S | 12/1985 | McKinney |
| D300,853 S | 4/1989 | Smal |
| D315,408 S | 3/1991 | Duk |
| D319,645 S | 9/1991 | Geib |
| 5,044,356 A | 9/1991 | Fishman et al. |
| 5,103,809 A | 4/1992 | DeLuca et al. |
| D331,466 S | 12/1992 | Doria |
| D333,351 S | 2/1993 | Tsou |
| D342,319 S | 12/1993 | Cheng |
| 5,285,774 A | 2/1994 | Stachurski |
| D345,054 S | 3/1994 | Spence |
| D346,866 S | 5/1994 | Lotuaco |
| D349,576 S | 8/1994 | Heiligenstein et al. |
| D349,771 S | 8/1994 | Heiligenstein et al. |
| D350,608 S | 9/1994 | Yu |
| D350,851 S | 9/1994 | Spence |
| D351,658 S | 10/1994 | Beckman |
| 5,352,188 A | 10/1994 | Vitko |
| D359,358 S | 6/1995 | Pecora et al. |
| 5,445,596 A | 8/1995 | Grace |
| 5,483,719 A | 1/1996 | Ikemoto et al. |
| D369,447 S * | 4/1996 | Mann ............................ D32/19 |
| D373,197 S | 8/1996 | Schepper |
| D374,084 S | 9/1996 | Chen |
| D376,853 S | 12/1996 | Hsia |
| 5,588,953 A | 12/1996 | Chang |
| 5,647,841 A | 7/1997 | Groenewold et al. |
| D384,157 S | 9/1997 | Kusnets et al. |
| 5,674,261 A | 10/1997 | Smith |
| D387,873 S | 12/1997 | Lee |
| D390,966 S | 2/1998 | Huang |
| D391,645 S | 3/1998 | Chien |
| D392,424 S | 3/1998 | Burys |
| 5,728,050 A | 3/1998 | Lin |
| 5,730,708 A | 3/1998 | Spratt |
| D396,296 S | 7/1998 | Breznik |
| D398,401 S | 9/1998 | Antoskow |
| 5,823,145 A | 10/1998 | Hingiss |
| D403,429 S | 12/1998 | Blanchard |
| D403,430 S | 12/1998 | Chien |
| D404,495 S | 1/1999 | Chien |
| D408,925 S | 4/1999 | Berry et al. |
| D419,681 S | 1/2000 | Chen |
| D422,084 S | 3/2000 | Mickelson |
| D422,086 S | 3/2000 | Chen |
| D422,365 S | 4/2000 | Chen |
| D427,318 S | 6/2000 | Chen |
| D428,997 S | 8/2000 | Berry et al. |
| D430,936 S | 9/2000 | Noble |
| 6,139,553 A | 10/2000 | Dotan |
| D435,110 S | 12/2000 | Chen |
| D435,295 S | 12/2000 | Yoo |
| 6,179,229 B1 | 1/2001 | Desmond |
| 6,190,339 B1 | 2/2001 | Imazaike et al. |
| D443,067 S | 5/2001 | Chen |
| 6,241,693 B1 | 6/2001 | Lambden |
| 6,241,696 B1 | 6/2001 | York |
| D444,883 S | 7/2001 | Chen |
| 6,267,738 B1 | 7/2001 | Louis |
| D447,809 S | 9/2001 | Gladieux et al. |
| D449,695 S | 10/2001 | Ponton et al. |
| D454,959 S | 3/2002 | Harris et al. |
| 6,357,075 B1 | 3/2002 | Kaizuka |
| D455,837 S | 4/2002 | Kim |
| 6,412,997 B2 | 7/2002 | Berke et al. |
| D466,612 S | 12/2002 | Harris et al. |
| D468,084 S | 1/2003 | Lin |
| D468,829 S | 1/2003 | Chen |
| D469,879 S | 2/2003 | Chen |
| 6,536,970 B2 | 3/2003 | Hauser et al. |
| D473,657 S | 4/2003 | Lewis-Jonsson |
| 6,543,954 B2 | 4/2003 | Owings |
| D477,414 S | 7/2003 | Chen |
| 6,588,964 B1 | 7/2003 | Au et al. |
| D479,607 S | 9/2003 | Chen |
| D480,148 S | 9/2003 | Chen |
| D484,608 S | 12/2003 | Tinsley |
| D486,236 S | 2/2004 | Nan |
| 6,758,826 B2 | 7/2004 | Luettgen et al. |
| D495,803 S | 9/2004 | Gough et al. |
| D499,810 S | 12/2004 | Chien |
| D504,954 S | 5/2005 | Park |
| D510,440 S | 10/2005 | Huang |

(56) References Cited

U.S. PATENT DOCUMENTS

| | | |
|---|---|---|
| 6,974,427 B1 | 12/2005 | Lapham |
| D515,219 S | 2/2006 | Nan |
| D515,702 S | 2/2006 | Nan |
| 7,003,849 B2 | 2/2006 | Cohen et al. |
| 7,037,016 B1 | 5/2006 | Nelson |
| D523,962 S | 6/2006 | Huang |
| D530,428 S | 10/2006 | Huang |
| D530,822 S | 10/2006 | Inubushi |
| D532,113 S | 11/2006 | Huang |
| 7,153,282 B1 | 12/2006 | Dudley |
| D537,892 S | 3/2007 | Moses |
| D538,435 S | 3/2007 | Wang et al. |
| 7,238,163 B1 | 7/2007 | Fried et al. |
| D548,849 S | 8/2007 | Huang |
| 7,291,101 B2 | 11/2007 | Deal |
| D556,913 S | 12/2007 | Laituri |
| D558,355 S | 12/2007 | Huang |
| D565,304 S | 4/2008 | Stewart |
| D582,049 S | 12/2008 | Ferber et al. |
| D590,510 S | 4/2009 | Johansen et al. |
| D599,061 S | 8/2009 | Smith |
| D600,357 S | 9/2009 | Chaput |
| D613,416 S | 4/2010 | Schupman |
| D626,240 S | 10/2010 | Copeland et al. |
| D627,897 S | 11/2010 | Yde et al. |
| D627,898 S | 11/2010 | Aulwes et al. |
| D630,761 S | 1/2011 | Marshall |
| D633,217 S | 2/2011 | Robertson et al. |
| D643,933 S | 8/2011 | Watabe |
| D648,860 S | 11/2011 | Donahue et al. |
| D650,488 S | 12/2011 | Donahue et al. |
| D652,525 S | 1/2012 | Caggiano et al. |
| D656,277 S | 3/2012 | Mckee |
| D664,298 S | 7/2012 | Grabes et al. |
| D672,925 S | 12/2012 | Hungerford |
| D673,285 S | 12/2012 | Rivero |
| 8,337,438 B2 | 12/2012 | Schupman |
| D673,687 S | 1/2013 | Zeng et al. |
| D674,107 S | 1/2013 | Prudent et al. |
| D674,905 S | 1/2013 | Lowsky |
| D674,911 S | 1/2013 | Caldwell |
| D676,975 S | 2/2013 | Bickford |
| D677,391 S | 3/2013 | Bickford |
| D678,540 S | 3/2013 | Bickford |
| 8,419,663 B2 | 4/2013 | Eitzen |
| D692,569 S | 10/2013 | Samurin |
| D694,415 S | 11/2013 | Viner et al. |
| D703,825 S | 4/2014 | Barrett |
| D704,852 S | 5/2014 | Yang |
| D708,755 S | 7/2014 | Kim |
| D712,053 S | 8/2014 | Matsushita |
| D712,058 S | 8/2014 | Huang |
| 8,808,208 B2 | 8/2014 | Mouatt |
| D716,467 S | 10/2014 | Kanbar et al. |
| D719,664 S | 12/2014 | Riftin et al. |
| D721,420 S | 1/2015 | Hawkins |
| D721,421 S | 1/2015 | Hawkins |
| D721,440 S | 1/2015 | Pursel et al. |
| 8,954,155 B2 * | 2/2015 | Campbell ............... A61N 7/00 607/90 |
| D723,709 S | 3/2015 | Topolovac et al. |
| D724,752 S | 3/2015 | Huang |
| D725,788 S | 3/2015 | Matsushita |
| D732,181 S | 6/2015 | Viner et al. |
| 9,050,240 B2 | 6/2015 | Howsam |
| D735,818 S | 8/2015 | Black |
| D739,546 S | 9/2015 | Cheung |
| 9,125,481 B2 | 9/2015 | Watanabe et al. |
| D742,534 S | 11/2015 | Bains |
| D744,663 S | 12/2015 | Holland |
| 9,237,981 B1 | 1/2016 | Clementes |
| D750,796 S | 3/2016 | Bains |
| D750,841 S | 3/2016 | Lewis |
| D752,237 S | 3/2016 | Cole et al. |
| D765,872 S | 9/2016 | Blaskovich et al. |
| D773,682 S | 12/2016 | Faussett |
| D776,824 S | 1/2017 | Black |
| D777,939 S | 1/2017 | Black |
| D785,193 S | 4/2017 | Cole et al. |
| D790,724 S | 6/2017 | Black |
| D805,211 S | 12/2017 | Wu |
| 9,931,003 B2 * | 4/2018 | Sueyoshi ............ B01F 33/5011 |
| D818,588 S | 5/2018 | Black |
| D818,600 S | 5/2018 | Black |
| D819,825 S | 6/2018 | Black |
| D819,826 S | 6/2018 | Black |
| D825,929 S | 8/2018 | Julemont |
| D829,445 S * | 10/2018 | Kern ............................. D4/127 |
| D830,568 S | 10/2018 | Black |
| D834,832 S | 12/2018 | Kim |
| D841,176 S | 2/2019 | Gaquiere et al. |
| D842,489 S | 3/2019 | Spewock et al. |
| D843,002 S | 3/2019 | Yarborough et al. |
| D844,163 S | 3/2019 | Du |
| D844,797 S | 4/2019 | Matsushita |
| D845,002 S | 4/2019 | Disanti |
| D845,499 S | 4/2019 | Wersland et al. |
| D845,500 S | 4/2019 | Wersland et al. |
| D849,260 S | 5/2019 | Wersland et al. |
| D849,261 S | 5/2019 | Wersland et al. |
| D849,263 S | 5/2019 | Soutelo Gomes |
| D850,640 S | 6/2019 | Wersland et al. |
| D850,641 S | 6/2019 | Black |
| 10,322,057 B2 | 6/2019 | Black |
| D853,576 S | 7/2019 | Ma |
| D855,197 S | 7/2019 | Park |
| 10,383,486 B2 | 8/2019 | Nichols |
| D858,786 S | 9/2019 | Luo et al. |
| D858,789 S | 9/2019 | Logan |
| D861,182 S | 9/2019 | Wersland et al. |
| D863,587 S | 10/2019 | Yee |
| D865,203 S | 10/2019 | Eschbach et al. |
| 10,426,692 B2 | 10/2019 | Jurna et al. |
| D868,277 S | 11/2019 | Yamazaki |
| D869,673 S | 12/2019 | Chen |
| D873,418 S | 1/2020 | Scott |
| D874,666 S | 2/2020 | Matsushita |
| D887,572 S | 6/2020 | Matsushita |
| D890,353 S | 7/2020 | Nazarian |
| D890,941 S | 7/2020 | Gaquiere et al. |
| D890,943 S | 7/2020 | Wersland et al. |
| D894,414 S | 8/2020 | Sherrill |
| D895,823 S | 9/2020 | Khubani et al. |
| D896,393 S | 9/2020 | Wersland et al. |
| 10,765,199 B2 * | 9/2020 | Kern ...................... A61H 7/003 |
| 10,772,473 B2 * | 9/2020 | Johnstone ................ A47K 7/04 |
| D901,032 S | 11/2020 | Gonglach |
| D903,140 S | 11/2020 | Andrejs |
| D905,262 S | 12/2020 | Khubani et al. |
| D907,792 S | 1/2021 | Marton et al. |
| D908,235 S | 1/2021 | Marton et al. |
| D918,404 S | 5/2021 | Wersland et al. |
| D918,405 S | 5/2021 | Wersland et al. |
| D925,128 S | 7/2021 | Yang et al. |
| D927,722 S | 8/2021 | Park |
| 11,110,029 B2 | 9/2021 | Xie et al. |
| D941,036 S | 1/2022 | Hinds |
| D945,076 S | 3/2022 | Zhang |
| D946,166 S | 3/2022 | Li |
| D949,362 S | 4/2022 | Zheng |
| D949,365 S | 4/2022 | Li |
| D949,366 S | 4/2022 | Li |
| D949,374 S | 4/2022 | Black |
| D949,380 S | 4/2022 | Khubani et al. |
| D949,395 S | 4/2022 | Lee et al. |
| D950,062 S | 4/2022 | Vuillemin et al. |
| D952,166 S | 5/2022 | Peluso et al. |
| D952,175 S | 5/2022 | Zou |
| D953,555 S | 5/2022 | Lee et al. |
| D954,285 S | 6/2022 | Lee et al. |
| D956,240 S | 6/2022 | Mcbrien et al. |
| D956,996 S | 7/2022 | Costa |
| D961,795 S | 8/2022 | Zhao et al. |
| D962,556 S * | 8/2022 | Wu ............................. D30/121 |

(56) References Cited

U.S. PATENT DOCUMENTS

| | | |
|---|---|---|
| D967,978 S | 10/2022 | Liu |
| D975,045 S | 1/2023 | Xu |
| D977,667 S | 2/2023 | Yang |
| D977,842 S | 2/2023 | Lee |
| D979,087 S | 2/2023 | Yang |
| D981,578 S | 3/2023 | Yee |
| D982,356 S | 4/2023 | Kliegman et al. |
| D984,977 S | 5/2023 | Sun |
| D985,147 S | 5/2023 | Zhu |
| D985,786 S | 5/2023 | Yin |
| D992,131 S | 7/2023 | Marton |
| D992,132 S | 7/2023 | Marton |
| D992,135 S | 7/2023 | Omari et al. |
| D993,437 S | 7/2023 | Klimov |
| D994,131 S | 8/2023 | Black |
| D994,132 S | 8/2023 | Zong |
| D994,140 S | 8/2023 | Yang |
| D995,808 S | 8/2023 | Yin |
| D996,065 S | 8/2023 | Lei et al. |
| D998,149 S | 9/2023 | Ghoniem |
| D998,160 S | 9/2023 | Shao |
| D1,003,313 S | 10/2023 | Lin |
| D1,004,114 S | 11/2023 | Black |
| D1,005,500 S | 11/2023 | Yoon et al. |
| D1,005,516 S | 11/2023 | Leng |
| D1,005,692 S | 11/2023 | Russo |
| D1,006,247 S | 11/2023 | Qiao |
| D1,021,989 S | 4/2024 | Tsushima et al. |
| D1,026,228 S | 5/2024 | Black |
| D1,038,434 S | 8/2024 | Krut |
| D1,061,915 S | 2/2025 | Black |
| 2002/0147418 A1 | 10/2002 | Huang |
| 2002/0151930 A1 | 10/2002 | Mills |
| 2002/0193715 A1 | 12/2002 | Slack |
| 2003/0158505 A1 | 8/2003 | Calvert |
| 2003/0212353 A1 | 11/2003 | Kahn |
| 2004/0024336 A1 | 2/2004 | Lin |
| 2004/0082449 A1 | 4/2004 | Brown, Jr. |
| 2004/0208683 A1 | 10/2004 | Shawan et al. |
| 2004/0260215 A1 | 12/2004 | Kim |
| 2005/0015030 A1 | 1/2005 | Bousfield et al. |
| 2005/0096572 A1 | 5/2005 | Hua |
| 2005/0101944 A1 | 5/2005 | Williams |
| 2005/0107724 A1 | 5/2005 | Dunmore |
| 2005/0137505 A1 | 6/2005 | Munday |
| 2005/0142093 A1* | 6/2005 | Skover .................. A61Q 19/08 601/84 |
| 2006/0135323 A1 | 6/2006 | Sjobakk et al. |
| 2006/0253054 A1 | 11/2006 | Wright |
| 2007/0173750 A1 | 7/2007 | Hudock |
| 2007/0179412 A1* | 8/2007 | Imboden ................ H02J 50/12 601/72 |
| 2008/0086066 A1 | 4/2008 | Munday |
| 2008/0119913 A1* | 5/2008 | Powell .................. A61N 5/0616 606/9 |
| 2008/0167590 A1 | 7/2008 | Jon et al. |
| 2008/0200849 A1 | 8/2008 | Hollington et al. |
| 2008/0255486 A1 | 10/2008 | Ludlow |
| 2009/0121059 A1 | 5/2009 | Rios Garcia |
| 2009/0204061 A1 | 8/2009 | Pomposelli et al. |
| 2009/0287195 A1 | 11/2009 | Altshuler et al. |
| 2010/0040432 A1 | 2/2010 | Totsu |
| 2010/0160841 A1 | 6/2010 | Wu |
| 2010/0191161 A1 | 7/2010 | Mouatt |
| 2010/0217164 A1 | 8/2010 | Meyer et al. |
| 2010/0274162 A1 | 10/2010 | Evans |
| 2010/0312158 A1 | 12/2010 | Lin |
| 2011/0054369 A1 | 3/2011 | Destefano |
| 2011/0077561 A1 | 3/2011 | Choly |
| 2011/0087140 A1 | 4/2011 | Lee |
| 2011/0144550 A1 | 6/2011 | Suttman |
| 2011/0154690 A1 | 6/2011 | Walsh |
| 2011/0224588 A1 | 9/2011 | Grippo |
| 2012/0016292 A1 | 1/2012 | Goldberg et al. |
| 2012/0109043 A1 | 5/2012 | Zhou et al. |
| 2012/0121313 A1 | 5/2012 | Thiebaut |
| 2012/0167323 A1 | 7/2012 | Williams |
| 2012/0204369 A1 | 8/2012 | Watanabe et al. |
| 2012/0323151 A1 | 12/2012 | Faussett |
| 2013/0023807 A1 | 1/2013 | Hennessey |
| 2013/0046212 A1* | 2/2013 | Nichols .................. A61N 1/00 601/18 |
| 2013/0079689 A1* | 3/2013 | Thierman ................ A61H 7/00 601/46 |
| 2013/0190664 A1 | 7/2013 | Johnson |
| 2013/0197405 A1 | 8/2013 | Williams et al. |
| 2013/0226052 A1 | 8/2013 | Niggemann |
| 2013/0324792 A1 | 12/2013 | Mizrahi et al. |
| 2014/0200495 A1 | 7/2014 | Jones |
| 2014/0243718 A1 | 8/2014 | Black |
| 2014/0272761 A1 | 9/2014 | Lowe et al. |
| 2014/0323993 A1 | 10/2014 | Wilcox et al. |
| 2014/0358045 A1 | 12/2014 | Toto |
| 2015/0135455 A1 | 5/2015 | Reusche et al. |
| 2015/0157414 A1 | 6/2015 | Van Curen |
| 2015/0216292 A1 | 8/2015 | Tweel et al. |
| 2016/0008213 A1 | 1/2016 | Cheng |
| 2016/0099595 A1 | 4/2016 | Chien |
| 2016/0175185 A1 | 6/2016 | Buchner Santos et al. |
| 2016/0206087 A1* | 7/2016 | Skidmore .......... A46B 15/0004 |
| 2017/0073050 A1* | 3/2017 | Smith ....................... B08B 1/36 |
| 2017/0216136 A1 | 8/2017 | Gordon |
| 2017/0333280 A1 | 11/2017 | Black |
| 2017/0348082 A1* | 12/2017 | Ogleby .................. A01K 13/00 |
| 2018/0161233 A1 | 6/2018 | Nakanishi |
| 2018/0288160 A1 | 10/2018 | Paul et al. |
| 2019/0045912 A1 | 2/2019 | Mikitovic et al. |
| 2019/0045918 A1 | 2/2019 | Przirembel et al. |
| 2019/0216678 A1 | 7/2019 | Yang |
| 2019/0247268 A1 | 8/2019 | Black |
| 2020/0113322 A1 | 4/2020 | Balestrini |
| 2021/0100717 A1 | 4/2021 | Beck |
| 2021/0299304 A1 | 9/2021 | Concannon et al. |
| 2022/0087893 A1 | 3/2022 | Black |
| 2022/0241136 A1 | 8/2022 | Costa |
| 2023/0010191 A1 | 1/2023 | Black |
| 2023/0172799 A1 | 6/2023 | Black |
| 2023/0200811 A1 | 6/2023 | Black |

FOREIGN PATENT DOCUMENTS

| | | |
|---|---|---|
| CN | 2449536 Y | 9/2001 |
| CN | 102247277 A | 11/2011 |
| CN | 202802101 U | 3/2013 |
| CN | 203694035 U | 7/2014 |
| CN | 203724434 U | 7/2014 |
| CN | 204484727 U | 7/2015 |
| CN | 201530461899.2 | 4/2016 |
| CN | 201630416937.7 | 4/2017 |
| CN | 207785468 U | 8/2018 |
| CN | 208626154 U | 3/2019 |
| CN | 208770335 U | 4/2019 |
| CN | 109820708 A | 5/2019 |
| CN | 209464314 U | 10/2019 |
| CN | 209864569 U | 12/2019 |
| CN | 210750164 U | 6/2020 |
| CN | 211326656 U | 8/2020 |
| CN | 108430426 B | 9/2020 |
| CN | 212046317 U | 1/2021 |
| CN | 112426341 A | 3/2021 |
| CN | 213373701 U | 6/2021 |
| CN | 213431541 U | 6/2021 |
| CN | 214049658 U | 8/2021 |
| CN | 307097258 | 2/2022 |
| DE | 29710313 U1 | 8/1997 |
| DE | 20 2009 014 825 U1 | 2/2010 |
| EM | 003539014-0001 | 3/2017 |
| EP | 0 811 365 A2 | 12/1997 |
| EP | 2 311 426 A1 | 4/2011 |
| EP | 2 922 518 B1 | 9/2015 |
| GB | 2 331 706 A | 6/1999 |
| JP | 2002-153531 A | 5/2002 |
| JP | 6793200 B2 | 12/2020 |
| KR | 100941568 B1 | 2/2010 |

(56) References Cited

FOREIGN PATENT DOCUMENTS

| | | |
|---|---|---|
| KR | 300888480 | 1/2017 |
| RU | 2070018 C1 | 12/1996 |
| RU | 2662879 C2 | 7/2018 |
| RU | 2719940 C1 | 4/2020 |
| TW | 201412300 A | 4/2014 |
| WO | WO-87/00425 | 1/1987 |
| WO | WO-02/083054 A1 | 10/2002 |
| WO | WO-2007/051233 A1 | 5/2007 |
| WO | WO-2008/049165 A2 | 5/2008 |
| WO | WO-2012/009862 A1 | 1/2012 |
| WO | WO-2014/118596 A1 | 8/2014 |
| WO | WO-2017/193054 A1 | 11/2017 |

OTHER PUBLICATIONS

Amazon, "Savage Blaster" by Ashley Black, Earliest Review Date: Feb. 24, 2022. https://www.amazoon.com/FasciaBlaster-SavageBlaster-Ashley-Black-Discomfort/dp/B09KM8MWX3/ref=cm_cr_arp_d_pl_foot_top?ie=UTF8 (Year: 2022).

Ashleyblackguru, "Ashley Black Mini Paddleblaster", Earliest review Date: Aug. 21, 2020. https://www.ashleyblackguru.com/product/mini-paddleblaster (Year: 2020).

Ashleyblackguru, "Savage Blaster", Earliest Review Date: Nov. 12, 2021. https://www.ashleyblackguru.com/collections/body-tools/products/savage-blaster#shopify-product-reviews (Year: 2021).

International Search Report and Written Opinion on PCT/US2022/052052 dated Mar. 10, 2023, 12 pps.

Youtube, "Discover the SavageBlaster", Published Date: Jul. 22, 2022I https://www.youtube.com/watch?v=uBxEX3waWSk (Year 2022).

Youtube, "How To Select The Right Fascia Blaster For You", Published Date: Nov. 27, 2020. https://www.youtube.com/watch?v=bQojqSYrhwQ (Year: 2020).

Amazon, "FasciaBlaster Trigger Point Tools", Nov. 6, 2017, https://www.amazon.com/Mini-Blaster-Ashley-Black-Guru/dp/B075M26CJT/ref=cm_cr_arp_d_pl_foot_top?ie=UTF8. Shown on p. 1. (Year: 2017).

Amazon, "Mini Paddle Blaster", Apr. 8, 2021. https://www.amazon.com/Mini-Paddle-Blaster-Cellulite-FasciaBlaster/dp/B08LZR7GWW/ref=sr_1_2?dchild=1&keywords=Ashley+Black+Guru&qid=1617887539&sr=8-2. Shown on p. 1. (Year: 2021).

Amazon, "Trigger Point Massager Massage Tool", Jan. 18, 2019. https://www.amazon.com/Trigger-Point-Massage-Tool/dp/B075FXVB39/ref=cm_cr_arp_d_product_top?ie=UTF8. Shown on p. 1. (Year: 2019).

Ashley Blacks, "Mini Paddleblaster1", Aug. 21, 2020. https://www.ashleyblackguru.com/products/mini-paddleblaster-1#shopify-product-reviews. Shown on p. 1. (Year: 2020).

Ashleyblackguru, "Mini 2", Nov. 12, 2017, https://www.ashleyblackguru.com/products/mini-2#shopify-product-reviews. Shown on p. 1. (Year: 2017).

Communication pursuant to Rules 161 (1) and 162 EPC for corresponding EP Application No. 14709121.9, mailed Oct. 6, 2015, 2 pages.

D'arsonval High Frequency Device Skin Tightening Spot Wrinkles Remover Acne Treatment, www.topbeautybuy.com, 2017, 6 pages.

European Pat. Appl. No. 14709121.9, Communication dated Feb. 9, 2021, 6 pages.

Examination Report for corresponding EP Application No. 14709121. 9, mailed Dec. 7, 2017, 5 pages.

Fascia Blaster Cellulite Massager Full Body Massage Us Seller Lot of 2, www.terapeak.com, 4 pages.

International Preliminary Report on Patentability for corresponding PCT/US2014/018043, mailed Aug. 25, 2015, 6 pages.

International Preliminary Report on Patentability for corresponding PCT/US2017/031384, mailed Nov. 6, 2018, 6 pages.

International Search Report and Written Opinion for corresponding PCT/US2014/018043, mailed May 6, 2014, 10 pages.

International Search Report and Written Opinion for corresponding PCT/US2017/031384, mailed Sep. 14, 2017, 9 pages.

Vola Massager, Wayback Machine Jan. 17, 2008 capture of http://www.chinatraderonline.com/Massager/VOLA-MASSAGER-193802857.htm, retrieved from https://web.archive.org/web/20080117105426/http:/www.chinatraderonline.com/Massager/VOLA-MASSAGER-193802857.htm, Jul. 19, 2021, 1 pg.

Youtube, "Mini1 Paddleblaster", Oct. 9, 2020. https://www.youtube.com/watch?v=LIK17dCevBQ. Shown at the 0:02 second mark. (Year: 2020).

'057 Patent Holder Disclosure "Product Development LumpBuster Case Study" (LB Case) date May 26, 2013, pdf archive link: https://web.archive.org/web/20111228161639/http://www.chinatraderonline.com/Beauty-Equipment/Octopus-Massager-13342511.htm, 2 pgs.

Amazon, "FasciaBlaster ProBlaster", Earliest Review Date: Oct. 14, 2022. https:/www.amazon.com/FasciaBlaster-ProBlaster-Ashley-Black-Discomfort/dp/BOB916ZPYP/ref=cm_cr_arp_d_pl_foot_top?ie=UTF8 (Year: 2022).

Ashleyblackguru, "Problaster", Earliest Review Date: Aug. 9, 2022. https:/Avww.ashleyblackguru.com/collections/all/products/problaster (Year: 2022).

Definition of the term "Circular", Miriamwebster.com, captured on Feb. 1, 2024.

Octopus-Shaped Massager (Octopus), Sales Pgs Dated 2006-2011, Retrieved from: https://web.archive.org/web/20060514183134/http://www.chinatraderonline.com/Files/Health-2Beauty/Beauty-Equipment/Octopus-Massager-13342022084.jpg, 1 pg.

"BioSwiss 2-Pack Full Body Massager", Sep. 29, 2020, Site visited Apr. 15, 2025, Available from Internet URL:https://www.amazon.com/dp/B07X8K9N61/?th=1.

"The Single Claw FasciaBlaster by Ashley Black", Dec. 16, 2022, Site visited Apr. 15, 2025, Available from Internet URL:https://www.amazon.com/Singel-Claw-FasciaBlaster-Ashley-Black/dp/BOBM4VPVYV?ref_=ast_sto_dp.

\* cited by examiner

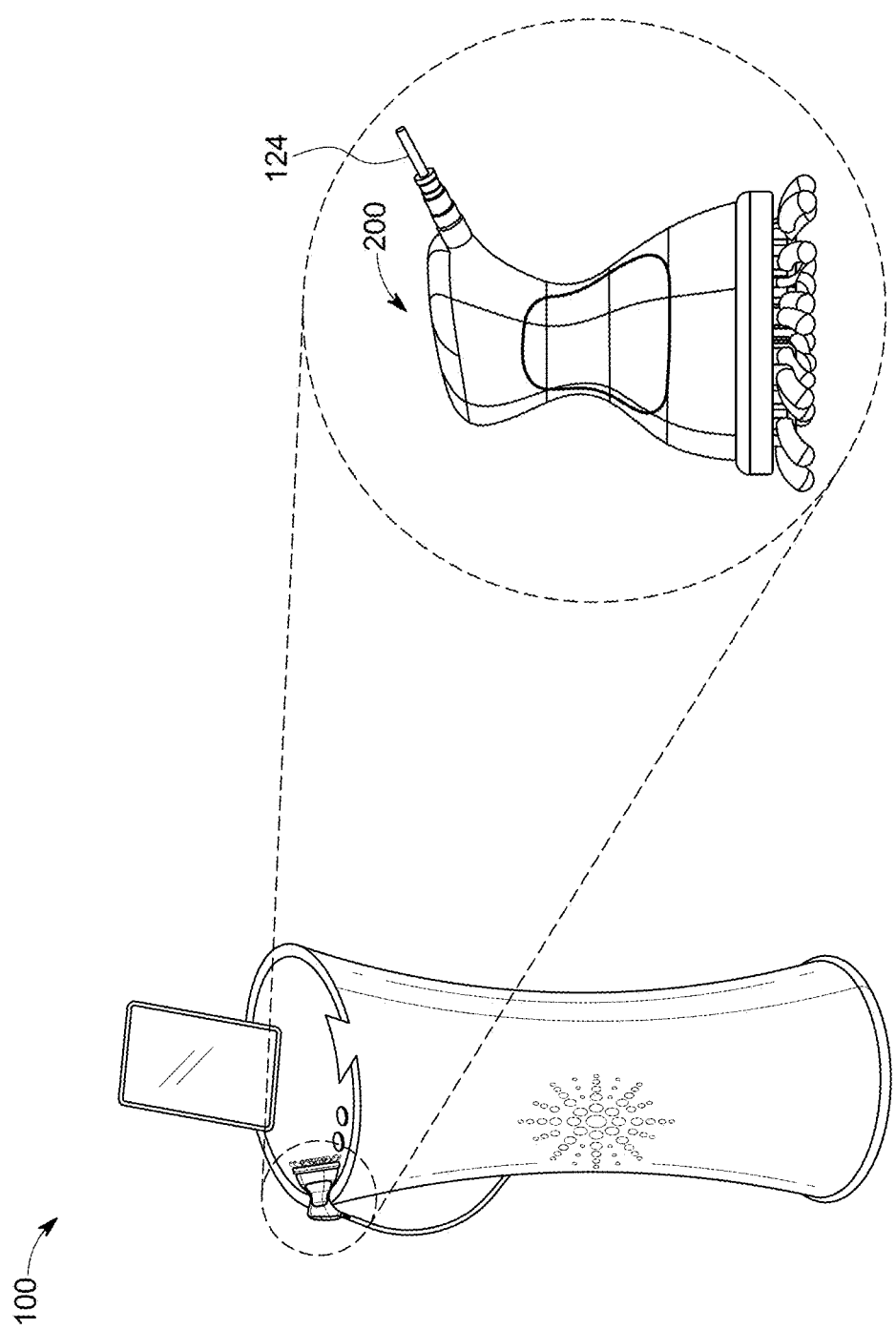

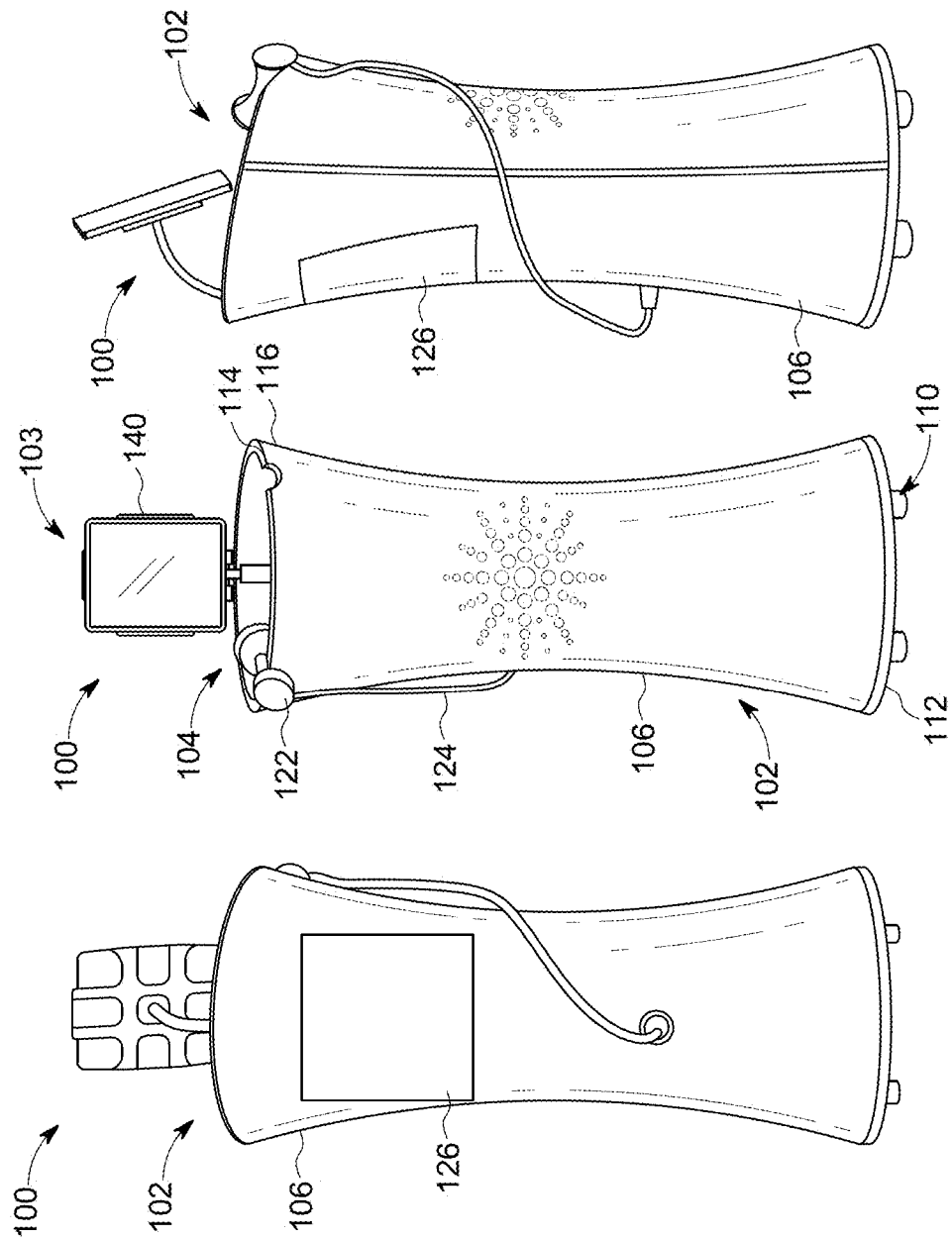

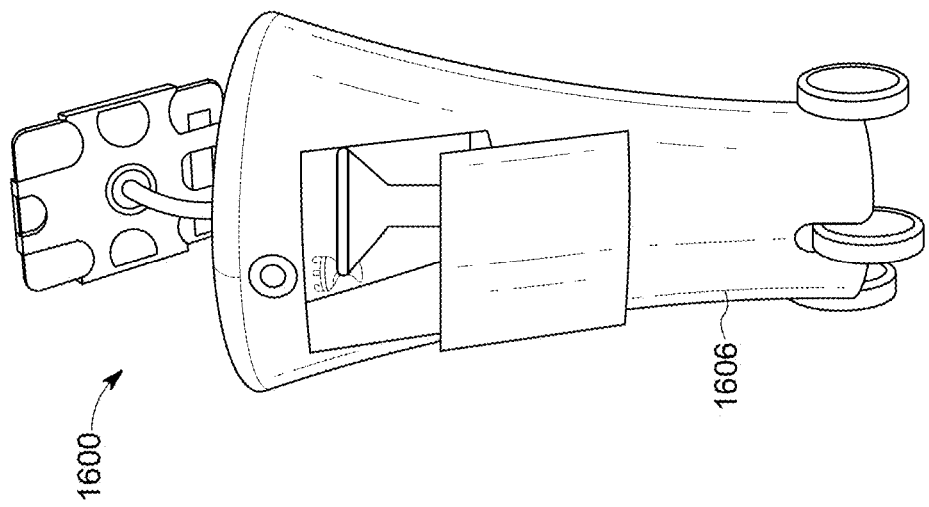
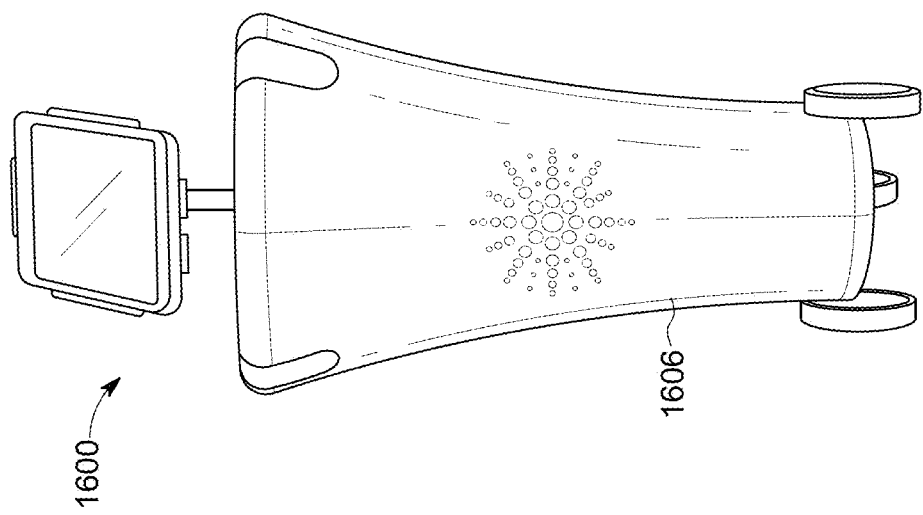

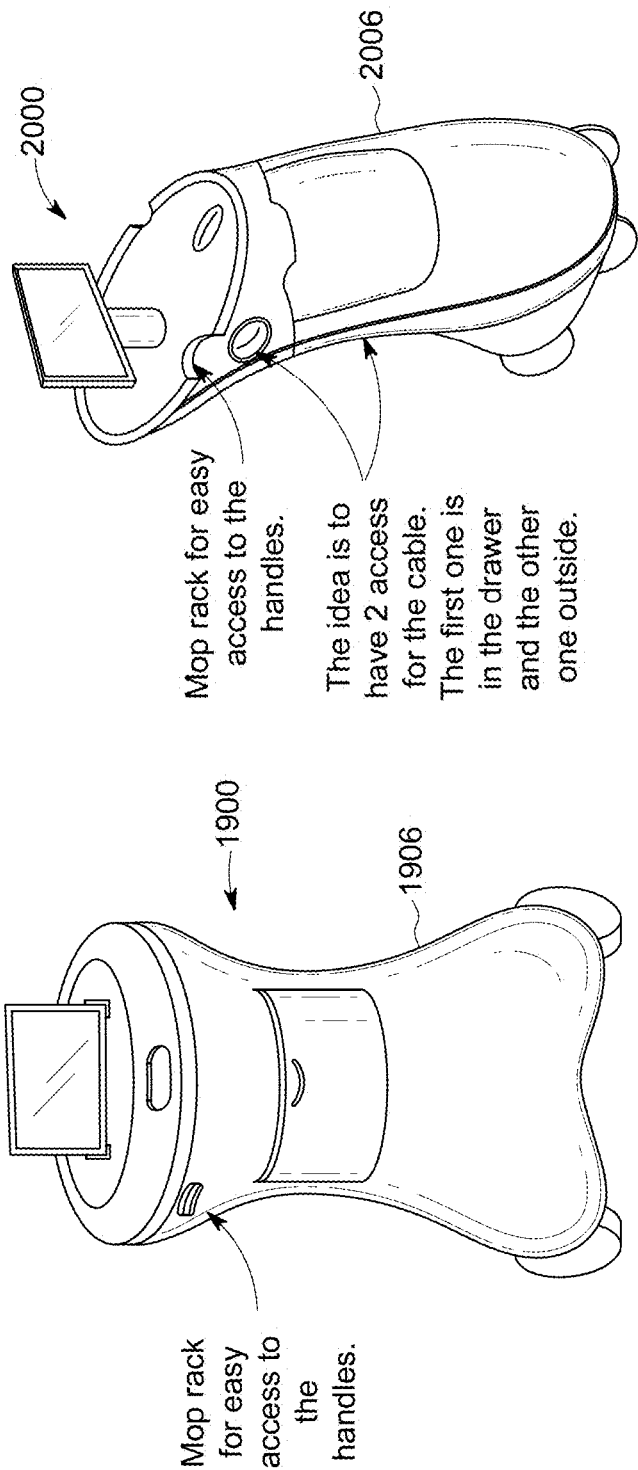

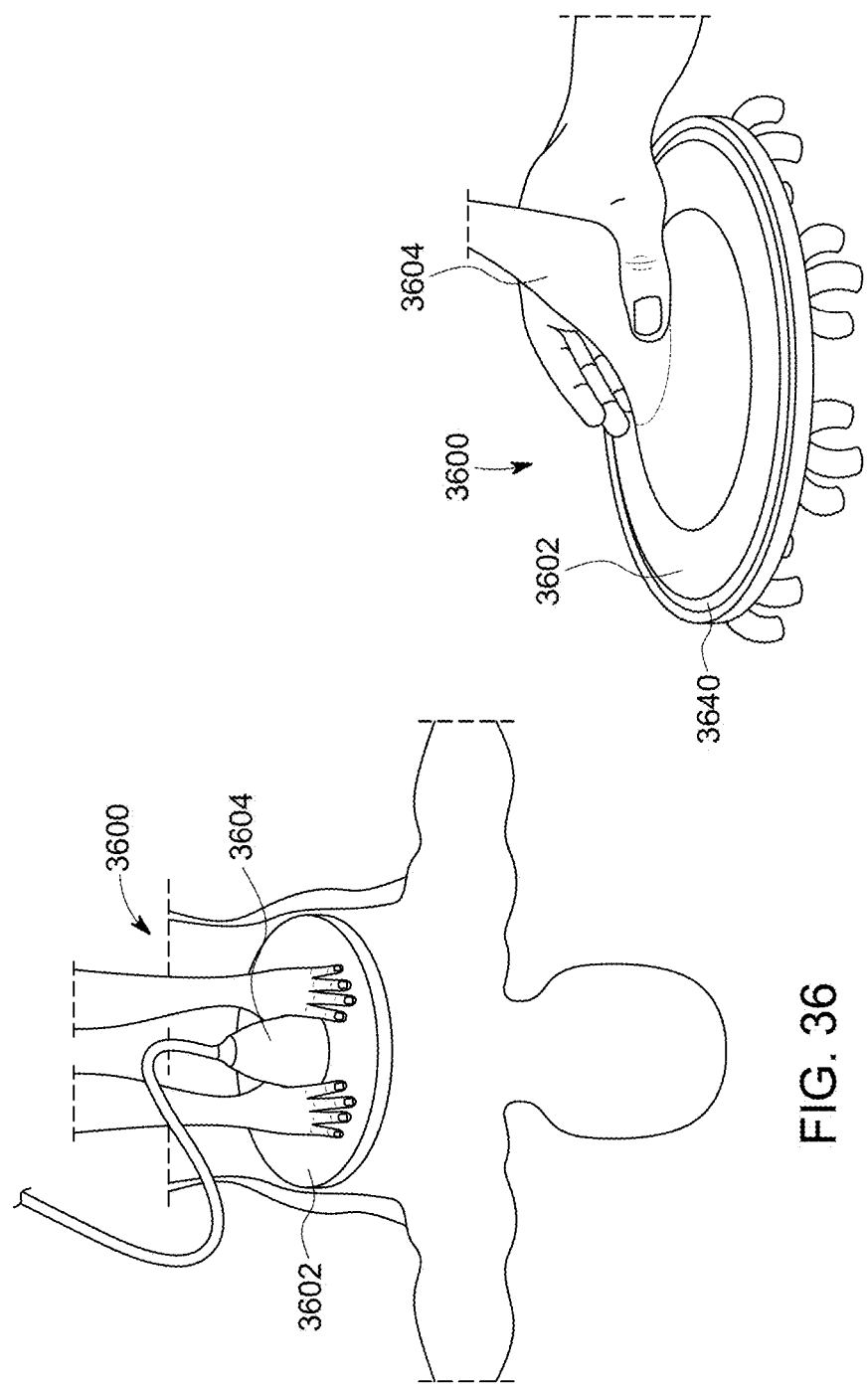

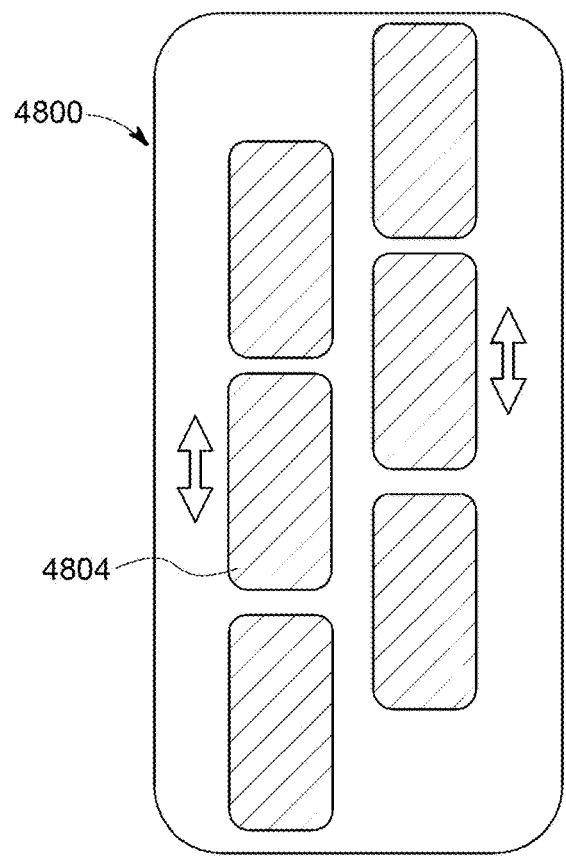
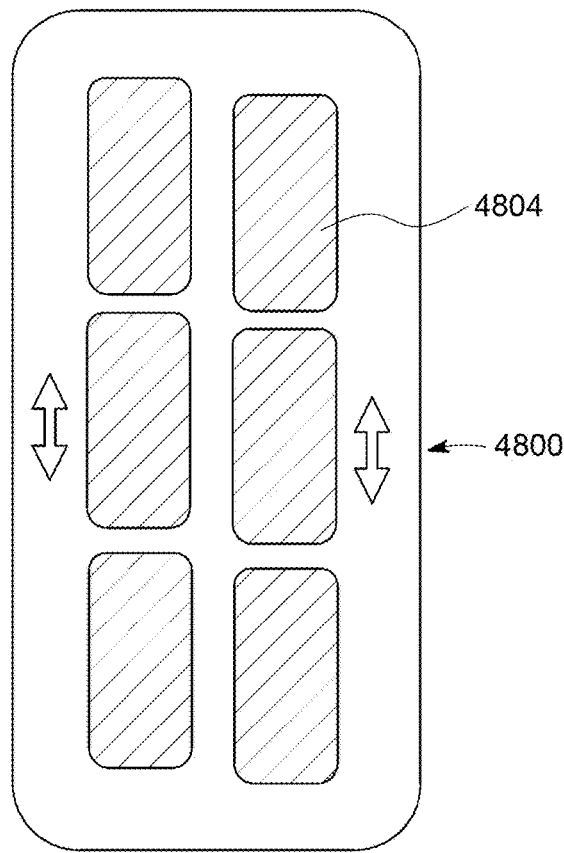
FIG. 48        FIG. 49
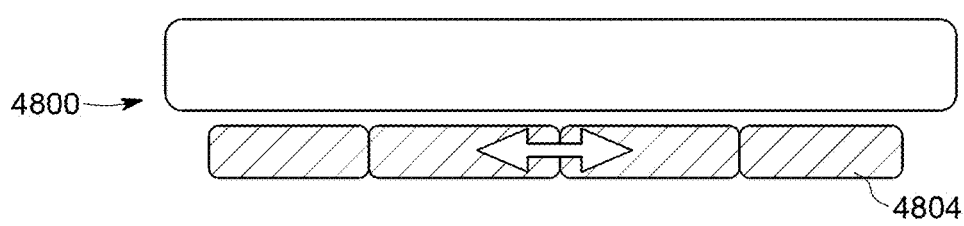
FIG. 50

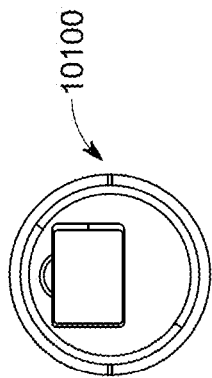
FIG. 101C
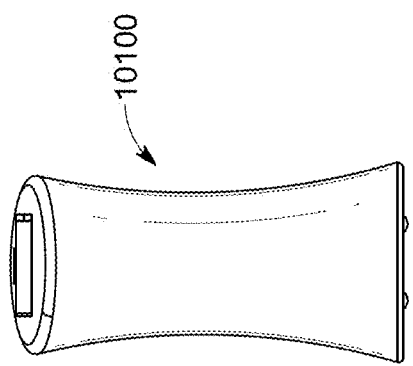
FIG. 101F
FIG. 101E
FIG. 101D
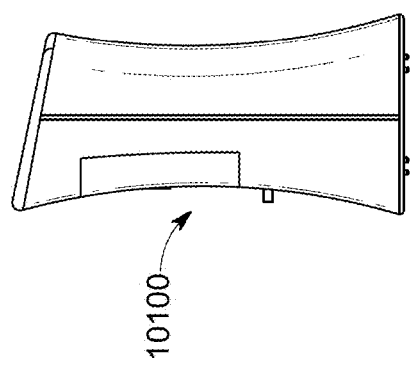
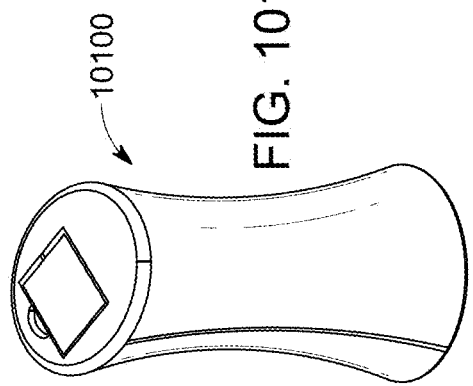
FIG. 101A
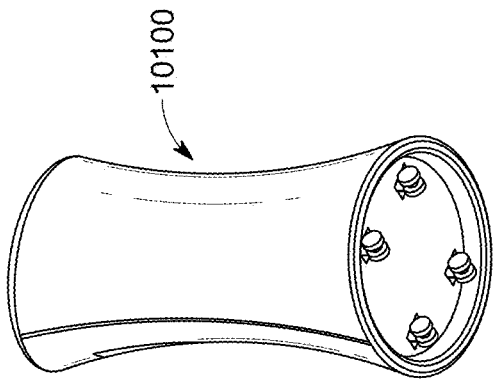
FIG. 101B

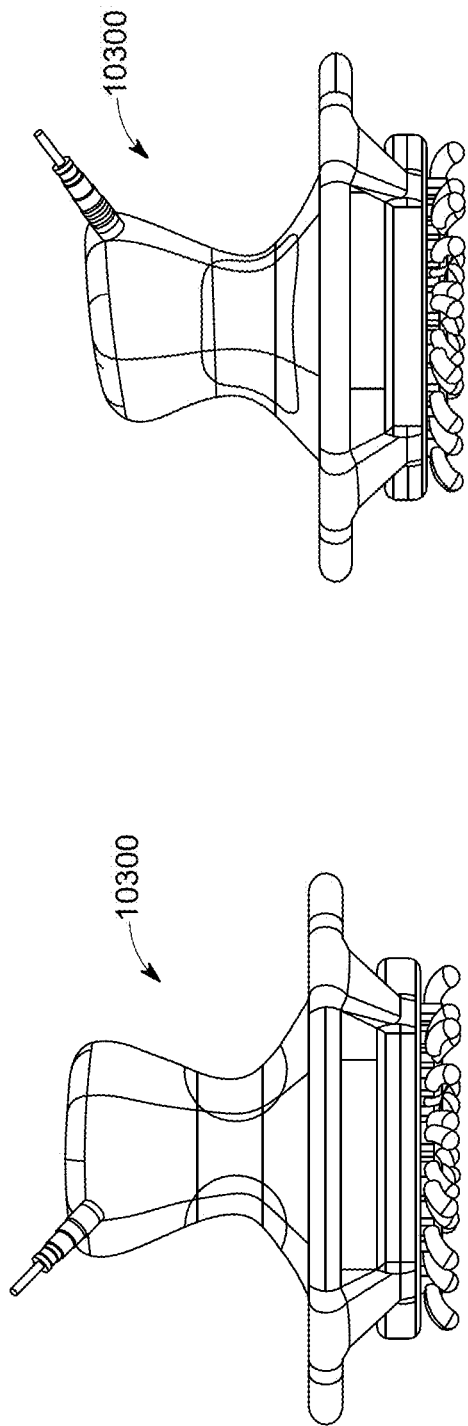
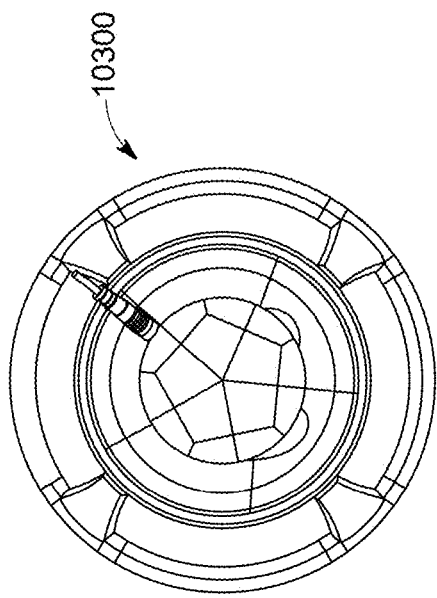
FIG. 103F
FIG. 103G
FIG. 103E

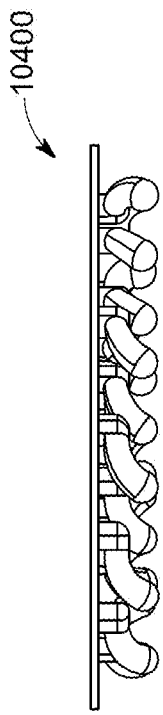
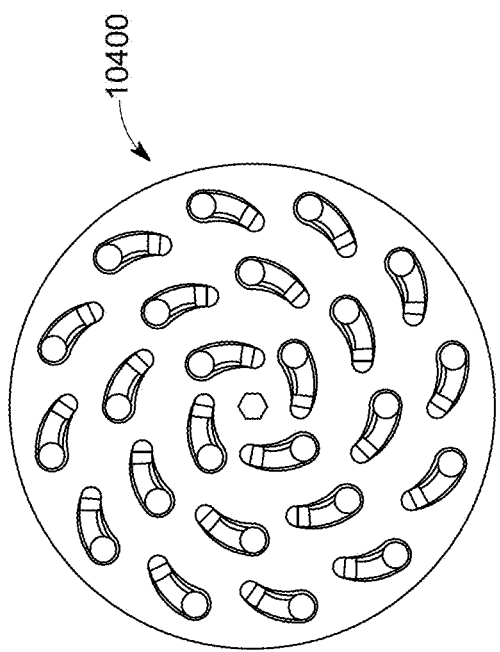
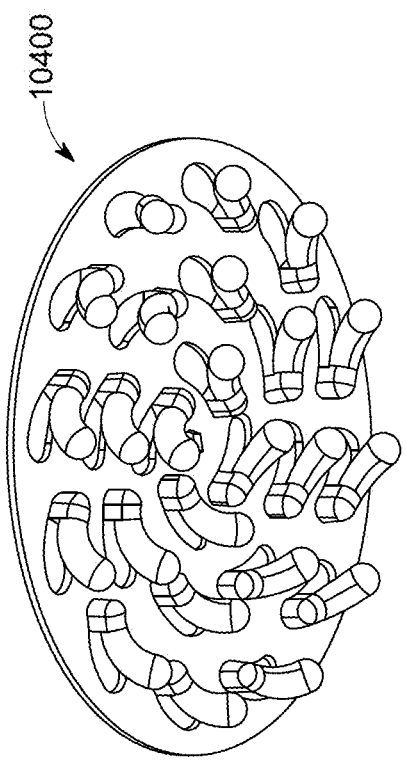
FIG. 104B
FIG. 104D
FIG. 104A
FIG. 104C

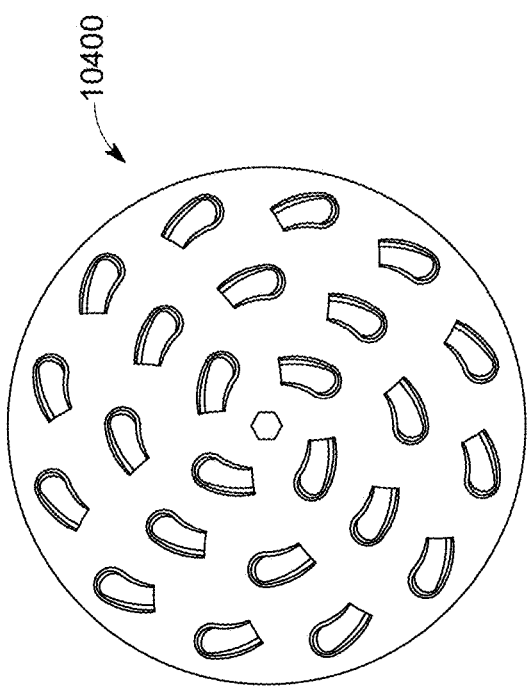
FIG. 104F
FIG. 104G
FIG. 104E

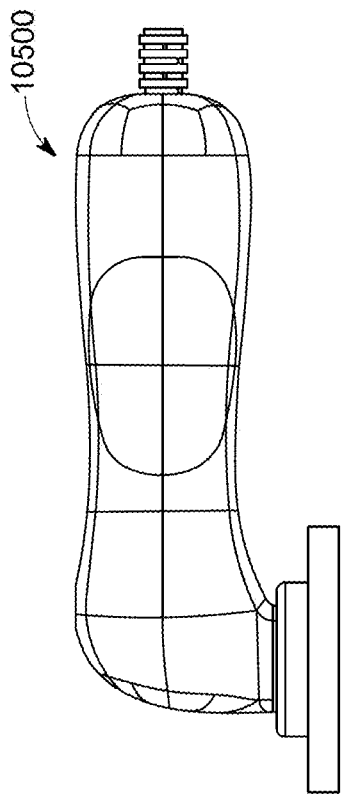
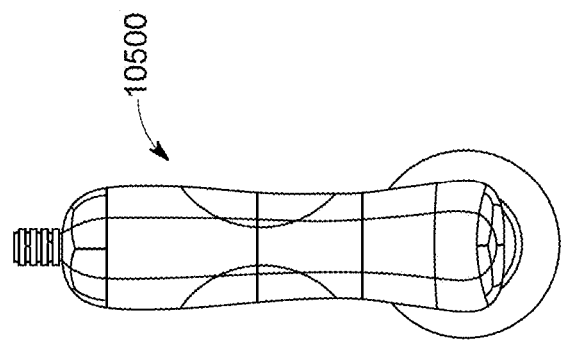
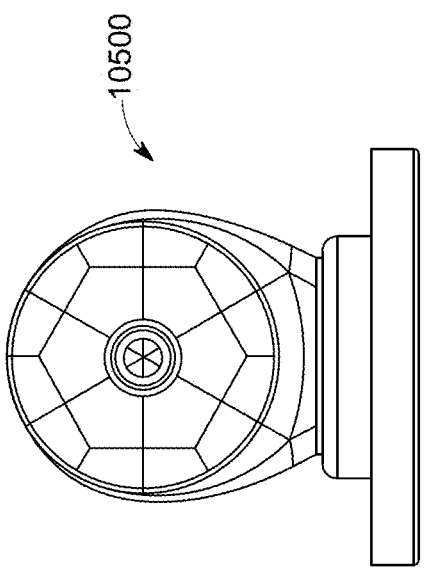
FIG. 105F
FIG. 105G
FIG. 105E

SYSTEM AND METHOD FOR PERFORMING TISSUE TREATMENT USING POWERED TREATMENT DEVICES

CROSS-REFERENCE TO RELATED PATENT APPLICATIONS

The present application is a Continuation-in-Part of co-pending U.S. patent application Ser. No. 17/545,920, filed on Dec. 8, 2021, which claims priority to, and the benefit of, U.S. Provisional Patent Application Ser. No. 63/286,536, filed on Dec. 6, 2021, and further claims priority to, and the benefit of, U.S. Provisional Patent Application Ser. No. 63/347,961, filed Jun. 1, 2022, the contents of which are hereby incorporated herein by reference in their entirety.

BACKGROUND

Fascia tissue is a layer of fibrous tissue that operates as a connective tissue that surrounds muscles, groups of muscles, nerves, blood vessels, etc. The tissue allows for proper functioning of muscles with respect to one another (e.g., sliding past one another). When fascia tissue becomes damaged through injury, tissue knots, adhesions in the fascia tissue, medical reasons, or otherwise, the fascia tissue can take time to correct itself or require manipulation to release the fascia tissue and allow for proper functioning of the tissue to allow the underlying muscle to properly operate. In some cases, the fascia tissue can be released or corrected without much difficulty, while in other cases, restoring the fascia tissue to its proper form can take considerably more effort. Other reasons for releasing fascia tissue may include cosmetic reasons, especially for people who have dimpled skin, which is often caused by fascia tissue extending through fat cells, thus causing dimples to appear on the skin. Often, when the fascia tissue is properly released, the dimples can be considerably reduced or eliminated.

Fascia tissue is both structural and inter-structural. Fascial tissue is located throughout the human (and other animals) bodies, including attaching to skin, forming a casing over muscles, forming inter-muscular layers (myofascial tissue), being positioned at lower depths of layered muscles, surrounding organs, and located around bones. For the lower depth fascia, especially when multiple muscles stacked are stacked, adhesions of the fascia tissue or other fascia tissue structure misalignments or damage can result in a variety of discomforts or worse problems, such as circulatory flow, pain, misalignment of muscles and bones, joint problems, and so forth. As such, there is a need to treat fascia tissue at any location of the body.

Fascia tissue treatment is complicated and scientifically challenging to diagnose and treat. The diagnosis and understanding of a myriad of problems that result from damaged or misaligned fascia tissue is not well understood, and, thus, often not properly treated. For example, pain, circulatory problems, and other physical ailments are often treated using pain medicine, surgery, heating pads, conventional massage, chiropractor join adjustment, and many other medical treatments that essentially treat the symptom and not the cause of the physical ailments that stem from damaged or misaligned fascia tissue. Moreover, even if diagnosed, the ability to treat the fascia tissue, especially myofascial tissue, can be difficult because tools to treat such tissue are limited and generally not configured for such treatments.

SUMMARY

To overcome the problem of having limited tools for treating fascia tissue, the principles described herein provide for treating a wide variety of fascia tissue that may be positioned throughout the body, human and animal. The tools described herein are configured to treat or remodel (e.g., removal of adhesions, realignment, etc.) fascia tissue at depths and orientations that cannot be achieved using other tools to massage techniques. For example, rollers, nubs, or devices with other configurations generally are not capable of penetrating muscle casing or surface of a muscle much less layered muscle (e.g., two or three layers of muscle of quadriceps muscles). To property treat the fascia tissue, powered (and unpowered) devices with effectors (e.g., fingers of a certain configuration connected to a panel) creates a "fascial shearing" that triggers the body's natural mechanism to remodel or restructure the fascia tissue that has been damaged or is disfigured in a manner that results in negative effects on the human body.

A fascia tissue treatment system may include a base station that powers tissue treatment devices that are used to treat fascia or other tissue of patients. The tissue treatment devices may be powered devices, and include actuators that are used to move tissue treatment elements. The actuators may be motors that cause an effector inclusive of a support structure, such as a disc or other shaped structural member, on which the tissue treatment elements are connected or formed. In an embodiment, the effector may be a unitary piece, where a support structure and protrusions or fingers extend. Alternatively, the fingers may be detachably coupled to the support structure. The fingers may have a base that connects to or is integrated with the support structure, curved shafts, and rounded tips.

In at least one embodiment, the tissue treatment elements may form part of a tissue treatment assembly that is configured for rotation by the actuator in an ON state. The tissue treatment assembly may be uniquely designed to improve treatment effectiveness based on the direction of movement of the actuator. For example, the tissue treatment assembly may include a panel and a plurality of finger members that are shaped based on a rotational direction of the actuator or panel. In at least one implementation, the finger members are curved away from the panel along at least one of a radial direction and/or a circumferential direction of the panel, which can also increase the strength of the finger members during operation and in response to application of axial pressure acting on the finger members during treatment.

In operation, base station may be utilized to provide electrical power (or other power source types) to provide tissue treatment functions, such as warm-up, tissue release, and/or tissue treatment. The base station may support (i) a heater, such as an infrared heater element, to warm up tissue of a patient, (ii) an ultrasound and/or radio frequency (RF) device to provide for tissue release, and tissue treatment devices of different configurations to provide for fascia or other tissue treatment.

Moreover, the tissue treatment device may receive electrical power that drives a rotating motor therein. The motor may cause the effector to spin. An operator, either a medical professional or a patient him or herself, may engage the tissue treatment device to cause the effector to spin while pressing the effector onto a patient's skin. The amount of force being applied may vary depending on a modality being performed along with a particular location on the patient's body being treated. For example, treatment to a face or scalp uses much less force than body parts with larger surface area and more dense tissue (e.g., muscle). Moreover, if fascia tissue being treated is causing acute pain, then less force and, possibly, less speed of the rotating effector may be used. It should be understood that a wide variety of treatment protocols may be utilized. Moreover, although a spinning effector may be utilized, other actuator types and effectors may be utilized. For example, motors that cause an effector, such as a square or rectangular effector, to cause the effector to move linearly (e.g., forward and backward along a single axis). Powered tissue treatment devices may be utilized, as well, and have a variety of different controllers.

The base station may further include an electronic device, such as a tablet, that may be used to manage operators, patients, treatment plans, collect data, and/or control operations of the tissue treatment device(s). In an embodiment, the base station may further be configured with an ultrasound scanning device and optionally camera device that enables an operator to perform ultrasound scanning on tissue of a patient and record the scans to aid the operator know the type of treatment that the patient in that region should have. The computing device may capture the ultrasound images and/or visual images and store those images for later viewing. Additionally, the computing device may compare the images over time to assist an operator in determining how past treatments have resulted in improving tissue of the patient. In an embodiment, artificial intelligence (AI) software may be utilized to identify fascia tissue or other tissue abnormalities or structural issues to aid an operator understand how treatments are to be made. In an embodiment, the computing device may be configured to recognize certain structural issues with fascia tissue and aid or recommend to an operator or other medical professional in creating a treatment plan.

One embodiment of the present disclosure relates to a powered treatment device for treating fascia tissue. The powered treatment device may include a housing, an actuator, and a tissue treatment assembly. The actuator may be configured to rotate and may be coupled to and disposed substantially within the housing. The tissue treatment assembly may include a panel and a plurality of finger members. The panel may be detachably coupled to the actuator so as to be rotated with respect to the housing when the actuator is in an ON state. The plurality of finger members may be fixedly coupled to the panel at a proximal end of the respective finger members. The finger members may be rigid and extend away from the panel. Each one of the finger members may have a respective central axis that extends from the proximal end to a distal end of the respective finger member. At least one of the central axes may extend at least partly along a radial direction and/or a circumferential direction of the panel.

Another embodiment of the present disclosure relates to a tissue treatment assembly that includes a panel, a support member, and a plurality of finger members. The support member may be disposed on the panel and may include a connecting element configured to detachably couple the support member to an actuator. The plurality of finger members may be coupled to the panel at a proximal end of the finger members. The finger members may be rigid and may extend away from the panel. Each one of the plurality of finger members may have a respective central axis extending from the proximal end to a distal end of the respective finger member. At least one of the central axes may extend at least partly along a radial direction and/or a circumferential direction of the panel.

BRIEF DESCRIPTION OF THE FIGURES

A more complete understanding of the method and apparatus of the present invention may be obtained by reference to the following Detailed Description when taken in conjunction with the accompanying Drawings wherein:

FIG. 1 is an illustration of a front isometric view of an illustrative fascia tissue therapy system;

FIG. 2 is an illustration of a fascia tissue fitness device of the illustrative therapy system of FIG. 1;

FIG. 3A is a rear view of the illustrative fascia tissue therapy system of FIG. 1;

FIG. 3B is a side view of the illustrative fascia tissue therapy system of FIG. 1;

FIG. 3C is a front view of the illustrative fascia tissue therapy system of FIG. 1;

FIG. 16A is an illustration of a front isometric view of yet another illustrative fascia tissue therapy system;

FIG. 16B is a rear view of the illustrative therapy system of FIG. 16A;

FIG. 19 is an illustration of a front isometric view of yet another illustrative fascia tissue therapy system;

FIG. 20 is an illustration of a front isometric view of yet another illustrative fascia tissue therapy system;

FIG. 36 is an illustration of a front isometric view of yet another illustrative fascia tissue treatment device;

FIG. 37 is another isometric view of the illustrative fascia tissue treatment device of FIG. 36;

FIGS. 48-49 are illustrations of bottom views of yet another illustrative fascia tissue treatment device;

FIG. 50 is an illustration of a side view of the illustrative fascia tissue treatment device of FIG. 48;

FIGS. 101A-101F are illustrations of perspective, another perspective, top, side, front, and bottom views of yet another illustrative fascia tissue therapy system;

FIGS. 103A-103G are illustrations of bottom, front, perspective, left, rear, right, and top views of yet another illustrative fascia tissue fitness device;

FIGS. 104A-104G are illustrations of bottom, front, perspective, left, rear, right, and top views of yet another illustrative tissue treatment effector;

FIGS. 105A-105G are illustrations of bottom, front, perspective, left, rear, right, and top views of yet another illustrative fascia tissue fitness device;

FIG. 11 is an illustration of a side cross-sectional view of the illustrative fascia tissue treatment device of FIG. 111;

FIG. 119 are images of a foot having poor circulation before fascia tissue treatment and after fascia tissue treatment.

DETAILED DESCRIPTION

Figure 5:
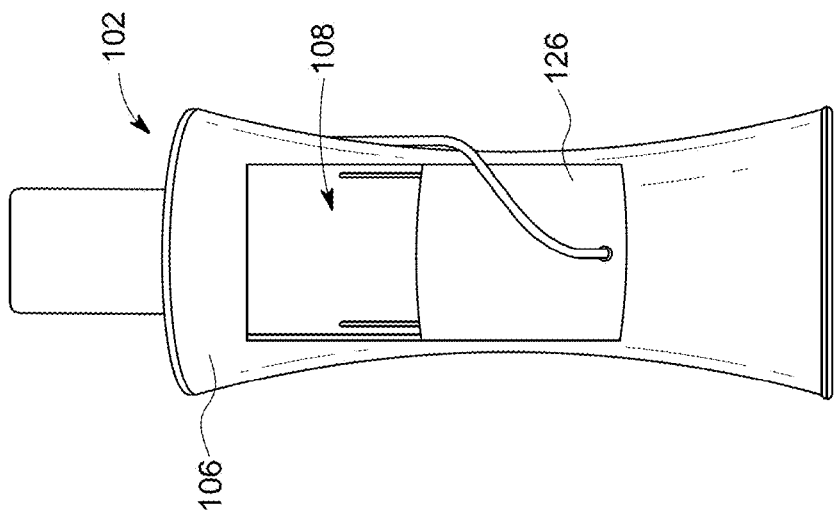
FIG. 5 is a rear view of the illustrative fascia tissue therapy system of FIG. 1 shown with an access panel in an opened position.
Figure 4:
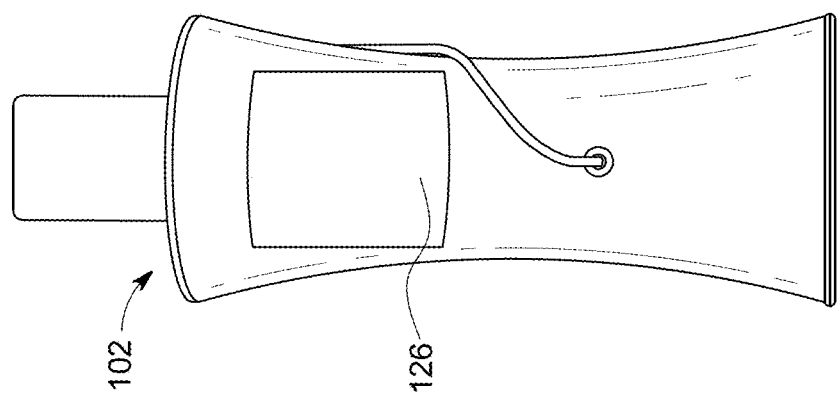
FIG. 4 is a rear view of the illustrative fascia tissue therapy system of FIG. 1 shown with an access panel in a closed position.

Existing fascia tissue treatment devices require manual manipulation by a user to move tissue treatment elements across a patient's skin. While effective, users performing self-treatment using hand-held tools may not use sufficient force and/or speed to ensure adequate treatment of the fascia tissue. Conventional motorized scalp or tissue massagers are not designed to release fascia tissue. For example, the messaging and/or brush elements employed by these conventional systems are specifically designed for user comfort and skin surface treatment, but are not suitable for working the underlying tissue in a manner meant to improve fascia tissue fitness to perform restructuring of fascia tissue at different layers starting at the skin and working down towards or even to the bone. Additionally, fascia tissue treatment may utilize considerable application of force between the tissue treatment elements and a person or patient's skin, which may cause stress to an actuator being used to drive the tissue treatment elements, thereby resulting in premature failure of the actuator. Such stress, for example, may be caused by using forces in treating fascia tissue that higher torque has to be produced by the actuator, which may result in heat produced in the actuator due to high current draw therein. As such, various configurations of actuators and tissue treatment elements may be utilized to avoid such high-torque situations. It should be understood that the fascia tissue treatments are meant to be applied to lubricated skin of a patient, where the lubrication may be any fluid, such as oil, applied to the skin that reduces friction between tissue treatment elements, such as protrusions (e.g., fingers), of an effector of the tissue treatment device. Alternatively, a cover, such as a sleeve formed of a slick external material, may be placed on skin of a user to enable the tissue treatment device to be applied to the cover to avoid or use a minimal amount of lubrication.

Referring to the Figures generally, a fascia tissue therapy system is shown that addresses the foregoing issues and provides an all-in-one system for diagnosing and treating damage to fascia tissue. The therapy system includes a base station and a therapy device inclusive of an actuator and tissue treatment element that is actuated (e.g., rotated, vibrated, linearly translated, etc.) by the actuator. The tissue treatment element may form part of an effector that is detachably coupled to the base station. The base station may be configured in a number of ways, including (i) operating as a cabinet with actuated heads that control operation of an effector with tissue treatment elements, (ii) operating a computing device to help monitor and manage treatment sessions of patients by an operator of the therapy system, and (iii) operating a computing device that includes a control system for the therapy system that is configured to (a) determine a tissue condition based on data received from the therapy device (e.g., sensors onboard the therapy device, etc.), (b) determine a treatment regimen based on the condition, and (c) control and monitor operation of the therapy device to treat the condition.

Because the fascia tissue therapy system may support different types of treatment devices, such as radio frequency (RF) treatment device(s), ultrasonic cavitation treatment device(s), and fascia tissue treatment device(s), different power types and levels may be utilized for each of the treatment devices. As such, the system may be configured to supply different power types and/or levels to support each of the different devices, and be configured to manually, semi-automatically, or automatically set a different power type and/or level or include different power sources for such support. The different power types and/or levels may be controlled by mechanical, electrical, and/or software and/or hardware (e.g., mechanical switch or other selector) by an operator, for example. In an embodiment, electronics may be utilized to condition power for the different types and/or levels. For example, if three different power types (e.g., DC 100 v, AC 120 v/1-phase, AC 208 v/3-phase) as to be used to support three different treatment devices, the electronics that supply power each of those type types to one or more outlets at the base station into which an operator may plug the treatment devices.

In an embodiment, the computing system may also be configured to track treatment progress and re-evaluate the tissue condition at periodic (e.g., during periodic treatments) or aperiodic (e.g., during non-periodic treatments) intervals. The therapy device may be designed to monitor and treat damage to fascia tissue or otherwise manipulate and restore fascia tissue. The therapy device may include a direct drive motor and an effector that is detachably coupled to the therapy device and powered into rotation (or otherwise) by the direct drive motor. Unlike existing powered devices, which typically use a transmission (e.g., gear, gear set, etc.) to achieve the high speeds required for operation, the direct drive motor of the present disclosure may be coupled to the effector without an intervening transmission or gear set. Using a direct drive motor may reduce heat generation and wear on the treatment device as compared to a typical motor that utilizes a gear box, thereby allowing use of the device over longer treatment intervals and with less risk of changes in performance during treatment. A high torque-to-weight ratio of the direct drive motor may also provide a lower weight of the therapy device as compared to a therapy device that uses a non-direct drive motor that includes gears, cooling fluid and channels through which the cooling fluid flows, etc.

The effector for the treatment device may be structured to engage a patient's skin and manipulate the fascia tissue to restore and restructure the fascia tissue to its proper form. In being structured to engage a patient's skin, the effector may be shaped to avoid cutting, scraping, or otherwise harm a patient's skin while being configured to treat the fascia tissue beneath the skin. In contrast with conventional motorized scalp or tissue massager designs, the effector and/or tissue treatment assembly of the present disclosure may be shaped or otherwise structured based on a direction of movement of the effector during treatment to improve treatment effectiveness as compared to effector designs that are not oriented with the direction of travel of the effector. As described herein, the system may be used to treat the fascia tissue at different levels (e.g., shallow, medium depth, deep) depending on the modality and location of the patient (e.g., face may be shallow, arm may range from shallow to medium, leg may range from shallow to deep). In some embodiments, the effector may be configured to treat shallow, medium depth, or deep tissue. For example, the shape of the effector and fingers (or other features) that are to contact a patient's skin may have different lengths, widths, tip diameters, curve angles, or other dimensions to be used for shallow, medium depth, or deep tissue. Shallow may mean up to one-tenth of an inch, medium depth may mean up to one inch, and deep tissue may mean more than one inch. It should be understood that alternative ranges may be utilized.

The effector may include a panel (e.g., a support structure, etc.) and/or plate that is detachably coupled to the treatment device and that includes multiple tissue treatment elements. In some embodiments, the panel may include a mount at an intermediate radial position along the panel that connects the panel to the treatment device to reduce a torque required to maintain movement of the panel during operation. The panel may also include supports and/or be shaped to ensure uniform contact between the tissue treatment elements and the patient's skin across the face of the panel. In an embodiment, the panel may be flat, round, and have the protrusions e.g., tissue treatment elements) on one side of the panel. However, it should be appreciated that "panel" as used herein also includes various other support structure shapes. For example, in some embodiments, the panel may be curved or rounded (e.g., parabolic) from a base portion to a tip with the tissue treatment elements connected to and radially extending therefrom. In yet other embodiments, the panel can include other non-flat structures such as a waffle structure, a honeycomb-shaped structure, a dome and/or conical extension and/or protrusion. In further embodiments, the panel may include or be formed from a non-contiguous structure such as ribs, bars, standoff-bridges, etc.

The tissue treatment elements may include a plurality of rigid (e.g., inflexible, stiff, or not easily bent, etc.) protrusions (e.g., fingers and/or finger members, wave shape, pyramid shape with curved tips, spline, or other geometric or non-geometric shape) that extend axially away from the panel. In further contrast to conventional motorized scalp and tissue massagers, the effectors of the present application may be specifically structured to manipulate fascia tissue layers below the skin surface and to take advantage of the direction of movement of the effector during treatment to improve overall treatment effectiveness. For example, tissue treatment elements (e.g., fingers) may extend away from panel (e.g., flat circular member) at an angle (e.g., along a radial direction and/or a direction of rotation of the effector) to improve treatment efficacy and/or allow different treatment modalities depending on the rotational direction of the effector. The tissue treatment elements (e.g., fingers, member that includes one or more fingers that may be connected to a panel, or any other structure that includes elements that contact skin for treating fascia tissue) may have a variety of different shapes, sizes, orientations, alignments, and/or configurations. In one embodiment, the tissue treatment elements (e.g., fingers) may have multiple different sized fingers (e.g., small in the middle and large on the outside of the panel having a flat, circular shape or any other shape that may or may not be flat).

Referring to FIG. 1 and FIGS. 3A-3C, an illustrative fascia tissue therapy system 100 (e.g., treatment system, etc.) is shown. As shown in FIG. 3B, the system 100 includes a base station 102 (e.g., cabinet, power source(s), computer, communications equipment, etc.) that is configured to house and/or support various equipment, such RF treatment device(s), ultrasound device(s), a computing system 103, one or more powered fascia tissue treatment devices 104, and/or other system components. The base station 102 includes an enclosure 106 defining an interior cavity 108 (as shown in FIG. 5) that is sized to store multiple fascia tissue treatment devices, tissue treatment assemblies, and/or tissue treatment elements therein. The base station 102 may also include a set of wheels 110 (e.g., casters, rollers, etc.) mounted to a bottom or lower wall 112 of the enclosure 106 to facilitate movement of the base station 102. The wheels 110 may be rotatably coupled to the base station 102 and may include locks to allow a user to prevent rotation of the wheels 110 once the base station 102 has been moved to a desired location. The number and/or arrangement of wheels 110 may be different in other embodiments.

As shown in FIG. 3B, the base station 102 includes at least one mount 114 configured to support at least one treatment device 104 in position on the base station 102. The mount 114 may include a rack that detachably couples or otherwise supports the fascia treatment device 104 on the enclosure. In the embodiment of FIG. 3B, the mount 114 may include multiple slots 116 (e.g., recessed areas, depressions, etc.) disposed along an outer perimeter of an upper wall 118 or sidewalls 120 of the enclosure 106. The slots 116 may be sized and configured to receive a handle 122 and/or head portion of the treatment device 104 therein to support the treatment device 104 along the upper end of the base station 102. In the embodiment of FIG. 1, the handle 122 hangs on an outer wall of the slot 116 and is secured in position by gravity acting on the treatment device 104. In other embodiments, the mount 114 may include other types of hangers and/or cradles. In yet other embodiments, the mount 114 may include magnets, hook and loop fasteners, and/or another form of detachable coupling to secure the treatment device 104 to the enclosure 106 when not in use.

FIG. 2 shows an illustrative fascia tissue treatment device 200 (e.g., head, etc.) for the system of FIG. 1, which may be the same as or similar to the treatment device 104 of FIG. 1. As shown in FIG. 2, the treatment device 104, 200 is electrically coupled to the base station 102 (e.g., a power source that is disposed within the base station 102) via a tether 124 (e.g., electric cable, etc.) that is coupled to and extends away from the enclosure 106. The tether 124 also includes electrical connections to power the treatment device 104, 200 and to transmit signals between sensors of the treatment device 200 and the computing system 103. In at least one embodiment, the treatment device 104, 200 is detachably coupled to the tether 124 so that the same tether 124 can be used to power multiple different treatment devices depending on the desired modality. In an embodiment, all fascia tissue treatment devices 104, 200 may be configured to utilize the same power signals, thereby enabling the system 100 to include a single power cord to which different tissue treatment devices may connect. Alternatively, different tissue treatment devices may be configured to utilized different electrical signals such that different adapters, power cords, sockets, etc. may be used for the different fascia tissue treatment devices. In yet another embodiment, one or more fascia tissue treatment devices 104, 200 may be configured with a rechargeable battery or other power source to be used in a cordless manner and be charged by the base station 102. For example, the base station 102 may be configured to provide power to larger treatment devices 104, 200, which may be configured to treat certain anatomical regions (e.g., back, core, legs, arms) to perform medium or deep tissue modalities, for example, may be wired, while smaller treatment devices that are used for other anatomical regions (e.g., face, neck, scalp, hands, feet, etc.) or shallow modalities (e.g., skin, scalp, etc.) may be self-powered.

Figure 8:
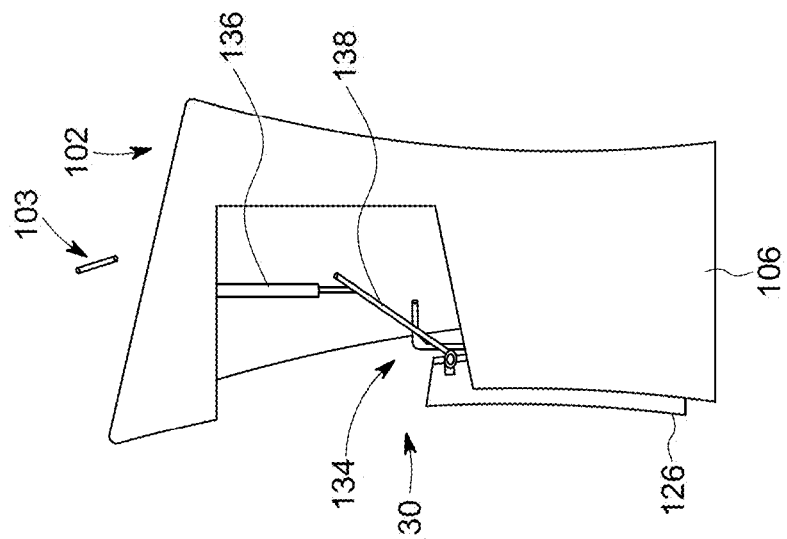
FIG. 8 is a side partial view of the illustrative fascia tissue therapy system of FIG. 1 shown with an access panel in a fully open position.
Figure 7:
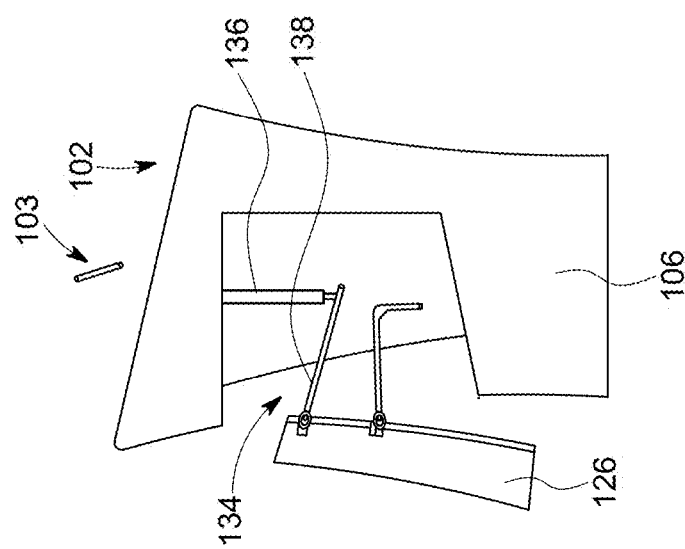
FIG. 7 is a side partial view of the illustrative fascia tissue therapy system of FIG. 1 shown with an access panel in a partially open position.
Figure 6:
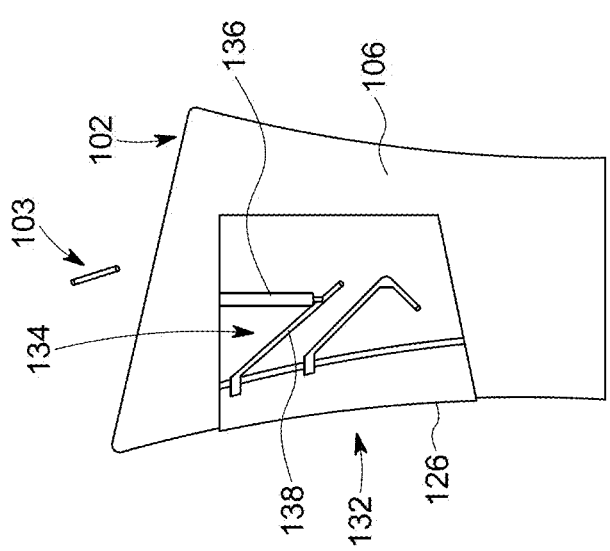
FIG. 6 is a side partial view of the illustrative fascia tissue therapy system of FIG. 1 shown with an access panel in a closed position.

FIGS. 3A-3C show rear, side, and front views, respectively, of the illustrative base station 102 of FIG. 1 are shown. The enclosure 106 of the base station 102 includes an access panel 126 (e.g., door, etc.) coupled to the enclosure 106 along a rear side 128 of the enclosure 106. The access panel 126 is movable between an open position and a closed position to selectively provide access to the interior cavity 108 of the enclosure 106 (as shown in FIG. 5). FIGS. 4-8 show various views of the illustrative base station 102 of FIG. 1 with the access panel 126 in the open position 130 (FIG. 8) and the closed position 132 (FIG. 6). As shown in FIGS. 6-8, the access panel 126 includes a pivot system 134 that allows the access panel 126 to translate away from (e.g., radially away from) and pivot with respect to the enclosure 106. It should be understood that a variety of configurations for opening and closing the access panel 126 may be utilized, including sliding open and close within a concealed wall. The pivot system 134 may include a shock absorber 136 to stabilize the supports 138 for the access panel 126 and facilitate movement between the open position, the closed position, and/or an intermediate position between the open and closed positions. In some embodiments, the pivot system 134 may be configured to automatically reposition the access panel 126 in response to user commands from the computing system 103.

Figure 10:
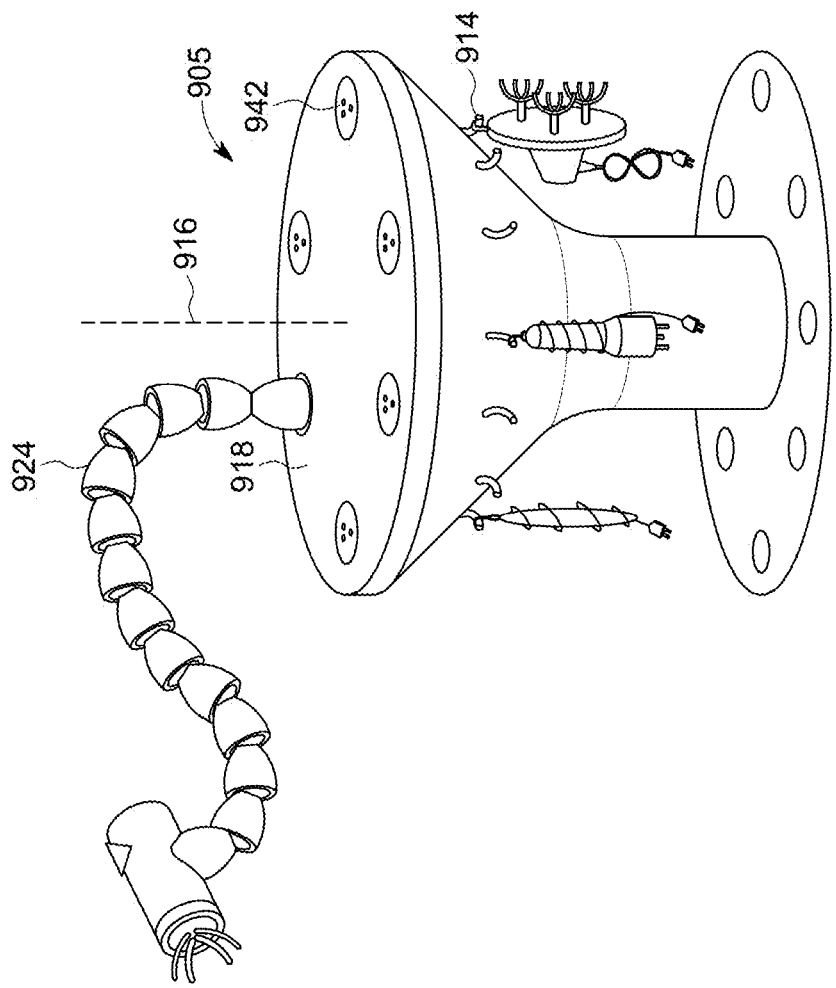
FIG. 10 is an illustration of a front isometric view of another illustrative carousel for a fascia tissue therapy system.
Figure 9:
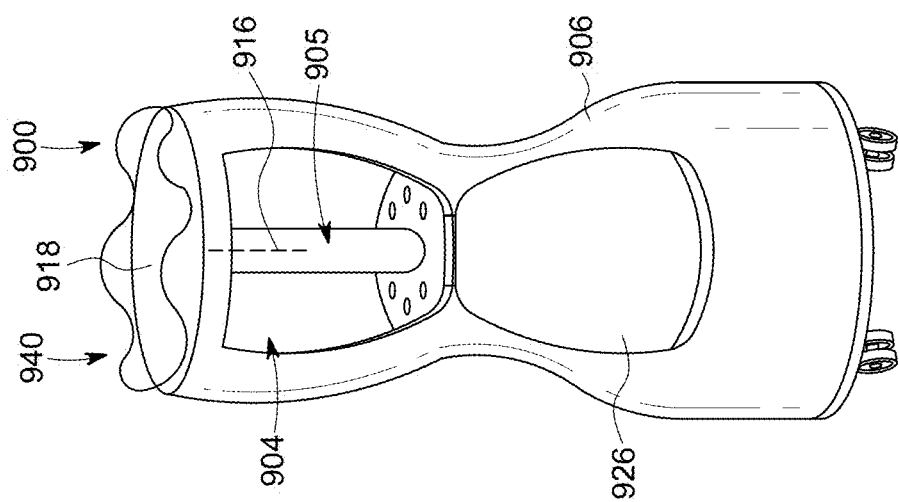
FIG. 9 is an illustration of a front isometric view of another illustrative fascia tissue therapy system.
Figure 12:
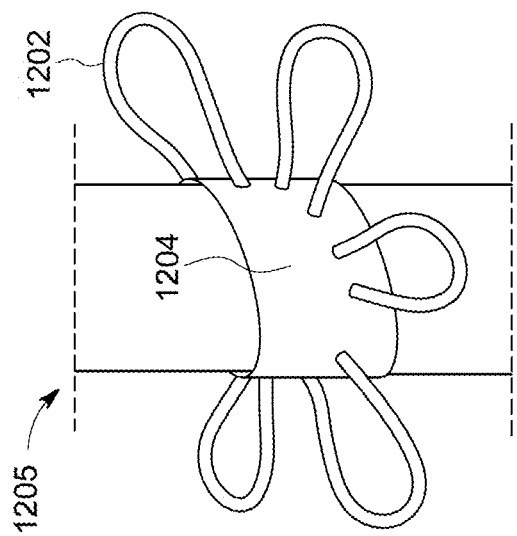
FIG. 12 is an illustration of a front isometric view of another illustrative carousel for a fascia tissue therapy system.
Figure 11:
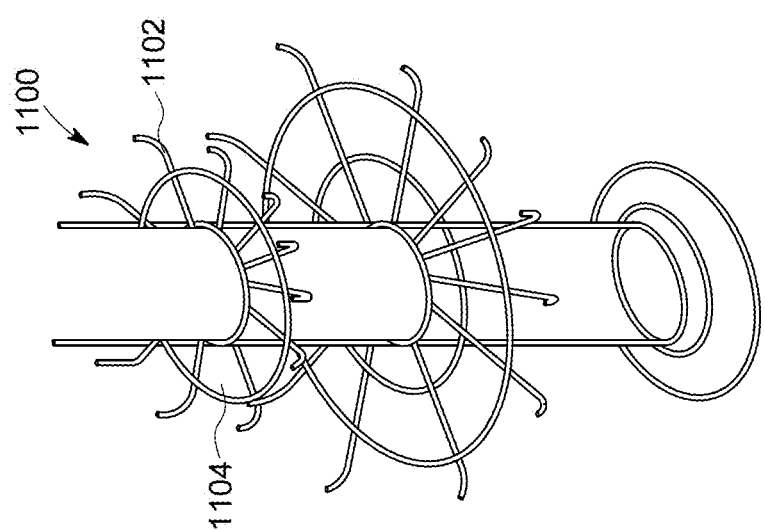
FIG. 11 is an illustration of a front isometric view of an illustrative carousel for a fascia tissue therapy system.
Figure 13:
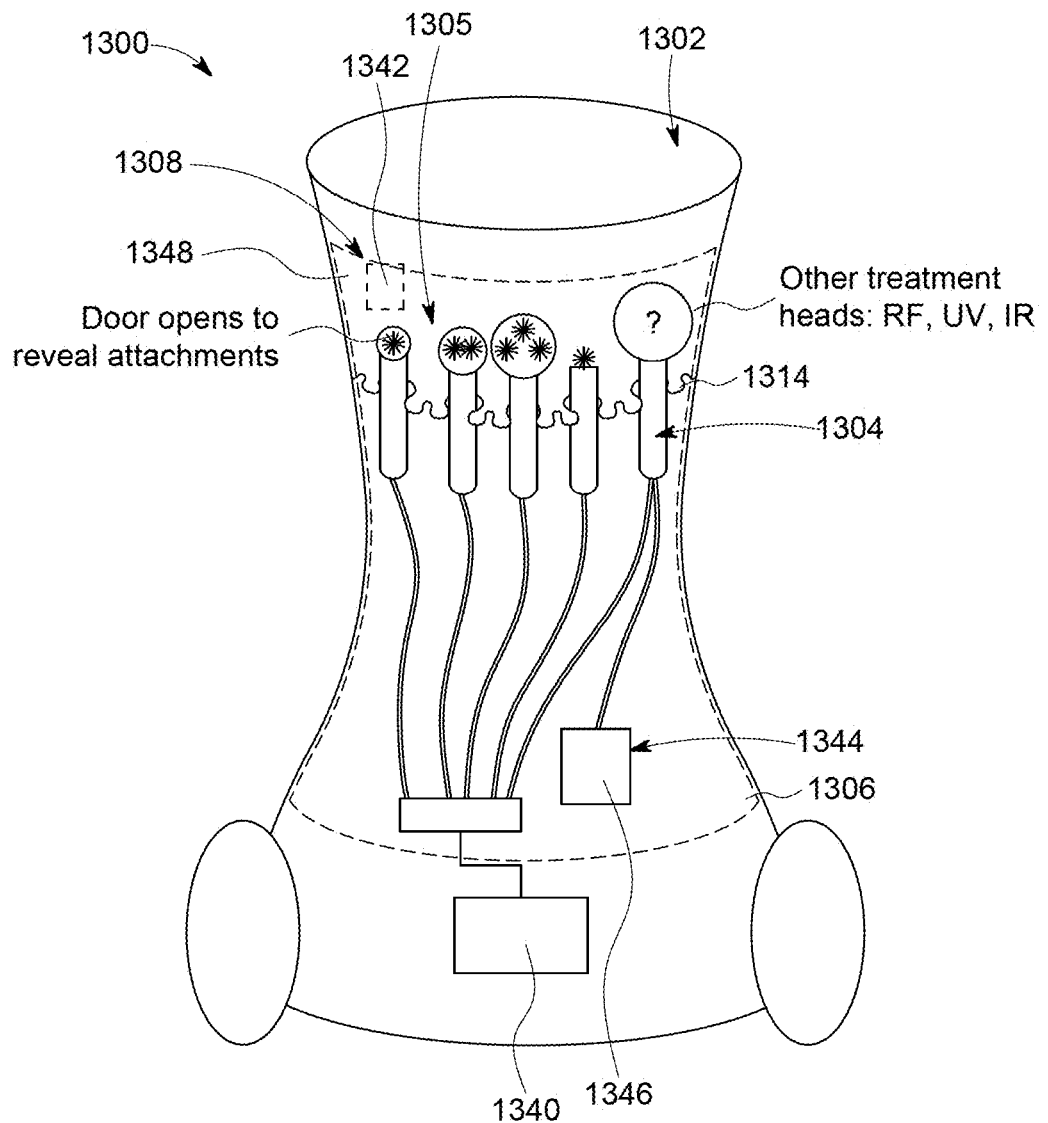
FIG. 13 is an illustration of a rear view of another illustrative fascia tissue therapy system.

In some embodiments, the system 100 (e.g., the base station 102) is structured to store treatment devices, tissue treatment assemblies, and/or tissue treatment elements therein. For example, FIG. 9 shows an illustration of a rear perspective view of another illustrative fascia tissue therapy system 900 that includes a rotating carousel 905. As shown in FIG. 9, the rotating carousel 905 is disposed within the interior cavity 904 of the enclosure 906 and is rotatably coupled to the enclosure 906 (e.g., is rotatable within the enclosure 906). The access panel 926 is moveably coupled to the enclosure 906 and can rotate away from the enclosure 906 to provide access to the carousel 905. As shown in FIG. 10, the carousel 905 may include a plurality of mounts 914 arranged circumferentially (e.g., along a circumferential direction) about a rotational axis 916 of the carousel 905. The mounts 914 are engageable with the treatment device, tissue treatment assemblies, tissue treatment element, and/or other add-ons for the therapy system 900. The mounts 914 may include hangers, magnets, and/or other detachable couplings to support any add-on equipment for the system 900. For example, FIG. 11 shows an illustration of a carousel 1100 that includes wire hangers 1102 and shelving 1104 to support various add-ons (e.g., therapy devices, etc.). FIG. 12 shows a carousel 1205 that includes a plurality of loops 1202 extending radially away from a central sleeve 1204. It will be appreciated that the design of the carousel 1205 may be different in other embodiments. For example, FIG. 13 shows an enclosure 1306 of a base station 1302 that includes a straight rack of hangers 1314 that may be rotatably or fixedly coupled to the enclosure 1306. As shown in FIG. 15, the rack of hangers 1314 is arranged along a single row (e.g., a linear row, etc.) within the interior cavity 1308 of the enclosure 1306. Outlet(s) to power source(s) may be disposed within or outside of the enclosure 1306 and be easily accessible to plugs of cables for the treatment devices to be plugged into to draw power for operation thereby. In an embodiment, the outlet(s) may be rotatable on the carousel 1305.

It will be appreciated that different mounts may be used to store different types of equipment within or external to the enclosure. The mounts may be arranged at different positions within the interior cavity and/or along the carousel depending on the type of equipment that the mounts support (e.g., at different axial and/or radial positions along the carousel, etc.). A user may rotate the carousel within the interior cavity and select the piece of equipment that the user would like to use. Beneficially, using a rotatable carousel to store treatment devices and add-ons improves space utilization of the interior cavity.

In the embodiment of FIGS. 9 and 10, the carousel 905 defines an upper wall 918 of the enclosure 906 that is accessible from an upper end 940 of the enclosure 906. The carousel 905 may include a plurality of electrical connectors 942 along the upper wall 918 that are engageable with the tether 924 for the treatment device(s). As such, rotation of the carousel 905 may also rotate external features of the base station 902 and/or enclosure 906 (e.g., the upper wall 918). In other embodiments, as shown in at least FIGS. 1-2 and FIGS. 3A-3C, the position of the electrical connection 146 between the tether 124 and the base station 102 may be different (e.g., the tether 124 may connect to the base station 102 at a lower, rear end of the enclosure 106, etc.).

As shown in FIG. 13, a user may store the treatment device 1304 in the interior cavity 1308 when not in use to improve the overall aesthetic of the system 1300. In some embodiments, the base station 1302 may further include a motor 1340 coupled to the carousel 1305 and structured to rotate the carousel 1305 in response to user commands (e.g., signals from a control interface of the base station, push-button, etc.). In an embodiment, rather than using a carousel 1305, the mounts may be positioned on the walls of the interior of the enclosure 1306.

In some embodiments, the base station also includes a sterilization system 1342 configured to sterilize treatment devices 1304, tissue treatment elements, and/or other equipment. The sterilization system 1342 may include an ultraviolet (UV) light source including one or more UV lights disposed within the interior cavity 1308 and configured to expose or "flood" equipment mounted to the carousel 1302 with UV light for a threshold period after the access panel has been closed (e.g., when the access panel is in a closed position blocking access to the interior cavity 1308). In an embodiment, the UV light may be controlled to be turned ON or OFF by a push-button, controlled to be turned ON or OFF via a user interface of a computing device, automatically turned ON when the system 1300 is not in use (e.g., overnight), or automatically turned ON when the access panel is closed (monitored by a switch, for example). Alternatively, or in combination, the sterilization system 1342 may include a dispensing system 1344 (e.g., nozzle, pump, etc.) disposed within the interior cavity 1308 and configured to distribute a sterilization agent over the equipment placed within a container (e.g., mounted to the floor or wall) of the sterilization system 1342, where a portion of a treatment device 1304 may be placed into the container within the interior cavity 1308 in response to a signal indicating that the access panel has been closed, and/or a signal indicating that treatment has concluded. In some embodiments, the dispensing system 1344 includes a dispensing device that can be used to fully wash the equipment placed into the container and stored within the enclosure 1306. In an embodiment, multiple wash cycles (e.g., a sterilization cycle, a rinse cycle, etc.) may be performed on the effectors and possibly other components.

The dispensing system 1344 may include an interchangeable fluid reservoir 1346 (see FIG. 13) that stores liquids (e.g., sterilizing agents, heat absorbing agents, lubricating agents, etc.) that are used with the therapy system 1300 and from which one or more pumps supply fluid to the dispensing device and/or nozzle(s) of the therapy device(s). The dispensing system 1344 may also be configured to pre-treat surfaces of the effectors and/or therapy devices with lubricants (e.g., oils) or other liquids. The reservoir 1346 may be detachably coupled to the enclosure 1306 and may be replaced when the liquid supply drops below threshold levels. The sterilization system 1342 may further include fans, blowers, and/or heating elements to dry off the tissue treatment devices 1304 at the end of a wash cycle. In other embodiments, the enclosure 1306 may define a second cavity—separate from the storage area of the interior cavity 1308—that is used to sterilize the tissue treatment devices 1304 and other add-on equipment after use. The sterilization system 1342 may be affixed to an inner surface 1348 or structure within the interior cavity 1308. The sterilization system 1342 may have a door positioned on top and/or side of an internal container and/or the enclosure 1306, and enable an operator to place effector(s) within the sterilization system 1342. As previously described, the sterilization system 1342 may include fluid that may be sprayed onto the effector(s) and/or other components placed therein, and automatically perform a sterilization cycle (e.g., spray/soak, rinse, rinse, dry, illuminate with UV lights to disinfect the effort(s)).

Returning to FIG. 1, the computing system 103 (e.g., computing device, etc.) may be configured to monitor and manage treatment sessions of patients by an operator of the therapy system 100, and/or may include a control system configured to control operation of the fascia tissue treatment device(s) 104. The computing system 103 may include a controller having a processor and memory storing software for the system for supporting patient treatments (e.g., different treatment regimens, patient data received from sensors, such as pressure sensor(s), speed sensor, torque sensor, temperature sensor(s), etc., onboard the treatment device 104 and/or the user interface, etc.). The computing system 103 may include a user interface 140 coupled to the base station 102, to receive user commands and display treatment and/or operating information for the therapy system 100. For example, the computing system 103 may include a tablet (e.g., iPad, etc.) and/or another input/output that is detachably coupled to the base station 102.

Figure 14B:
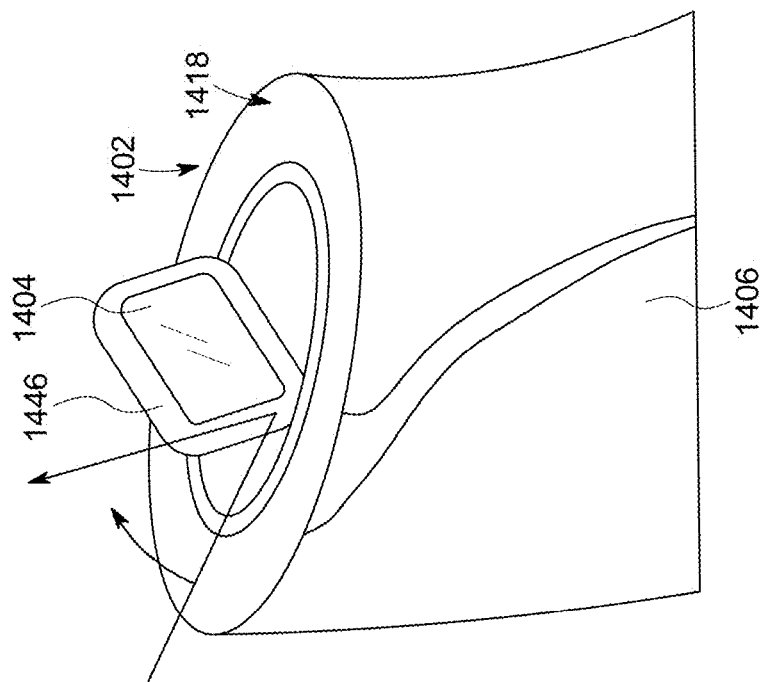
FIG. 14B is another illustration of a side isometric view of the display mount portion of FIG. 14A.
Figure 14A:
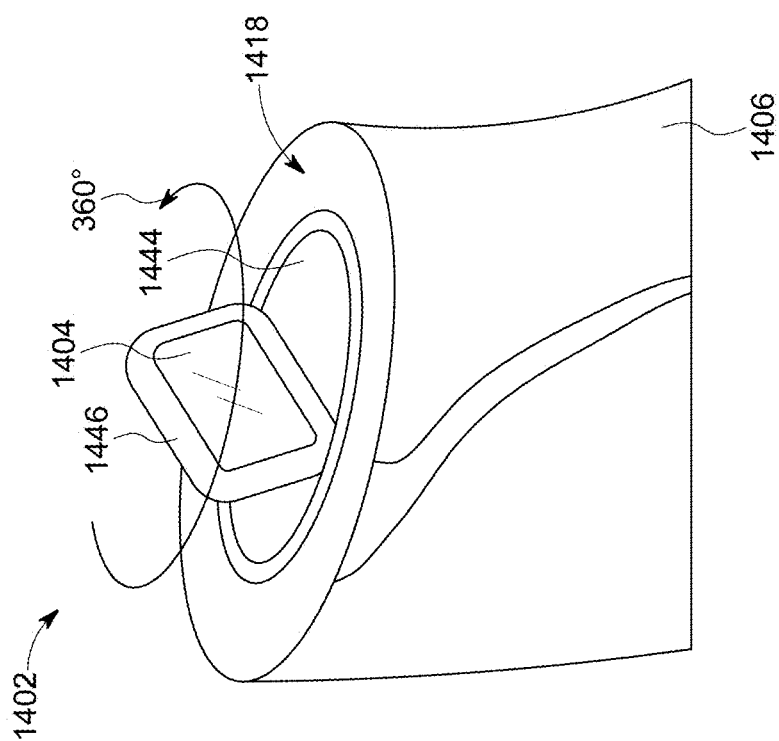
FIG. 14A is an illustration of a side isometric view of a display mount portion of an illustrative fascia tissue therapy system.
Figure 17:
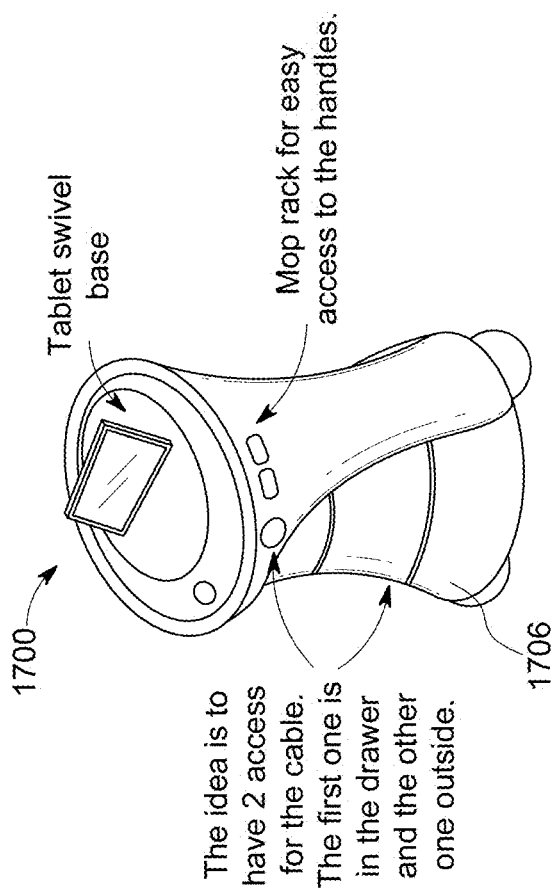
FIG. 17 is an illustration of a front isometric view of yet another illustrative fascia tissue therapy system.
Figure 22:
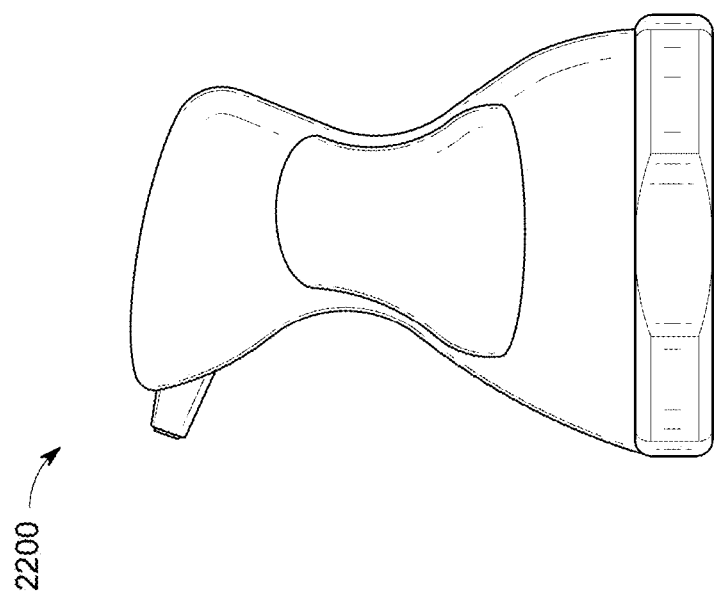
FIG. 22 is an illustration of a side view of another illustrative fascia tissue fitness device.
Figure 21:
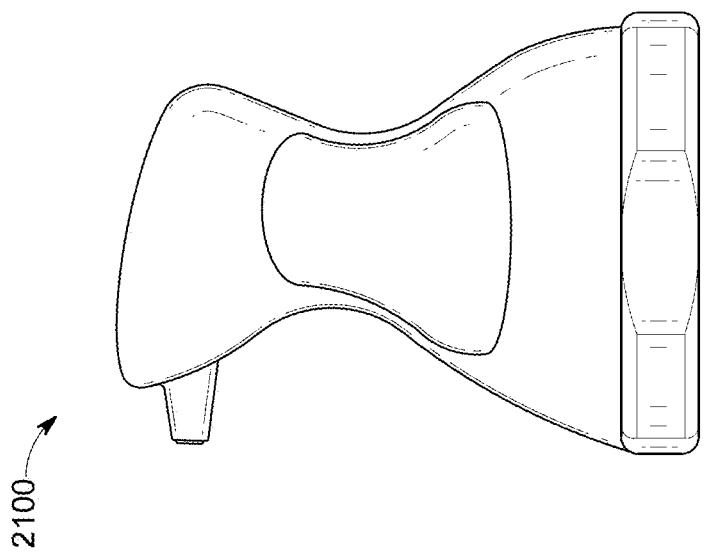
FIG. 21 is an illustration of a side view of illustrative fascia tissue fitness device of FIG. 2.

As further shown in FIG. 1, the tablet may be pivotably and/or rotatably coupled to the base station 102 via a mounting stand 142 that allows the user to reposition the tablet (e.g., a display screen) with respect to the base station 102. In other embodiments, as shown in FIGS. 14A-14B, a user interface 1404 (e.g., a tablet) may be mounted on a swivel 1444 along the upper wall 1418 of the enclosure 1406. The swivel 1444 may allow 360° rotation of the user interface 1404 with respect to the base station 1402. The swivel 1444 may also include a receiver 1446 that engages the user interface 1404 and is structured to tilt relative to the upper wall 1418 of the enclosure 1406 (FIG. 17). The user interface 1404 may be remotely connected (e.g., via Bluetooth, WiFi, etc.) and/or hardwired to the base station 1402 (e.g., via the mounting stand, etc.). In some embodiments, as shown in FIG. 1, the user interface may also include buttons, toggles, and/or another form of user input device 144 disposed on the base station 102 (e.g., enclosure 106) and configured to control certain functionality of the therapy system 100. For example, the user interface 140 may be configured to enable an operator to set certain conditions (e.g., shut off, alarms, alerts, self-cleaning, etc.) on the base station 102 to perform certain functions, such as allowing a user to be notified of certain conditions (e.g., a temperature of power generator being too high, a temperature of the treatment device 104 being too high, a torque of the treatment device 104 being too high, etc.).

In one embodiment, the user interface 140 may be configured to provide treatment guidance to an operator, such as modalities to perform using specific treatment devices 104 and/or effectors for certain durations and at different speeds. The operator may perform the treatment, and the user interface 140 may automatically collect treatment data (e.g., duration of procedure, speeds of effectors, treatment modality, etc.). In one embodiment, the computing system 103 is configured to (i) curate operator sign-in, scheduling of treatment, and collection of patient data (e.g., treatment notes from a clinician, treatment start and end times, etc.), and (ii) guide an operator in applying the treatment device 104 and pre-treatment procedures. The computing system 103 may include interactive software that allows a user to obtain additional information regarding one or more treatment operations (e.g., how to activate a treatment device 104, how to manipulate the treatment device 104 during treatment, etc.). The computing system 103 may also provide video demonstrations to further clarify operation of different aspects of the therapy system 100, as will be further described.

In another embodiment, the computing system 103 is configured to automatically or semi-automatically (e.g., in combination with inputs from a clinician) analyze inputs to develop treatment plans for the patient. The computing system 103 may be configured to define a therapy regimen (e.g., a list of treatments to be performed), and compare pre-treatment and post-treatment results (e.g., historical results over the treatment period), among other automated and non-automated features. In this embodiment, the computing system 103 is also configured to control a treatment device operation to administer treatment and/or to provide feedback to the user and/or patient based on sensor data, as previously described and as will be further described herein.

Figure 15B:
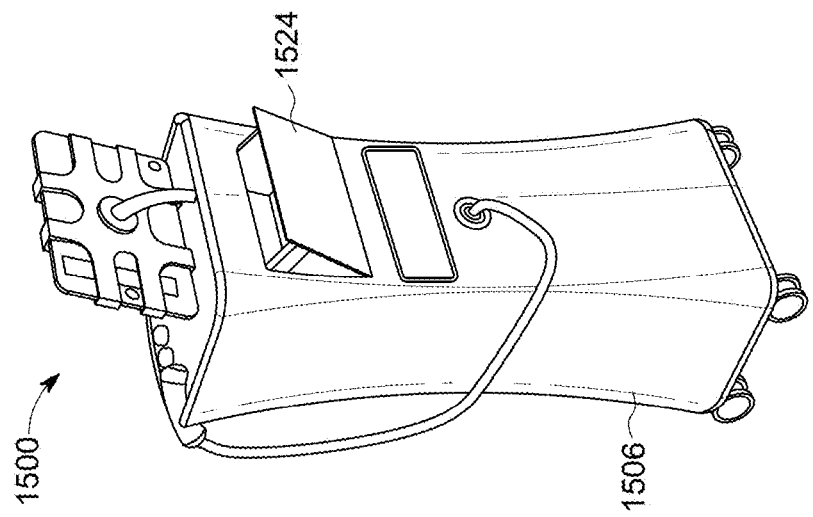
FIG. 15B is a rear view of the illustrative therapy system of FIG. 15A.
Figure 15A:
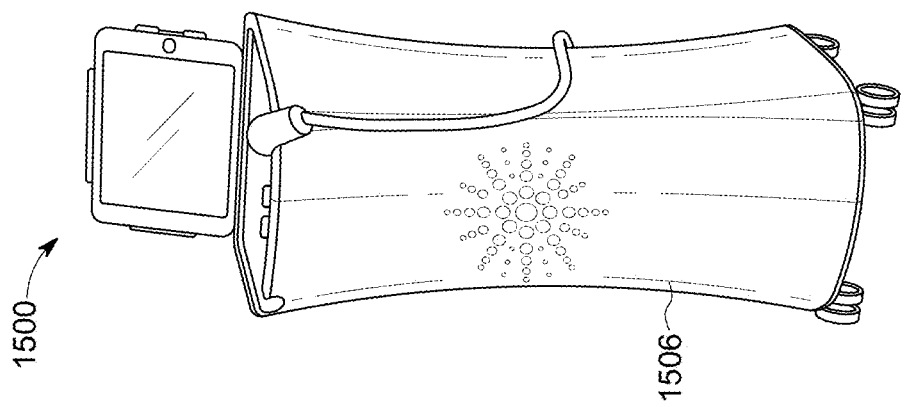
FIG. 15A is an illustration of a front isometric view of another illustrative fascia tissue therapy system.
Figure 18:
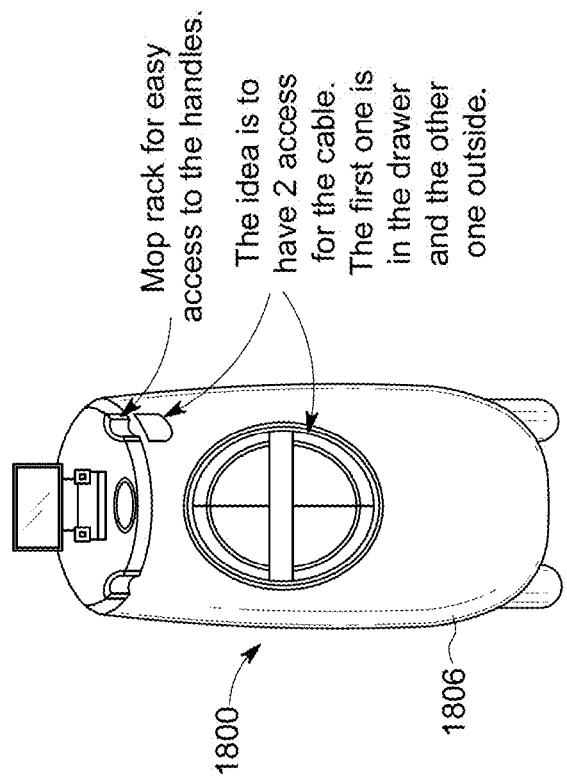
FIG. 18 is an illustration of a front isometric view of yet another illustrative fascia tissue therapy system.

The design of the therapy system described with reference to FIGS. 1-2 and FIGS. 3A-3C should not be considered limiting. Many alternatives and combinations are possible without departing from the inventive principles disclosed herein. For example, FIGS. 15A-15B, FIGS. 16A-16B, and FIGS. 17-20 show various other illustrative embodiments of a base station for a therapy system that include different designs for the enclosure, user interface, access panel, and/or mounts for the fascia tissue treatment devices. For example, FIGS. 15A-15B show a therapy system 1500 having an access door 1524 that pivots away from an enclosure 1506 of the therapy system 1500. FIGS. 16A-16B show a therapy system 1600 having an enclosure 1606 having a profile that is shaped to match the natural contours of a human body (e.g., a frustoconical shape with curved sidewalls). FIGS. 17-20 show various other shapes for an enclosure 1706, 1806, 1906, 2006 of a treatment system 1700, 1800, 1900, 2000.

Figure 23B:
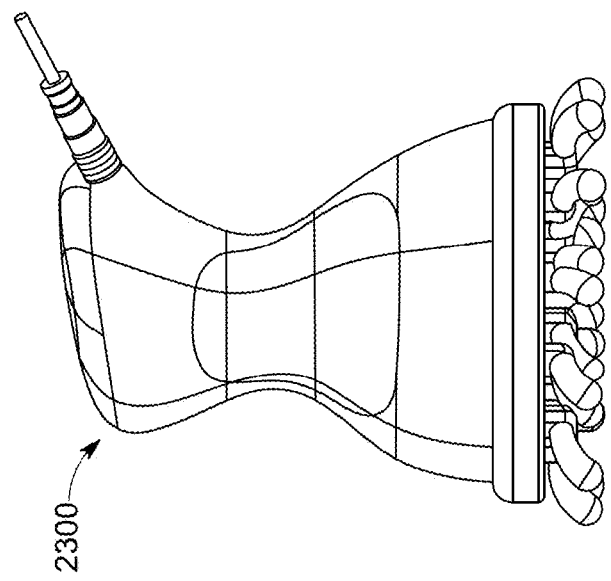
FIGS. 23A-23D are illustrations of different sides of yet another illustrative fascia tissue fitness device.
Figure 23A:
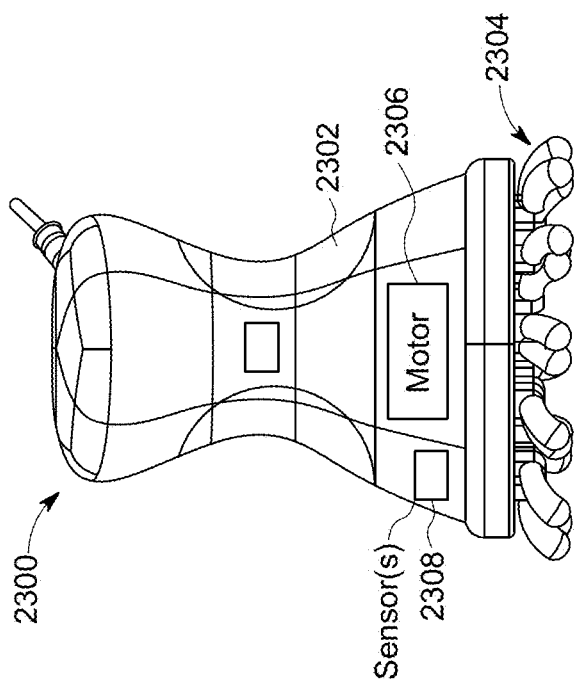
Figure 23D:
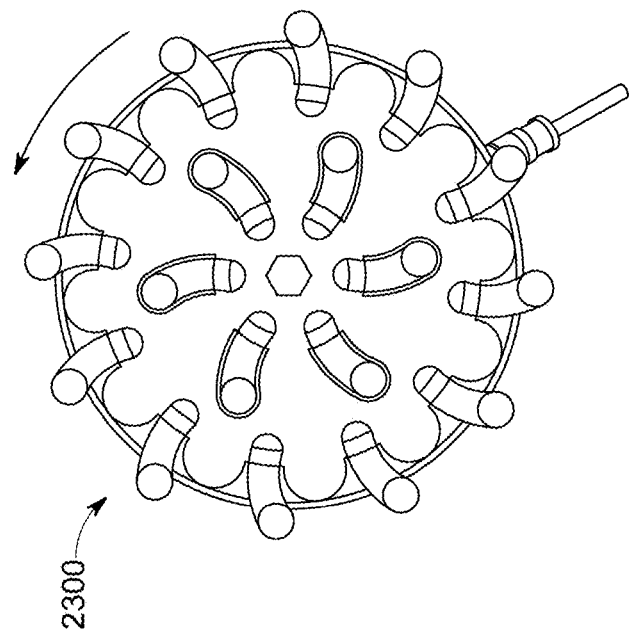
Figure 23C:
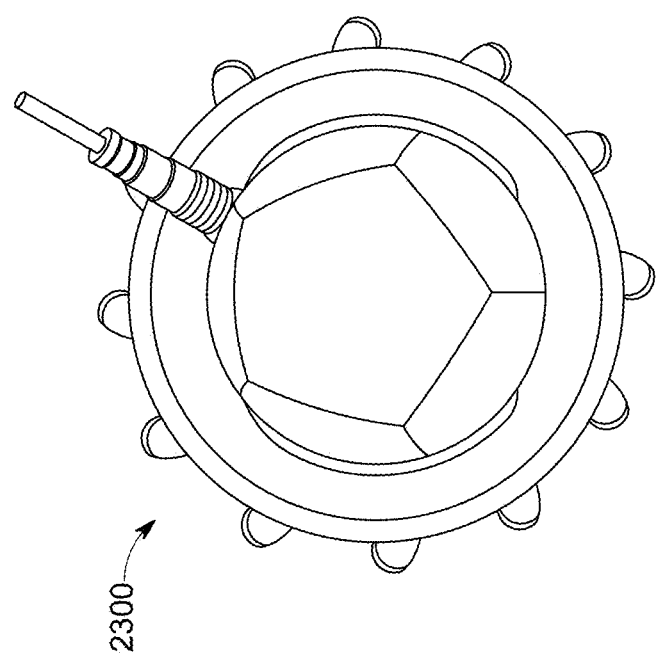
Figure 24B:
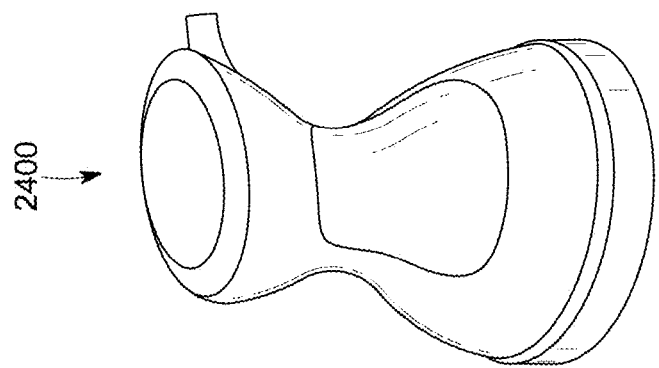
FIGS. 24A-24B are side isometric views of yet another illustrative fascia tissue fitness device.
Figure 24A:
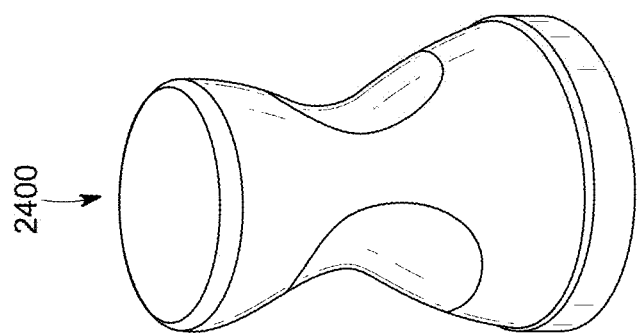

Referring to FIGS. 21-22, FIGS. 23A-23D, and FIGS. 24A-24B various illustrative fascia tissue treatment devices 2100, 2200, 2300, 2400 (e.g., therapy devices, etc.) are shown for use with the fascia tissue therapy system. The treatment devices 2100, 2200, 2300, 2400 (e.g., heads, etc.) are configured to apply a treatment to a user by moving a tissue treatment assembly (e.g., an effector, a tissue treatment head, etc.) along a user's skin. As shown in FIGS. 23A-23B, the treatment device 2300 includes a housing 2302, a tissue treatment assembly 2304 coupled to the housing 2302, and an actuator 2306 configured to power the tissue treatment assembly 2304. The treatment device 2304 may also include at least one sensor 2308 (e.g., pressure, speed, torque, temperature, etc.), a heating element (e.g., IR lighting), a user interface, and/or other electronic equipment.

Figure 25B:
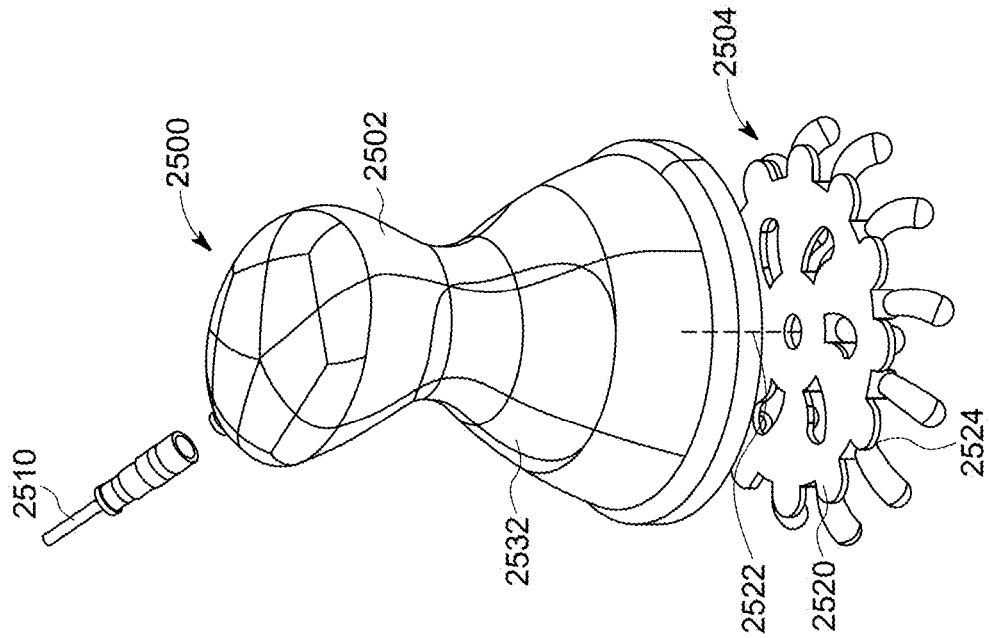
FIG. 25B is an illustration of an exploded view of the illustrative fascia tissue treatment device of FIGS. 23A-23D.
Figure 25A:
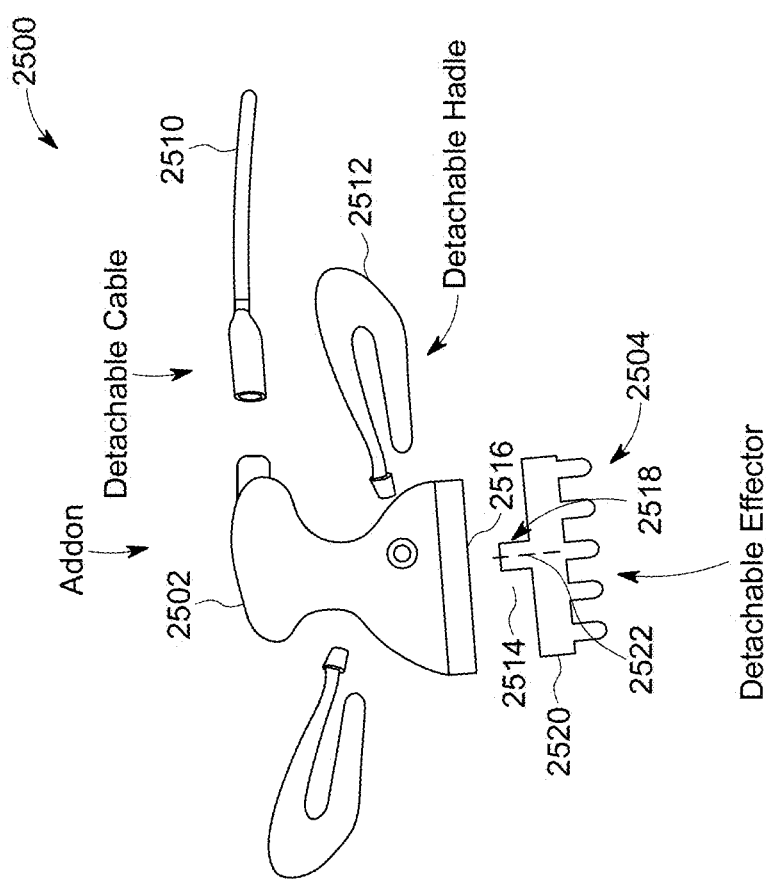
FIG. 25A is an illustration of an exploded view of an illustrative fascia tissue treatment device.

FIGS. 25A-25B show exploded views of an illustrative fascia tissue treatment device 2500 that is similar to the devices of FIGS. 21-22, FIGS. 23A-23D, and FIGS. 24A-24B. As shown in FIG. 25A, the treatment device 2500 is detachably coupled to the tether 2510 of a therapy system that electrically couples the actuator and other onboard electronics to the therapy system. The treatment device 2500 is also detachably coupled to the tissue treatment assembly 2504 and at least one handle 2512 for the treatment device 2500. In this way, different tissue treatment assembly designs may be used with the same treatment device 2500. The treatment device 2500 may include a quick-connect interface 2514, such as a chuck, snap-fit connector, and/or another form of detachable coupling to facilitate removal and replacement of the tissue treatment assembly 2504. The tissue treatment assembly 2504 may couple to a mounting member 2516 (e.g., a center mounting member disposed centrally along an end of a housing 2502 of the treatment device 2500, etc.) of the tissue treatment assembly 2504. For example, the tissue treatment assembly 2504 may include a support member 2518 disposed at a central position on the tissue treatment assembly 2504 (e.g., a panel 2520 of the tissue treatment assembly 2504) that extends axially away from the tissue treatment assembly 2504 (e.g., the panel 2520). In other embodiments, the support member 2518 may be coupled to or otherwise engage the tissue treatment assembly 2504 at an intermediate radial position approximately half-way between a central axis 2522 of the tissue treatment assembly 2504 and an outer perimeter 2524 of the tissue treatment assembly 2504. In yet other embodiments, the treatment device 2500 may be configured to engage the tissue treatment assembly 2504 along an outer perimeter 2524 of the tissue treatment assembly 2504. Still yet, the tissue treatment assembly 2504 may be centrally connected to a motor shaft of the actuator. Engaging the tissue treatment assembly 2504 along an intermediate or outer radial position may reduce torque on the actuator during treatment (due to the smaller moment arm of the tissue treatment assembly 2504), reduce deflection of the tissue treatment assembly 2504 under an applied axial force, and ensure more uniform engagement between the treatment elements of the tissue treatment assembly 2504 and a user's fascia tissue.

Figure 26B:
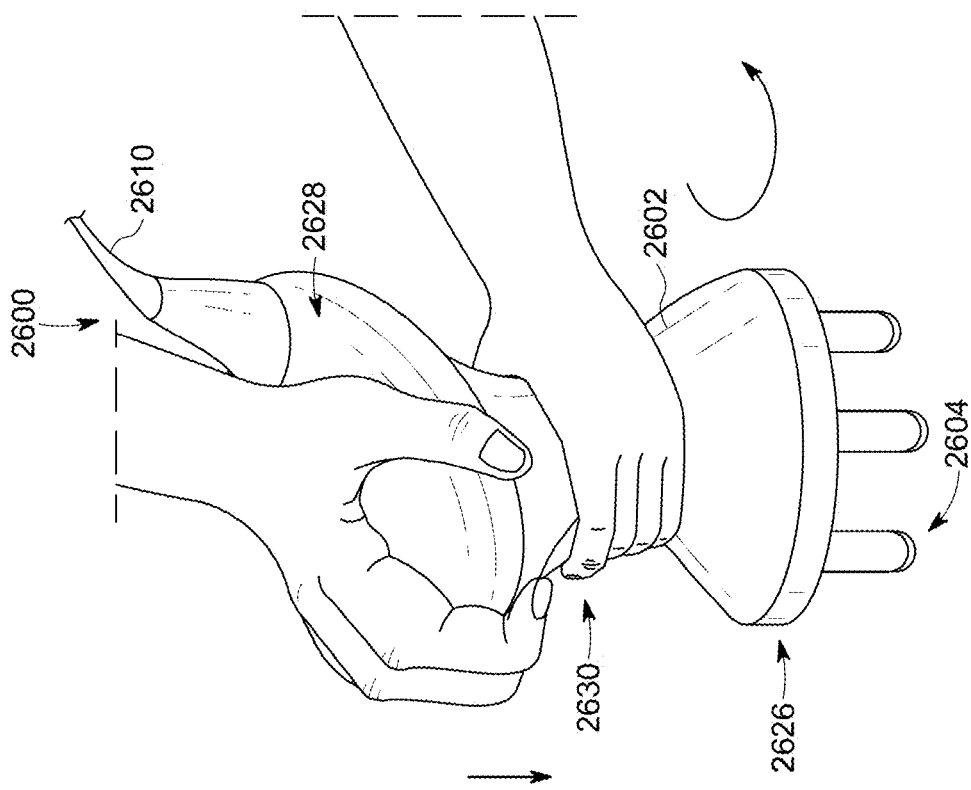
FIG. 26B is another front isometric view of the illustrative fascia tissue treatment device of FIG. 26A.
Figure 26A:
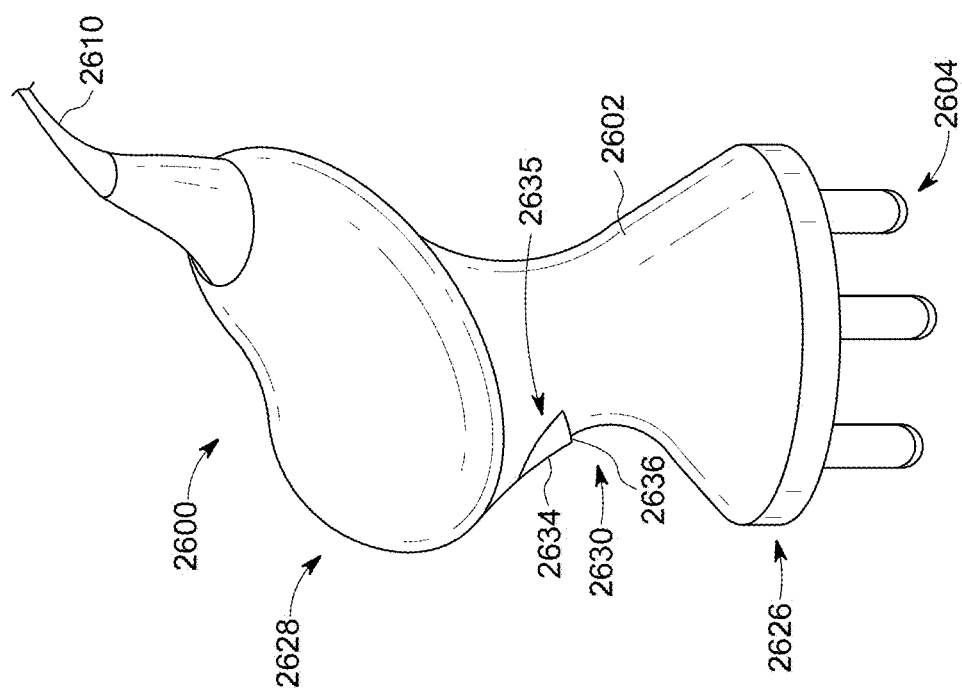
FIG. 26A is an illustration of a front isometric view of another illustrative fascia tissue treatment device.

The treatment device 2500 may be structured for use both with and without the handle 2512 depending if the treatment device 2500 is to be controlled by an operator using one or two hands. The configuration of the treatment device 2500 may, in part, depend on modalities to be performed by the particular treatment device 2500 (e.g., leg and back treatment devices are larger than face and feet treatment devices), weight of the treatment device 2500, speed of the motor, diameter of the tissue treatment assembly 2504, and so on. For example, FIGS. 26A-26B show an example treatment device 2600 that is configured for two-handed operation. As shown, a housing 2602 of the treatment device 2600 includes a first end portion 2626 (e.g., a lower portion, etc.) that is structured to engage with a tissue treatment assembly, a second end portion 2628 (e.g., an upper portion, etc.) spaced axially apart from the first end portion 2626 that is detachably coupled to the tether 2610, and an intermediate portion 2630 (e.g., a central portion, a middle portion, etc.) that extends between the first end portion 2626 and the second end portion 2628. The intermediate portion 2630 may have a smaller cross-section than the first end portion 2626 and the second end portion 2628 such that the first end portion 2626, the second end portion 2628, and the intermediate portion 2630 together form an hourglass shape. As shown in FIG. 26B, the intermediate portion 2630 of the housing 2602 is shaped so that an operator may wrap one of his or her hands around the intermediate portion 2630, which can be used to guide the treatment device 2600 across a patient's skin. As shown in FIG. 25B, the housing 2502 may include pads 2532 that enhance a user's grip on the treatment device 2500. The pads 2532 and/or the housing 2502 may be at least partially formed from a soft silicone material to provide a pleasing velvety feel to the user when manipulating the treatment device 2500. As shown in FIG. 26A, the treatment device 2600 may include a locking mechanism 2634 (e.g., "dead man" switch) that allows the operator to turn the device ON until the locking mechanism 2634 is released. Of course, the treatment device 2600 may include a number of sensors, such as timer, impact switch, timer, temperature, etc., that, if any of the sensors detects a problem (e.g., treatment device is dropped), then the treatment device 2600 may automatically be turned OFF.

As shown in FIG. 26A, the therapy device may also include a user interface 2635 configured to control operation of the actuator and tissue treatment assembly 2604. In one embodiment, the treatment device 2600 may have a switch 2636 (e.g., a trigger) that causes an actuator (e.g., motor) to turn ON. Alternatively, or in combination, a speed of the actuator(s) may be controlled by the switch 2636 that duals as a speed control. Alternatively, a speed controller (e.g., knob or selector on the treatment device 2600) on the treatment device 2600 may enable the operator to change speed of the actuator. If the user interface 2635 operates to control the therapy or treatment device 2600, then speed control may be established on the user interface 2635. Still yet, if the treatment is programmed into the user interface 2635, then speed profiles for the treatment may be established thereon so that the operator can use the pre-programmed speed or may override.

In an embodiment, the switch 2636 (e.g., trigger, button, etc.) is disposed along the intermediate portion 2630 that controls activation of the actuator. In other embodiments, the switch 2636 may also be structured to allow a user to control the speed and/or other functionality of the treatment device 2600. For example, the user interface 2635 on the treatment device 2600 and/or base station may also include a setting selector that allows a user to manually adjust operational limits, effector stiffness, and/or other control parameters for the treatment device 2600. In some embodiments, the treatment device 2600 may also include an auto shut-off switch and/or "dead man's" switch (e.g., the locking mechanism 2634) that deactivates and/or locks the actuator in the event a rapid shut down is required. In some embodiments, the dead man's switch may also be connected to pressure/force, and/or torque measurement sensors within the treatment device 2600 and/or tissue treatment assembly to automatically shut down the system when certain threshold values are satisfied (e.g., when the pressure and/or torque exceeds threshold values).

Figure 27:
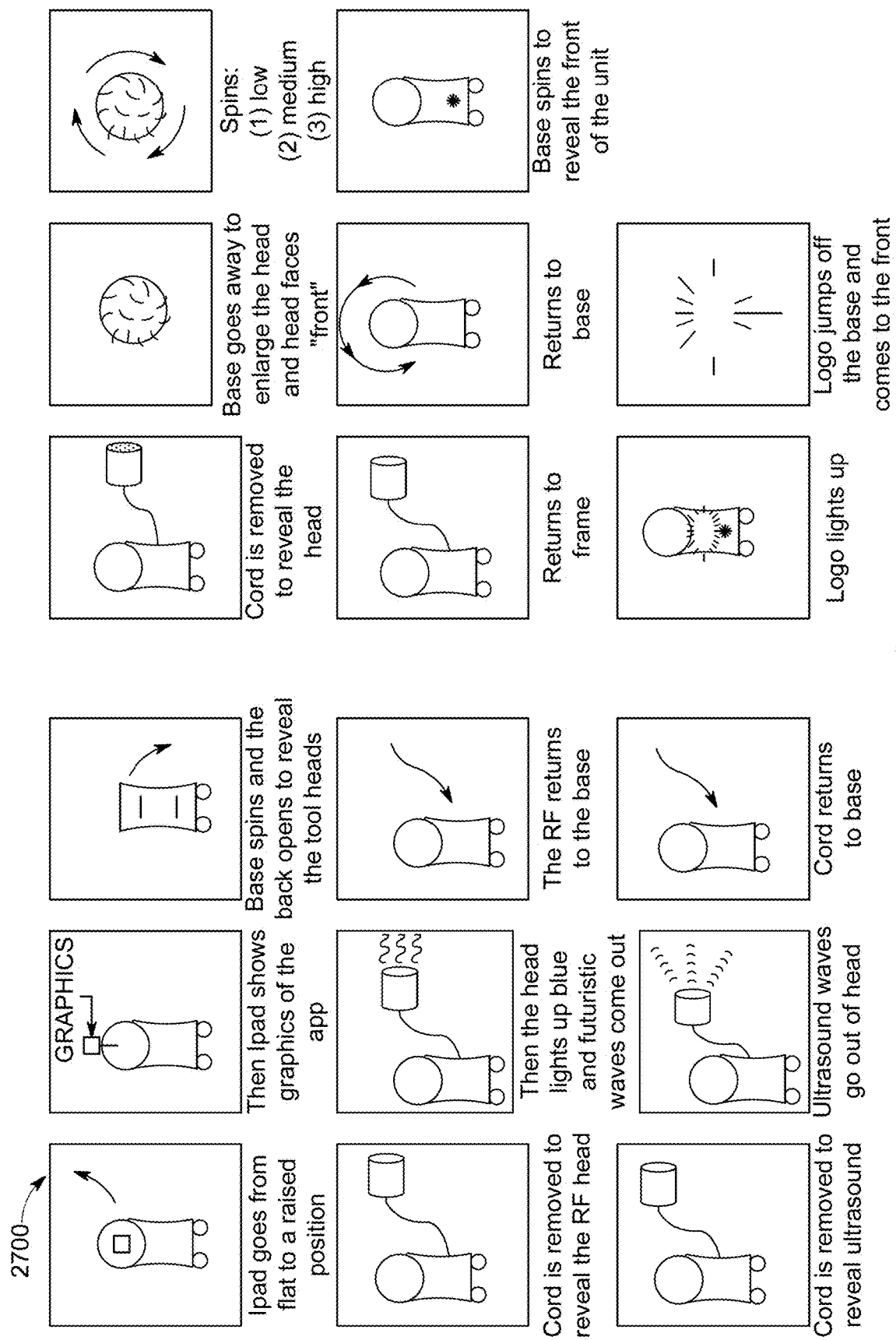
FIG. 27 is an illustration of a storyboard of a video demonstration for using a therapy device.

In some embodiments, the user interface 2635 may also be configured to provide a curated treatment procedure (e.g., modality guidance, etc.) to facilitate user interaction with the treatment device 2600 and to improve treatment effectiveness. For example, the user interface 2635 may provide step-by-step instructions informing the user of where to place the treatment device 2600 and how to hold and manipulate the treatment device 2600 during treatment. For example, the treatment device 2600 may be configured to present a video to a user (e.g., clinician, etc.) to inform the user of each step in the treatment plan, which devices to use, how to use each device. FIG. 27 shows a storyboard 2700 for an example video demonstration of a treatment plan. The demonstration includes informing the user of how to manipulate and operate base station equipment, which therapy devices to use and in what order, and the specific treatment steps to be followed for each device. As shown, the storyboard provides for pre-treatment of fascia tissue, treatment of the fascia tissue, and post-treatment. It should be understood that more specific detail showing differences for different modalities may be provided. For example, pre-treatment of a leg or torso with more muscle mass or fat content may be different than pre-treatment of a face or scalp with less muscle mass and fat content. A treatment plan may start with fascia tissue that is closer to the skin and then deeper tissue treatments may occur over time to gradually work towards restructuring fascia tissue that is deeper. Imaging (e.g., ultrasound imaging) may be used as "feedback" to an operator and/or the system, if so configured, to see how treatments are progressively restructuring fascia tissue starting from the surface and working deeper. Such treatment plans may, of course, be tailored to specific fascia tissue As shown in FIG. 26B, the second end portion 2628 is shaped so that a user may apply a downward force onto the tissue treatment assembly 2604 and toward a patient's skin, thereby causing the tissue treatment assembly 2604 to rotate while the pressure is being applied during treatment. By applying more pressure, the treatment to fascia tissue that is deeper (e.g., towards an underlying leg bone). The second end portion 2628 may define a planar upper surface that extends at an oblique angle relative to the central axis of the housing 2602. A user may engage their palm with the upper surface to apply a downward force toward the skin during treatment. The angled upper surface may improve ergonomics of the treatment device 2600 and allow a user to maintain pressure on the tissue over a longer period of time before becoming tired. It will be appreciated that the shape of the housing 2602 may be different in other embodiments.

In an embodiment, one or more feedback mechanisms may be included in the treatment device 2600 that enables feedback to be given to the operator. For example, lights for illumination, speaker for audible, vibration element for tactile feedback may be provided, where the feedback may be feedback for temperature (of the motor), high current draw (representing high torque (e.g., using current sensor)), treatment cycle start/end (using clock or motion sensor), force being applied is too low or too high (using one or more pressure sensor(s), etc.).

Figure 28:
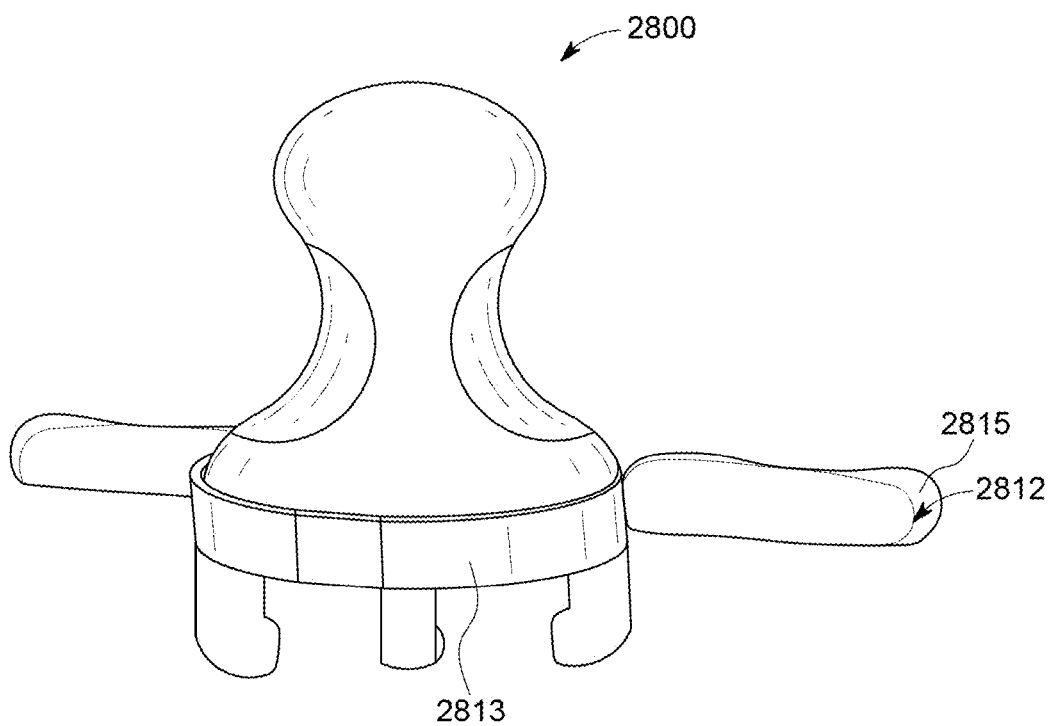
FIG. 28 is an illustration of a front isometric view of yet another fascia tissue treatment device.
Figure 29:
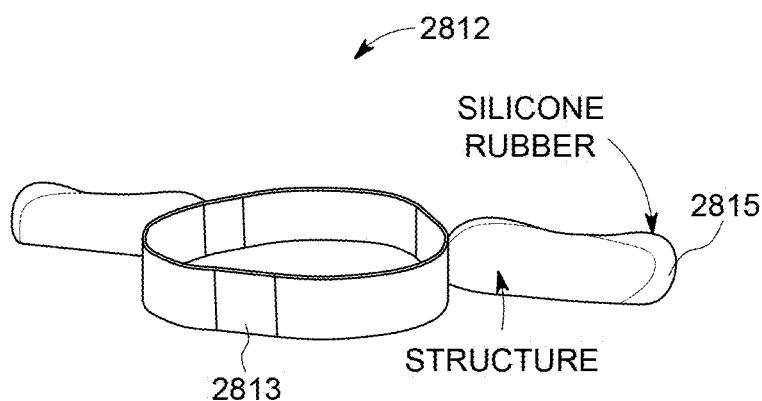
FIG. 29 is an illustration of a front isometric view of a handle for a fascia tissue treatment device.
Figure 30:
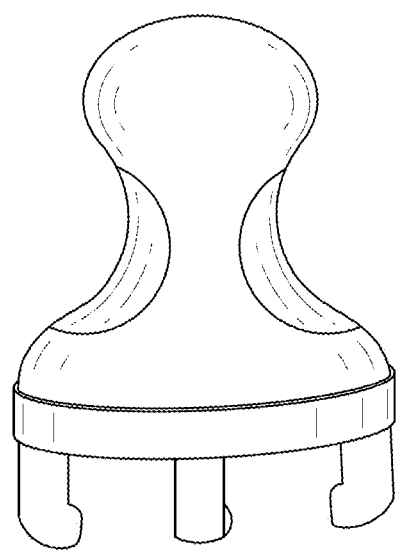
FIG. 30 is a front view of the fascia tissue treatment device of FIG. 28.
Figure 31:
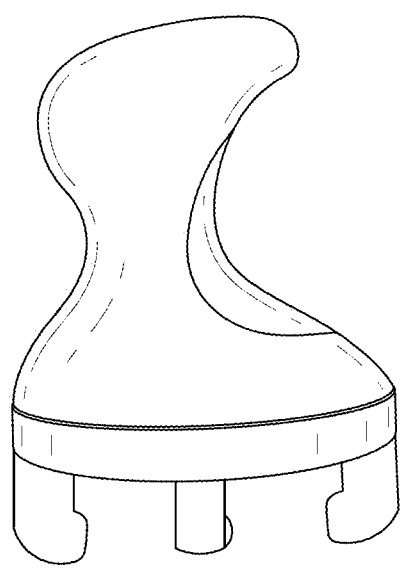
FIG. 31 is a side view of the fascia tissue treatment device of FIG. 28.

Referring to FIG. 28, another illustrative treatment device 2800 (e.g., therapy device, etc.) is shown that includes a removable handle 2812. The removable handle 2812 may be removable from handles of a structural holster or strap 2813, where the handles and/or strap 2813 may be formed of or include silicone rubber (or any other material). The handle 2812 may be used when using the treatment device 2800 to treat elongated body areas such as a patient's legs and back, while reducing stress to a user's hands in applying force to the treatment device 2800. The handles and/or a strap 2813 may engage an end portion (e.g., a lower portion, etc.) of the housing of the treatment device 2800, proximate to the tissue treatment assembly, or any other location of the housing. As shown in FIG. 29, the handle 2812 may be formed with the strap 2813 or holster that engages with a second end portion of the housing to couple the handle 2812 to the housing. In other embodiments (as shown in FIGS. 37-40), the handle 2812 may engage with another portion of the housing away from the tissue treatment assembly (e.g., the intermediate portion of the housing, a first end portion of the housing opposite from the second end portion, etc.). The strap 2813 may mount to the treatment device 2800 via a snap-fit connection, a fastener, and/or other detachably coupling. As shown in FIG. 29, the handle 2812 also includes two posts 2815 that are coupled to the strap 2813 and extend radially away from the strap 2813. The posts 2815 may be substantially cylindrical rods made from silicone rubber or another soft, yet suitably stiff material that a user can interact with to manipulate the position of the treatment device 2800 and force applied to the skin during treatment. As shown in FIG. 30 and FIG. 31, the handles may be separated from the treatment device 2800 depending on the desired treatment application, and/or to facilitate treatment of curved body areas such as the knee, neck, and others.

Referring again to FIGS. 28-29, the handles 2812 and strap 2813 may be used during treatment and/or storage of the treatment device 2800. In other words, the handles 2812 and the strap 2813 may be held by an operator treating a patient or may simply be used for storage of the treatment device 2800. If used during treatment, having two handles 2812 enables the operator to apply pressure equally, if desired, to both handles 2812, thereby applying force by the tissue treatment assembly to the patient in an equal manner. The strap 2813 may be configured to engage with the treatment device 2800 in a manner that still allows for a user interface (e.g., electronic display, LEDs, audio, etc.) disposed thereon to provide treatment and/or feedback information to the operator.

Figure 32:
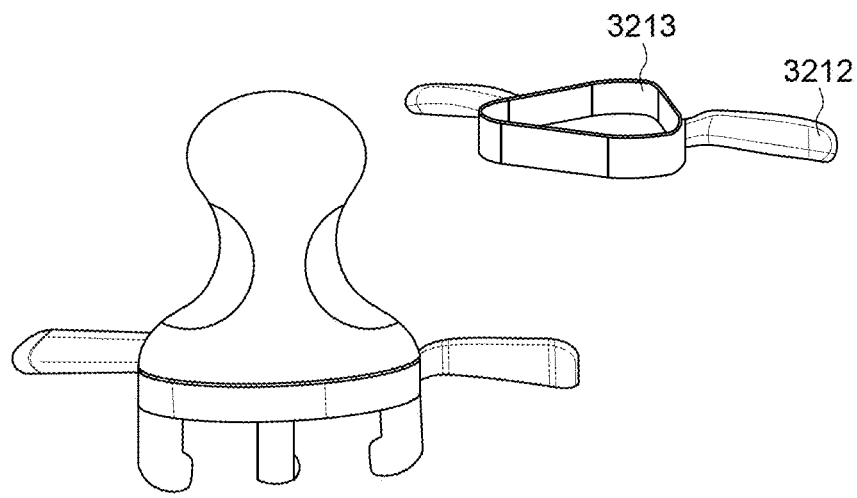
FIGS. 32-35 are illustrations of various illustrative handle designs for a fascia tissue treatment device.
Figure 33:
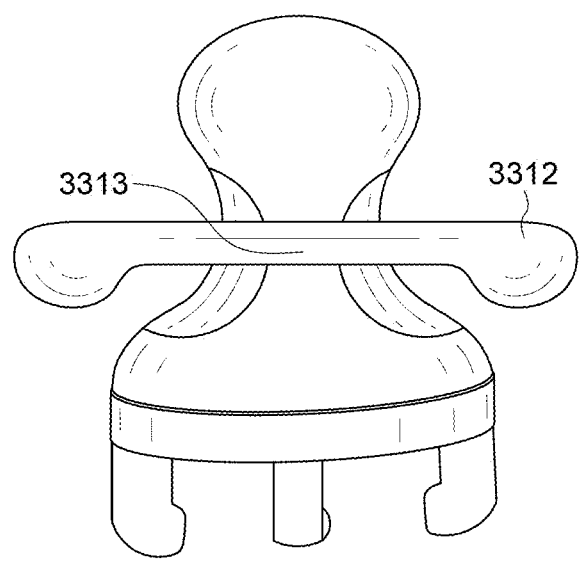
Figure 34:
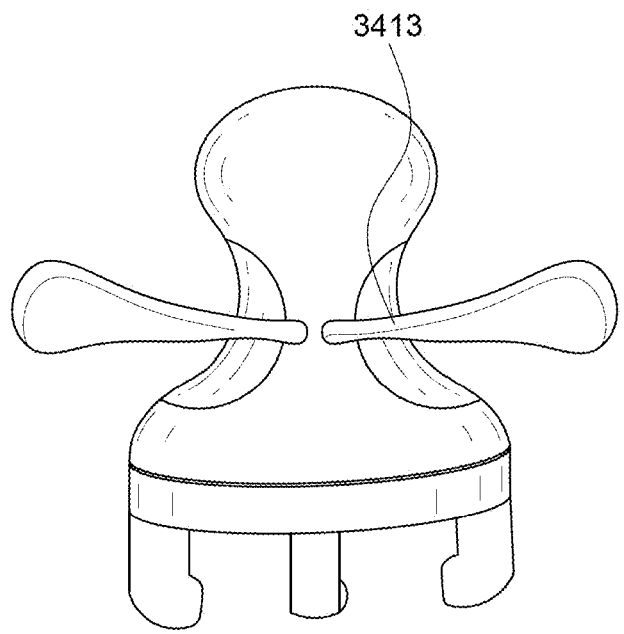
Figure 35:
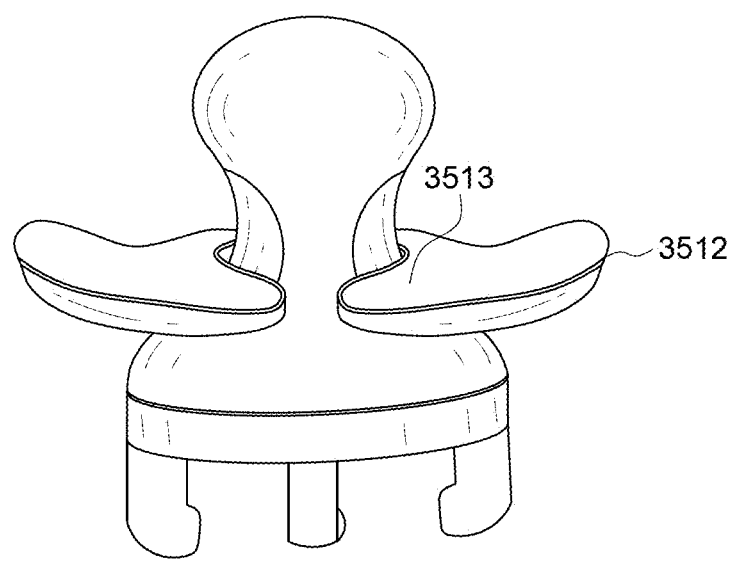

FIGS. 32-35 show various alternative illustrative handle designs for the treatment device 2800 of FIGS. 30-31. As shown in FIGS. 32-33, the handle 3212, 3312 may include a strap 3213, 3313 that circumscribes the housing of the therapy device. In other embodiments (e.g., as shown in FIGS. 34 and 35), the handle 3412, 3512 wraps only partially around the treatment device and includes a slot to facilitate assembly of the handle 3412, 3512 to the treatment device (e.g., by using a flexible strap 3413, 3513 that allows increasing the size of the opening at the slot during assembly to clamp the flexible strap onto the housing). It should be understood that while the handles and/or strap may be flexible, alternative embodiments may have the handles and/or strap be rigid (i.e., not easily bent). Rather than the handles and strap being added, a housing of the therapy device may have handles formed therewith and the handles may be monolithic with the material of the housing of the therapy device.

The design of the housing for the treatment device may be different in various embodiments. For example, FIGS. 36-37 show an illustrative treatment device 3600 that includes a housing having a lower, disk-shaped portion 3602 and an upper, conically-shaped portion 3604 that extends axially away from an upper surface of the lower, disk-shaped portion 3602. As shown in FIG. 36, a user may press against an upper surface of the disk-shaped portion 3602 to facilitate treatment of large body areas such as a patient's back or legs. As shown in FIG. 37, the user may engage with the conically-shaped portion 3604 for finer control and movement of the treatment device 3600.

Figure 38:
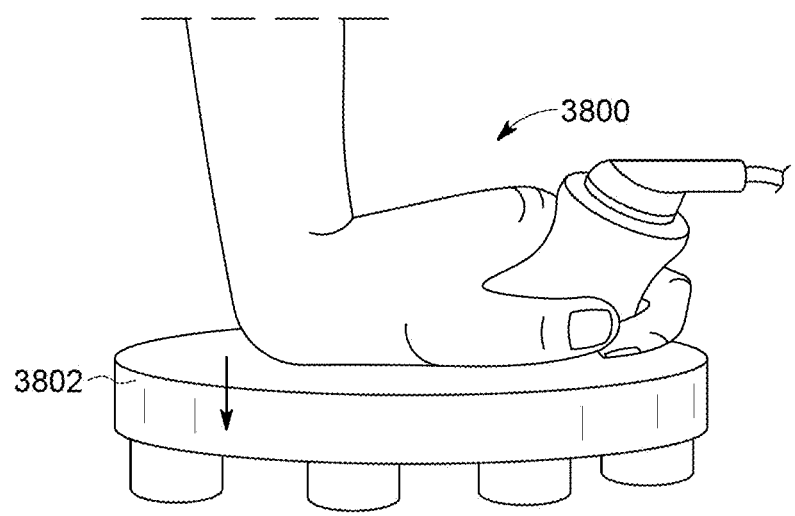
FIG. 38 is an illustration of a side isometric view of yet another illustrative fascia tissue treatment device.

FIG. 38 shows yet another illustrative treatment device 3800 (e.g., a therapy device, etc.). The treatment device 3800 includes a housing design that is similar to the housing of the treatment device 3600 of FIGS. 36-37, but that has a disk-shaped portion 3802 with a smaller cross-section to facilitate single-handed manipulation or use for treatment of body areas where increased maneuverability of the treatment device 3800 is beneficial to the operator.

Figure 39:
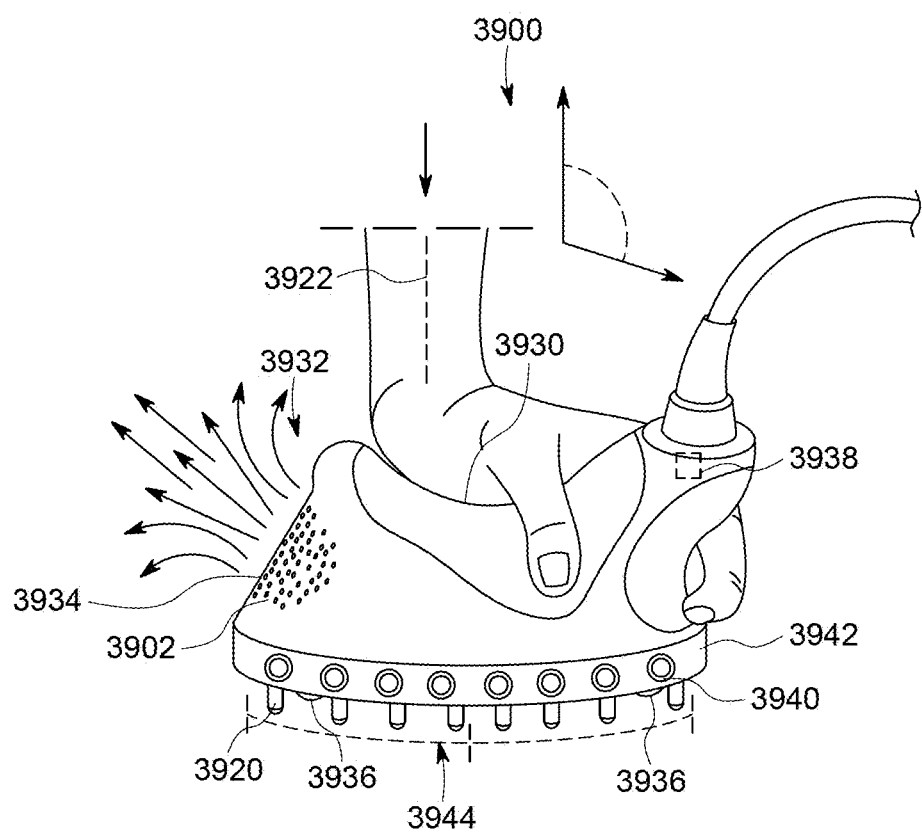
FIG. 39 is an illustration of a side isometric view of yet another illustrative fascia tissue treatment device.

FIG. 39 shows yet another illustrative tissue treatment device 3900 (e.g., a therapy device, etc.). The treatment device 3900 includes a saddle-shaped housing 3902 defining a saddle 3930 that is designed to allow an operator to wrap his or her hand around the top of the treatment device 3900 to both apply vertical and/or angular force and manipulate a position of the treatment device 3900. The housing 3902 may be shaped such that a central axis 3922 of the housing 3902 is approximately aligned with a user's forearm when the operator's hand is wrapped around the saddle 3930 which, in one embodiment, centers any downward force applied to the housing 3902 during use. The saddle 3930 is also shaped to accommodate the natural angle of a user's wrist to reduce strain on the wrist during use.

Figure 44:
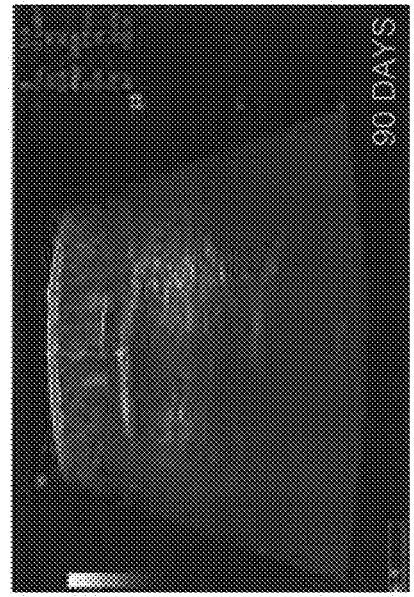
Figure 41:
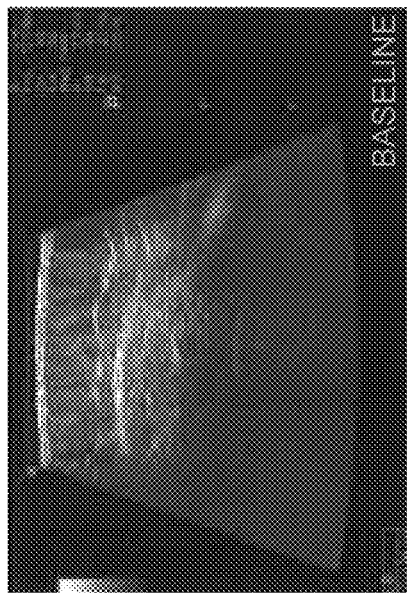
Figure 43:
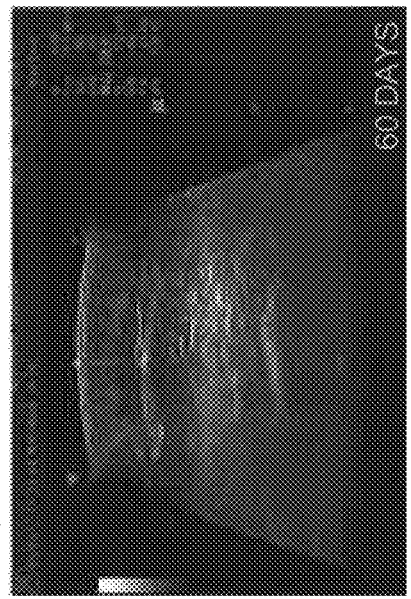

As shown in FIG. 39, the treatment device 3900 may include various add-ons to facilitate monitoring and diagnoses of damaged and/or abnormal fascia tissue, improve manipulation and restoration of fascia tissue, and to reduce the risk of damage to the treatment device 3900 during operation. For example, the treatment device 3900 in FIG. 39 may include a cooling system 3932 that is structured to cool the actuator and/or other electronic components contained within the housing 3902 during treatment. The cooling system 3932 may include a fan and/or blower disposed within the housing 3902 that forces air across the actuator to exit through an exhaust port in the housing 3932 (shown as rear exhaust port 3934 in FIG. 44A). In other embodiments, the treatment device 3900 may include another form of cooling (e.g., liquid cooling) to cool internal components. Hydraulic or other cooling techniques may also be possible. As previously described, a direct drive motor may be utilized to reduce the amount of heat produced by the actuator/motor.

The treatment device 3900 may also include at least one sensor 3936 (e.g., force sensor configured to generate sensor data indicative of a force applied to the sensor, etc.) for monitoring device operations and a transceiver 3938 (e.g., WiFi, Bluetooth, etc.) for communicating sensor data with the controller and/or other networked systems. For example, the treatment device 3900 may include at least one pressure sensor structured to measure a force applied to portions of the tissue treatment assembly (e.g., the effector, etc.), between the tissue treatment assembly and a patient's skin. In at least one embodiment, the treatment device 3900 includes multiple pressure sensors located in different areas or quadrants of the tissue treatment assembly (e.g., at different circumferential and/or axial positions along a panel (e.g., an effector panel, etc.) of the tissue treatment assembly as shown in FIG. 39, at equal intervals across the panel, at a location of each tissue treatment element along the panel, etc.).

The pressure/force sensors may be configured to provide feedback to the user via a user interface of the computing device and/or treatment device 3900 to indicate the measured pressure at the location of each pressure sensor (e.g., via a user interface of the treatment device 3900, or via the user interface on the base station). For example, the treatment device 3900 in FIG. 39 may include multiple indicator lights 3940 disposed along an outer perimeter 3942 of the housing 3902 and facing radially away from or vertical from the housing 3902. In other embodiments, the location of the indicator lights 3940 on the treatment device 3900 may be different. For example, the lights may be disposed on an upper wall of the treatment device, as shown in FIG. 37 (e.g., indicator light 3640). The indicator lights 3940 may be configured to provide an indication of the actual force and/or pressure being applied to the tissue treatment assembly (or a portion of a panel of the tissue treatment assembly) relative to a target force and/or pressure for treatment. For example, as shown in FIG. 39, the treatment device 3900 may include a plurality of sensors 3936 configured to measure a force applied to quadrants 3944 of a panel 3920 of the tissue treatment assembly.

A controller (e.g., at the transceiver 3938, etc.) may be communicably coupled to the sensors 3936 and may be configured to determine forces being applied to the quadrants 3944 of the panel 3920 while the actuator is in an ON state based on sensor data from the sensors 3936. The indicator lights 3940 in a first circumferential quadrant of the treatment device 3900 may indicate whether the pressure and/or force applied in a nearest quadrant 3944 of the panel 3920 is less than a target pressure and/or force based on a color of the lights (e.g., red, yellow, green, blue, etc.), an amount of flashing, and/or other visual indication. In an embodiment, if a target range of forces (i.e., low force threshold and high force threshold) is established for a particular modality or treatment, then in the event that force (e.g., force in a quadrant of the effector) is sensed to be too low, then lights (e.g., LEDs) may be illuminated to be one color (e.g., blue) and if sensed to be too high, then lights may be illuminated to be in another color (e.g., red). If the pressure is sensed to be within range of the desired treatment levels, then another color (e.g., green) may be displayed by the indicator lights 3940. If sensors 3936 configured in quadrants 3944 are used, then the feedback (e.g., lights) may be displayed in relation to each pressure measured in the quadrants 3944 associated with the sensors 3936 in the respective quadrants 3944. Other color schemes may be utilized, as well. Moreover, the pressure sensor feedback signals may be collected by the user interface and stored thereon, thereby enabling the user interface or another computing device to correlate pressure, therapy devices, operator, etc. with fascia tissue restructuring progress, for example.

The treatment device 3900 may also include a speaker to provide audible and/or tactile notification of the applied vs. desired level of pressure and/or force to a user. In some embodiments, the sensors 3936 (e.g., force and/or pressure sensors, etc.) may also be used to determine an average pressure across the tissue treatment assembly (e.g., by averaging measurements from each sensor 3936), a peak pressure across the tissue treatment assembly, and/or to facilitate calibration of the treatment device 3900 (e.g., to facilitate adjustment of an angle of the tissue treatment assembly relative to the housing 3902 of the treatment device 3900 after a new tissue treatment assembly has been installed). If, for example, pressure is too low, a change of an audible signal (e.g., Geiger counter tones, frequency, pitch, and/or volume of an audible signal, etc.) or a notification signal (e.g., tone, beep, etc.) may be produced.

Figure 40A:
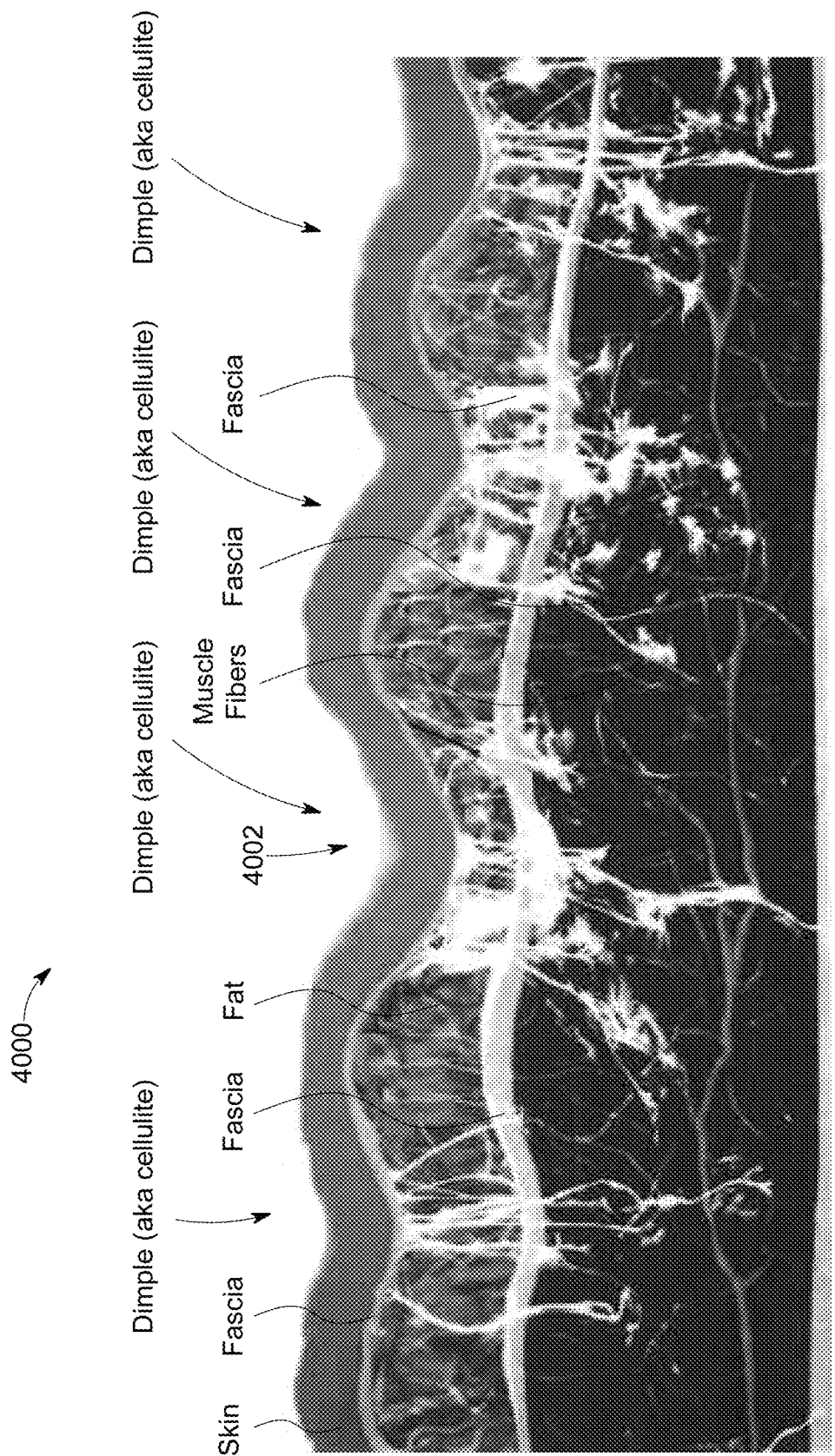
FIG. 40A is an illustration of a cross-sectional view of illustrative fascia tissue layers.

The tissue treatment device 3900 may also include other types of sensors and/or transducers to facilitate assessment of fascia tissue abnormalities prior to, or during, treatment. Examples of fascia tissue layers 4000 and damage is shown in FIG. 40A. Outer and inner structural fascia tissue layers (thin layer beneath the top skin surface layer) are shown to separate skin (top surface layer), subcutaneous fat (beneath the top outer structural fascia tissue layer), and muscle (layer below the subcutaneous fat later) layers. Also shown are inter-structural fascia tissue fibers that extend between the structural tissue layers. Problem areas occur in regions of high fascia tissue density of the inter-structural fascia tissue fibers, which may also be described as adhesions of the fascia tissue. As shown, pockets/dimples 4002 (commonly referred to as cellulite) are formed on the skin surface as a result of the adhesions of the inter-structural fascia tissue fibers. While skin aesthetics may result from adhesions of the fascia tissue, more health-related problems may also result. Such health-related issue may include pinched nerves, reduced blood circulation, muscle pain due to the inter-structural fascia tissue fibers having reduced flexibility, tearing of the fascia tissue if the fascia tissue fibers are too intertwined, and so on.

Figure 40B:
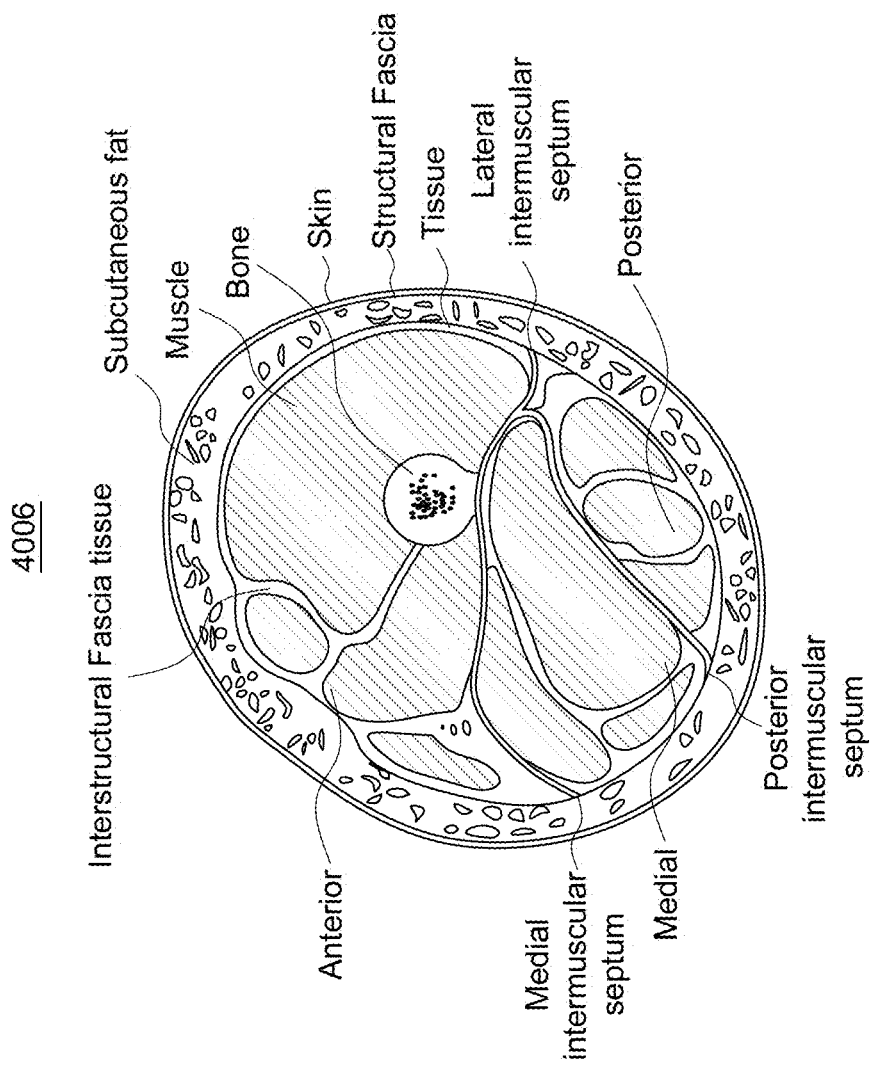
FIG. 40B is an illustration of a cross-sectional view of a leg showing illustrative structural and inter-structural fascia tissue and muscle.
Figure 42:
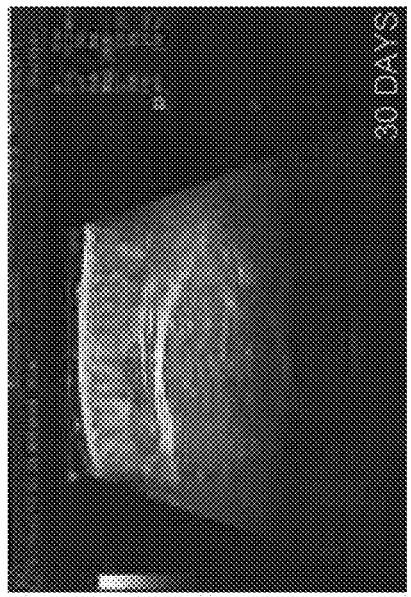
FIGS. 41-44 are images from an ultrasound analysis of patient tissue taken at different intervals during treatment using a fascia tissue therapy device.

FIG. 40B is an illustration of a cross-sectional view of an illustrative leg 4006 showing illustrative structural and inter-structural fascia tissue and muscle, including anterior or quadriceps muscles, posterior or hamstring muscles, and medial or adductor muscles. The human body is formed of a "web" of interconnected systems. When one part of the system slacks, the rest may suffer. Nowhere is that more true than with fascia tissue. This web of fascia tissue impacts every bone, organ, muscle, and bit of soft tissue in the body. Healthy or unhealthy fascia tissue may have a big impact in quality of life of an individual. For example, unhealthy fascia tissue may mean that fascia tissue has adhesions such that the fascia tissue may squeeze a muscle to restrict blood flow or circulation to an extremity or pinch a nerve to cause inflammation or pain. As shown, inter-structural fascia tissue form sheaths or barriers around and between the different muscles of the leg. Similar structural and inter-structural fascia tissues are located through the entire human (and animal) body.

The human body generally has four types of fascia tissue, each with its own role to play. The fascia tissue types include structural fascia, inter-structural fascia, visceral fascia, and the spinal straw. The two most commonly known types of fascia tissue are traditionally called "superficial fascia" and "deep fascia," which are both part of the structural fascia. These terms can be somewhat misleading because superficial and deep fascia tissue barely begin to describe the "big picture" of fascia tissue and the functions the fascia tissue plays for the human body. In fact, if a cadaver dissection is examined, you fascia is not stacked in neat, linear layers, but are rather form an interwoven, consecutive piece of fascia tissue, like a 3D spider web.

More specifically, fascia is a system of internal connective tissue that forms fibrous bands or sheets throughout the body. The structural fascia, including superficial and deep fascia, surrounds muscles, nerves, blood vessels, and internal organs. Fascia tissue is often considered the body's first line of defense against infection and other pathogens, and the fascia tissue creates an environment for tissue repair to occur.

Fascia tissue may be thought of as a layer of plastic wrap holding the contents of a sandwich together, but in this case, the sandwich is the body including organs and tissue (e.g., muscle, bone, etc.) therein. The top layer of the wrap is the superficial fascia or structural fascia tissue and the bottom layer is deep fascia, which includes inter-structural fascia (found within internal structures, such as muscles), visceral fascia ("goopy" fascia, found in the abdomen), and spinal straw (found within the vertebral column and all around the spine).

While fascia tissue is essentially a single interconnected piece of tissue, the fascia tissue does look and operate differently depending on where the fascia tissue located. For example, the superficial fascia tissue (located just under the skin in the subcutaneous tissue) is filled with sensory receptors and functions to anchor skin to the tissues and organs below. The superficial fascia tissue is a thin, fibrous material that is classified as loose connective tissue throughout the skeletal muscles. Superficial fascia is a subcategory of the structural fascia.

Deep fascia tissue is a little different from superficial fascia tissue as the deep tissue is found further below the surface and surrounds, separates, and supports every structure in the body. Deep fascia tissue is also filled with sensory receptors, and is sensitive to changes in pressure and movement—especially through massage and stretching. Deep fascia tissue is also a subcategory of the structural fascia.

As a summary, superficial fascia tissue and deep fascia tissue have more similarities than differences, where both are made of connective tissue and contain bundles of collagen and elastin fibers. The primary difference between superficial fascia tissue and deep fascia tissue is that superficial fascia tissue is composed of loose connective tissue and is found in the layer between the dermis layer of your skin and muscles, while deep fascia tissue contains dense connective tissue and is found within and between your muscles, where the muscles and fascia tissue work together in the extracellular matrix. Researchers used to think of deep fascia tissue as a second layer of superficial fascia tissue, but have recently come to understand that the superficial fascia tissue extends far deeper in the body than previously credited. Treatment of the superficial fascia tissue and deep fascia tissue utilizing the fascia tissue treatment devices, as described herein, allows for "fascial shearing" and restructuring of the different types of fascia tissue, thereby resulting in healthy fascia tissue and alleviation or elimination of effects resulting from the fascia tissue having adhesions or otherwise damaged, as shown in the ultrasound images of FIGS. 41-44. Utilizing the fascia tissue treatment devices with effectors and treatment processes described herein, it is possible to treat both the superficial fascia tissue and deep fascia tissue in a manner that provides for "fascial shearing" and is able to remove adhesions of the fascia tissue at any depth of the body. Treating deep tissue, of course, may take longer than treating superficial fascia tissue.

In various embodiments, the treatment device may include an ultrasound system and/or sonography imaging device that uses high-frequency sound waves to produce images of the fascia tissue, including different layers of fascia tissue depending on the ultrasound sensor and imaging software. The ultrasound system may form part of the computing device for the therapy device and may be configured to transmit images to the controller for further analysis. The controller may be configured to utilize the images to identify problem areas along a patient's body. In an embodiment, a medical professional and/or operator may be create a treatment plan based on the imaging of the fascia tissue with the assistance of the user interface. In an alternative embodiment, the user interface may be configured to determine a treatment plan based on the images, and evaluate treatment progress over time based on repeated images of the same area, as further described hereinbelow.

Figure 45:
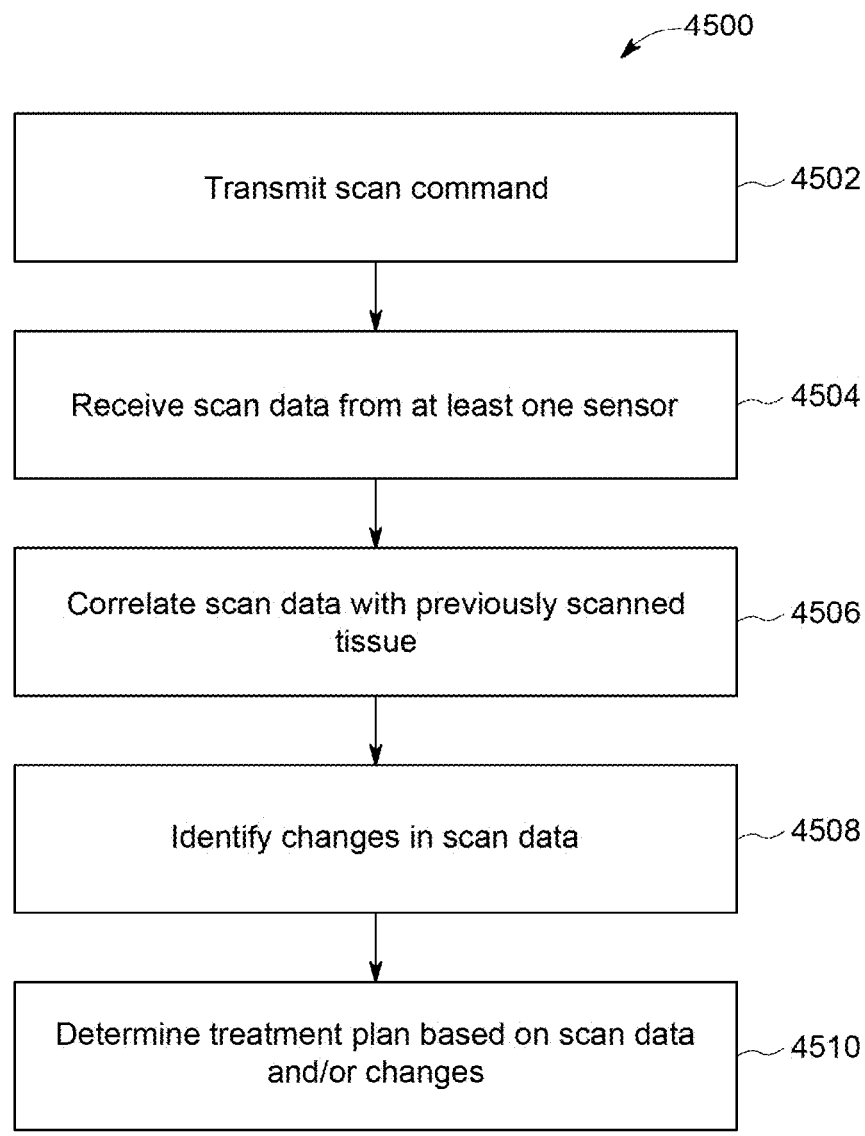
FIG. 45 is a flow diagram of an illustrative method for fascia tissue analysis.

For example, in a pre-treatment mode, the controller may be configured to guide a user to place the therapy device at different locations along a patient's body to map various areas of the body (see ultrasound images 4100, 4200, 4300, 4400 in FIGS. 41-44). The controller may be configured to operate the ultrasound system at each location to obtain images across a range of resolutions and/or tissue depths (e.g., three tissue depths at each location, etc.). The controller may then analyze the images to identify areas of high fascia tissue density, fragmentation, and/or other image characteristics that are indicative of fascia tissue abnormality. The controller may be configured to perform image analysis based on predetermined algorithms in memory, and/or by transmitting the images to a remote computing system (e.g., a cloud computing system) for further analysis. In at least one embodiment, the controller may be configured to use images from different patient screenings (in combination with user inputs identifying problem areas) as a training set for machine learning and/or artificial intelligence (AI) algorithm that can automatically identify fascia tissue damage and/or abnormalities. The machine learning algorithm may also be used—in combination with historical data from patient treatment protocols—to determine a treatment plan based on the detected fascia tissue abnormalities. The machine learning algorithm may utilize a k-nearest neighbor (KNN) algorithm and/or another classification algorithm to classify fascia tissue characteristics relative to common fascia tissue characteristics of other patients so that successful treatments that work for different types of fascia tissue characteristics can be applied to a patient. The AI identification of certain fascia tissue characteristics may be specific to specific body areas (e.g., lower back, calves, scalp, etc.) requiring treatment, the type of treatment that is required, and/or the required number of treatments. The controller may be configured to utilize the ultrasound images to determine or select particular effector characteristics (e.g., size, shape, finger orientation, etc.) and control parameters (e.g., operating speed, force, etc.) to use to improve treatment efficacy. Referring to FIG. 45, an illustrative method 4500 of fascia tissue analysis is shown. The method 4500 includes transmitting a scan command (at operation 4502) to a treatment device to perform a fascia tissue scan (e.g., via ultrasound, etc.), receiving scan data (at operation 4504) (e.g., images of the tissue at different depths, etc.), correlating scan data with previously scanned tissue (at operation 4506), identifying changes in scan data (at operation 4508) (e.g., by comparing scan data with images from previous scans, etc.). In some embodiments, the method 4500 also includes determining a treatment plan based on scan data and/or identified changes in scan data (at operation 4510). In other embodiments, the method 4500 may include additional, fewer, and/or different operations.

The tissue treatment device (e.g., the therapy device, fitness device, etc.) may also include sensors that interface with the computing device to ensure the correct device and/or tissue treatment assembly is being used for a prescribed treatment protocol and to monitor operation of the treatment device during treatment (e.g., the average applied force, torque, rotational speed, duration of use, etc.). For example, each treatment device may be coded with a type, size, etc., and each tissue treatment assembly (e.g., each effector, etc.) may also be coded with a type, size, finger or treatment element type, shape, etc. In coding the treatment devices and tissue treatment assemblies, chips, such as RFID chips or processor chips or memory chips, may be coded with identifying information, thereby enabling the user interface to receive and record the identification information so that historical records may be maintained in an automatic manner. The controller may record this data at periodic intervals (as shown in FIGS. 44C-44F), which can be fed back into the machine learning algorithm to update and/or improve treatment prescription.

The treatment device may also include other forms of skin treatment devices. For example, the treatment device may include an infrared element to treat a patient's skin and/or underlying tissue, a radio frequency skin tightening system, and/or ultrasonic tissue treatment system. In some embodiments, the treatment device also includes a lubrication system (e.g., nozzles, a micropump, etc.) that is structured to dispense a lubricating agent to a patient's tissue to reduce friction between the effector and the patient's skin during rotation of the effector, thereby enabling the operator to continuously treat the patient without having to stop using the therapy device. In an embodiment, feedback from a torque sensor may be utilized to determine when additional lubricant should be applied to the skin, and the lubrication system may automatically dispense or be caused to dispense lubricant to the skin by the therapy device. These auxiliary treatment devices may be at least partially contained within the housing of the therapy device and/or may be attached to the treatment device in place of, or in addition to, the tissue treatment assembly. In yet other embodiments, these auxiliary treatment devices may form their own treatment device that may be detachably coupled to the base station. The lubrication may be stored in a reservoir stored in the enclosure that may be refillable or cartridges of lubrication may be replaced in the lubrication system, as previously described.

The actuator of the treatment device is configured to power rotation of the tissue treatment assembly. The actuator may include a direct drive motor that engages the tissue treatment assembly without any intervening transmission or gear set. Among other benefits, using a direct drive motor reduces heat produced by the treatment device and wear on the internal components. The direct drive motor may also reduce the weight of the treatment device due to the increased torque to weight ratio of the motor. In other embodiments, the actuator includes another form of electromechanical device (e.g., brushless direct current motor, electromagnetic device, etc.). In other embodiments, the actuator includes a pneumatic motor that is configured to drive rotation of the tissue treatment assembly using air pressure. For example, the pneumatic motor may consist of a turbine in the treatment device housing that is driven into rotation by compressed air provided through the tether to the base station. In other embodiments, the actuator may include a hydraulic motor and/or system.

Figure 46:
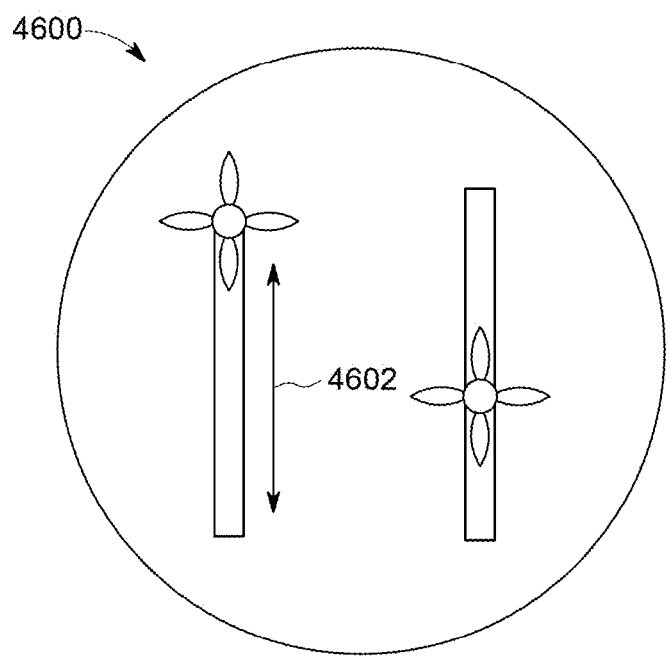
FIG. 46 is an illustration of a bottom view of yet another illustrative fascia tissue treatment device.
Figure 47:
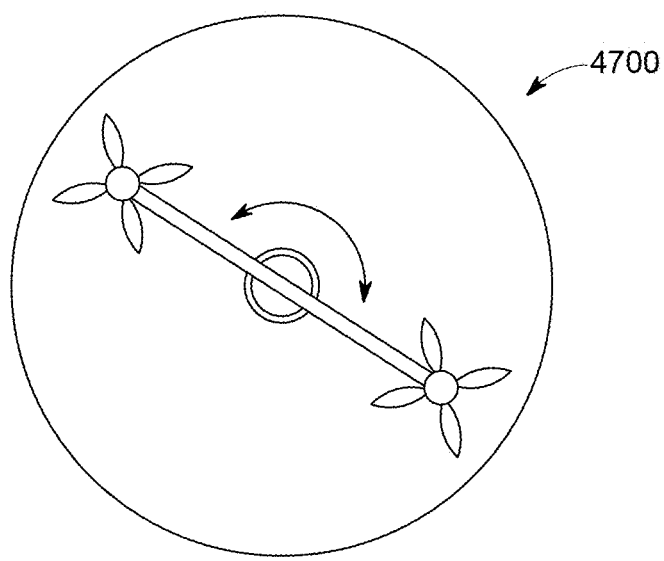
FIG. 47 is an illustration of a bottom view of yet another illustrative fascia tissue treatment device.
Figure 51:
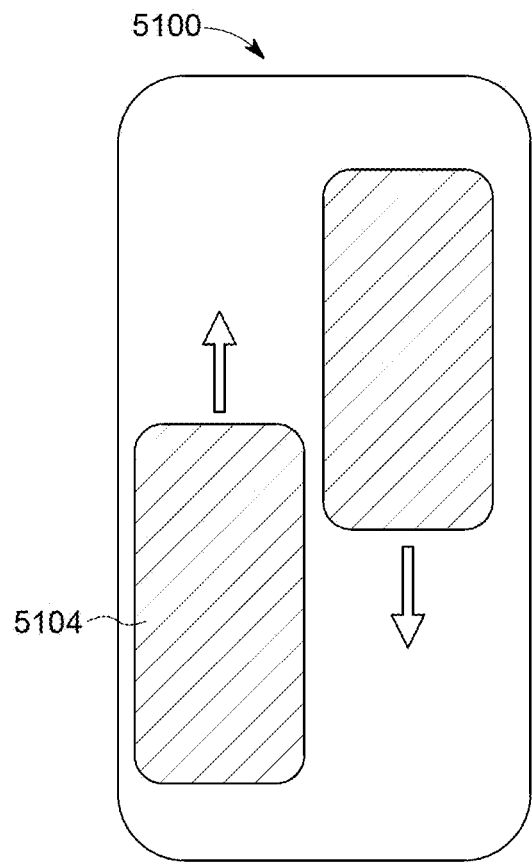
FIGS. 51-53 are illustrations of bottom views of yet another illustrative fascia tissue treatment device.
Figure 52:
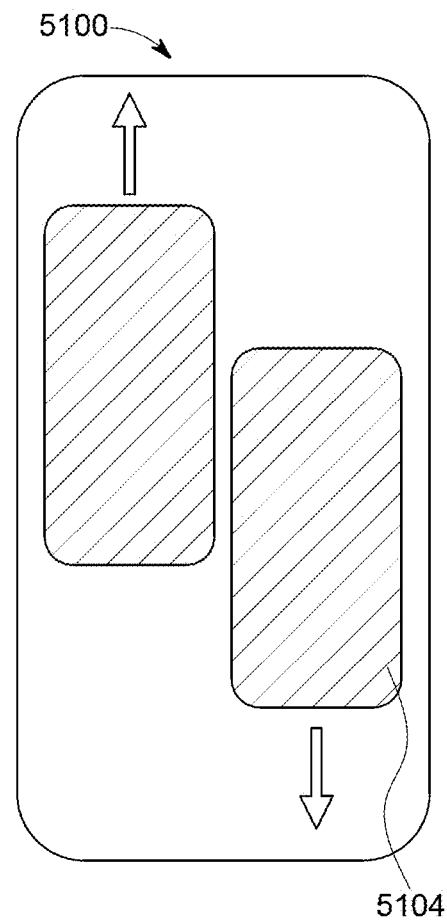
Figure 53:
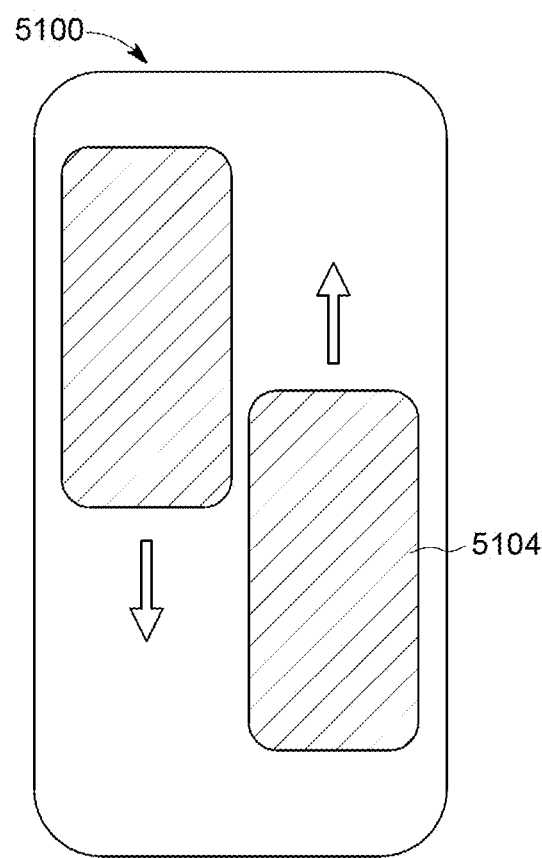
Figure 54:
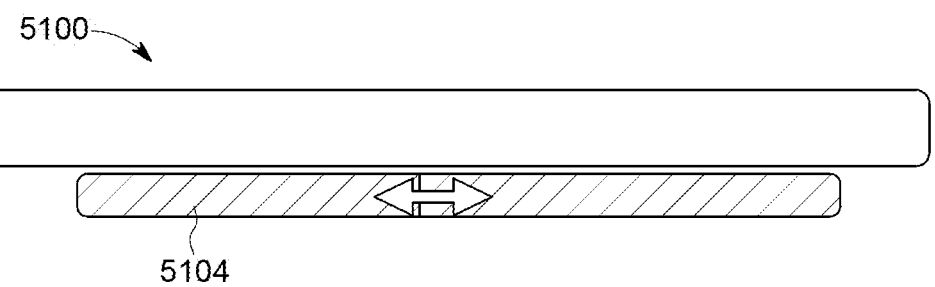
FIG. 54 is an illustration of a side view of the illustrative fascia tissue treatment device of FIG. 51.

In some embodiments, the actuator may be configured to move the effector and/or individual treatment elements along a single direction (e.g., linearly back and forth, etc.) instead of, or in addition to, a rotational direction. For example, FIG. 46 shows an illustrative fascia tissue treatment device 4600 in which the actuator is structured to move individual treatment elements (e.g., claws, etc.) back and forth along a single direction 4602. The elements may be staggered at different positions along each actuator or aligned. FIG. 47 shows another illustrative fascia tissue treatment device 4700 in which the actuator includes a radial bar that connects multiple tissue treatment elements and alternates direction (e.g., rotational direction) to move each element along a semi-circular path. In yet other embodiments, the treatment device may include a shaft with offset lobes (e.g., similar to an engine crankshaft) to move the treatment elements along guides (e.g., slots) in the housing. In yet other embodiments, the treatment device may include feet (e.g., made from silicone and/or coated with silicone or another suitable material) that may translate back and forth along the treatment device, as shown in FIGS. 48-54. For example, FIGS. 48-50 show a treatment device 4800 that includes tissue treatment assembly including a plurality of feet 4804 (e.g., pads, panels, etc.) that are coupled to the treatment device 4800 separately from one another. The feet 4804 move in alternating directions along a linear path. The feet 4804 may move in unison with one another or at least partially in opposition depending on the treatment modality. FIGS. 51-54 show a treatment device 5100 that includes only two feet 5104 that move in opposing directions when the actuator is in an ON position. It should be understood that the size of the feet and range of motion of the feet may be different in various embodiments.

Figure 55:
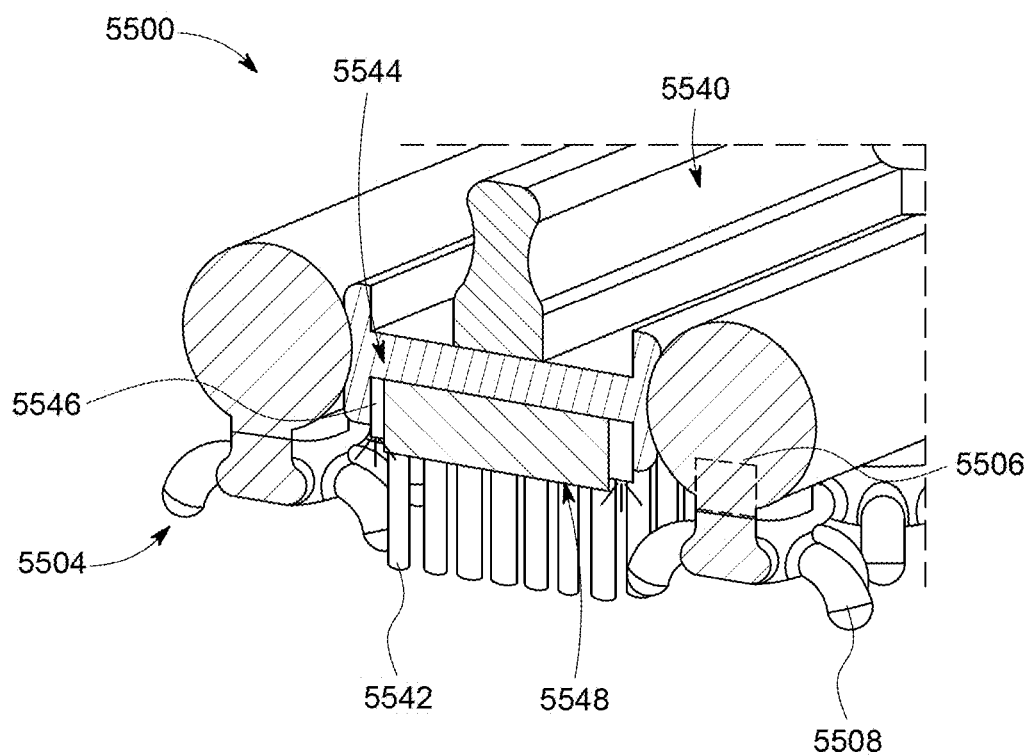
FIG. 55 is an illustration of a isometric view of yet another illustrative fascia tissue treatment device.

In yet other embodiments, the actuator may be another form of rotational and/or vibrational device (e.g., an electromagnetic device, a rotating cable extending through the tether and driven by a motor in the base station, etc.). Vibration of the treatment device may be random or non-random. For example, the device may rotate and vibrate up-and-down. The device may alternatively rotate and randomly vibrate. For example, FIG. 55 is an isometric view of an illustrative treatment device 5500 that includes a linear actuator 5506 that is configured to vibrate or otherwise translate a treatment element 5508 back and forth along a linear direction (e.g., parallel to a central axis of a support bar to which the treatment elements 5508 are mounted, etc.). The treatment element 5508 (e.g., the actuator 5506) may thereby thump, hammer, or pulsate against the patient's tissue during operation.

In some embodiments, the actuator 5506 may also be configured to vibrate the tissue treatment assembly (e.g., the effector, etc.) in combination of spinning or another form of movement.

In some embodiments, the treatment device 5500 (e.g., the actuator 5506 of the treatment device 5500, the tissue treatment assembly 5504, etc.) may be configured to apply micro-currents or certain electrical currents through the tissue treatment assembly 5504 and/or another treatment accessory to electrically stimulate the tissue in combination with spinning and/or vibration and/or to apply light in certain wavelengths to enhance fascia tissue treatment by the treatment device 5500. For example, as shown in FIG. 55, the treatment device 5500 may include a treatment accessory 5540 that is detachably coupled to the treatment device 5500 that is configured to apply electrical currents and light in certain wavelengths to a patient's skin. The treatment accessory 5540 may include brushes 5542 arranged in rows along the treatment accessory 5540, although various other arrangements may be used in other embodiments. The bristles of the brush 5542 may be made of any suitable material including nylon, polypropylene, horse hair, feather, or any other natural or synthetic filament material. The tips of the bristles may be flocked (split) or unflocked. The tips of the bristles may also be rounded, bulbous, flat, pointed, etc. The bristles may be soft and flexible for a comfortable and soothing treatment, or may be rigid and stiff for a more aggressive tissue treatment. In some embodiments, the bristles include both soft/flexible bristles and rigid/stiff bristles for a combined treatment. In other embodiments, a first brush of the treatment device 5500 may have a first type of bristles and a second brush having a different type of bristles.

The therapy device of FIG. 55 may also include a light therapy system 5544 including a plurality of light emitting diode (LED) lights 5546 directed toward the skin to provide additional therapy to the fascia tissue. The light therapy system 5544 may provide light in one or more of the following forms: Red light (625 nm), Blue light (415 nm), Red+Blue light (625 nm-415 nm), Infrared (760 nm). The computing device may be configured to power and control operation of the LEDs. User input controls, such as knobs, buttons, or otherwise, may be accessible to a user from the treatment device 5500 and/or base station to control operation of the LEDs and control circuitry.

The LEDs may be disposed at any location in which the light can be properly directed to a patient's skin (i.e., is not blocked by another element of the treatment device 5500). For example, the LEDs may be at the tips of the tissue treatment element(s) of the tissue treatment assembly 5504 or along a periphery of the treatment device 5500. The LEDs may be pointed at an angle outward from the device, toward the tissue treatment assembly 5504, or in any other location, arrangement, and/or orientation so as to direct light onto the skin surface. The LEDs may be aimed in front of, to the side, or between the treatment elements so that the lights may be incident skin of a user prior to and/or after the treatment elements pass a region of skin of a user. In an embodiment, a motion sensor may sense when the device is in use (e.g., moving back and forth) and cause the LEDs to automatically turn ON during motion, and cause the LEDs to automatically turn OFF when not in motion or not moving in a particular treatment motion (e.g., rotating, substantially linearly forward/backward or side-to-side, where substantially means that there may also be some rotational and/or vibrational movement during operation). One or more pressure sensors (e.g., between the treatment element(s) and bar) may also be utilized to determine when the device is in operation and cause the LEDs to turn ON and OFF. A timing circuit may be utilized to maintain the LEDs in the ON state for a minimum duration of time (e.g., 15 seconds). In an embodiment, circuitry may turn the LEDs ON and OFF in a particular pattern, such as lighting certain LEDs when moving in a first direction and other LEDs when moving in a second direction.

As shown in FIG. 55, the treatment device 5500 may also include a soft tissue stimulation system 5548 configured to provide electrical current to the treatment area by placing a plurality of electrodes on the skin surface and providing electrical impulses via the electrodes to the skin and soft tissue (such as fascia tissue) below the skin's surface. In some embodiments, the stimulation system 5548 employs circuitry and hardware elements that can execute traditional TENS (transcutaneous electrical nerve stimulation) and/or LAMES (neuromuscular electrical stimulation) therapy. In such embodiments, at least one lead wire may be electrically coupled to the treatment device 5500, with a transcutaneous electrode at the distal end for delivering the electrical impulses to the patient. The transcutaneous electrode may adhere to the skin. The treatment device 5500 may be configured to provide a pre-determined stimulation waveform having a pre-determined frequency (Hz), pulse width (µs), and amplitude (mA). Alternatively the device may be configured to allow a user to modify one or more parameters of the stimulation waveform.

In some embodiments, the electrodes may alternatively be positioned on the treatment device housing (such as on the frame, the bar member, the treatment elements, or the treatment accessory, to be placed in direct contact with the skin for stimulation. In an embodiment, the treatment accessories, for example, may be configured with an accessible compartment that is configured to store batteries, control circuitry, electrode(s), wires, etc., thereby enabling the treatment to be self-contained within the treatment accessories. In other embodiments, the treatment accessories are electrically coupled to the treatment device and powered by the base station. User input controls, such as knobs, buttons, or otherwise, may be accessible to a user to control operation of the stimulation signals applied to a user from the electrodes controlled by the control circuitry. In operation, the user may remove the electrode(s) from the compartment and apply to him or herself. The electrodes, in an embodiment, may be attached to straps that may wrap around or be applied to a patient's body, such as an arm or leg, so as to apply the TENS or LAMES treatment before, during, or after fascia tissue treatment by the treatment device 5500 with the treatment elements. As an example, the electrodes may be positioned to the sides of a pathway that the treatment elements are to be applied and electrical stimulation may occur before, during, or after treatment.

Figure 56:
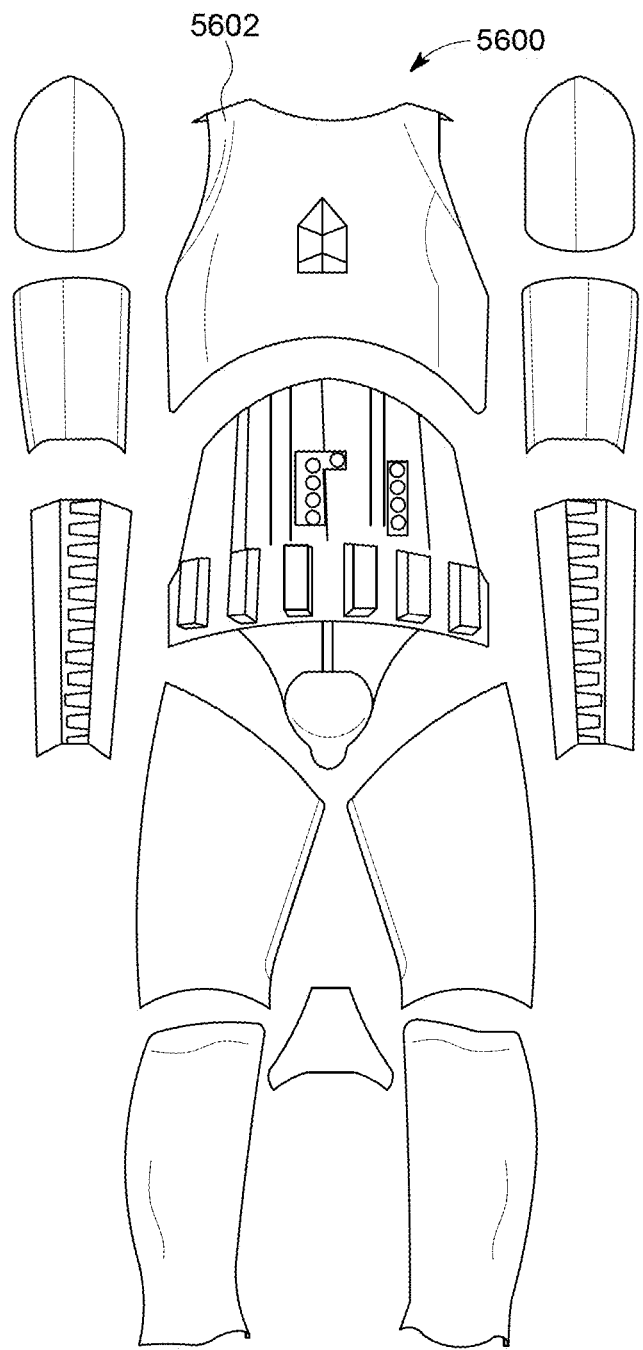
FIG. 56 is an illustration of a front exploded view of an illustrative preparation device.
Figure 57:
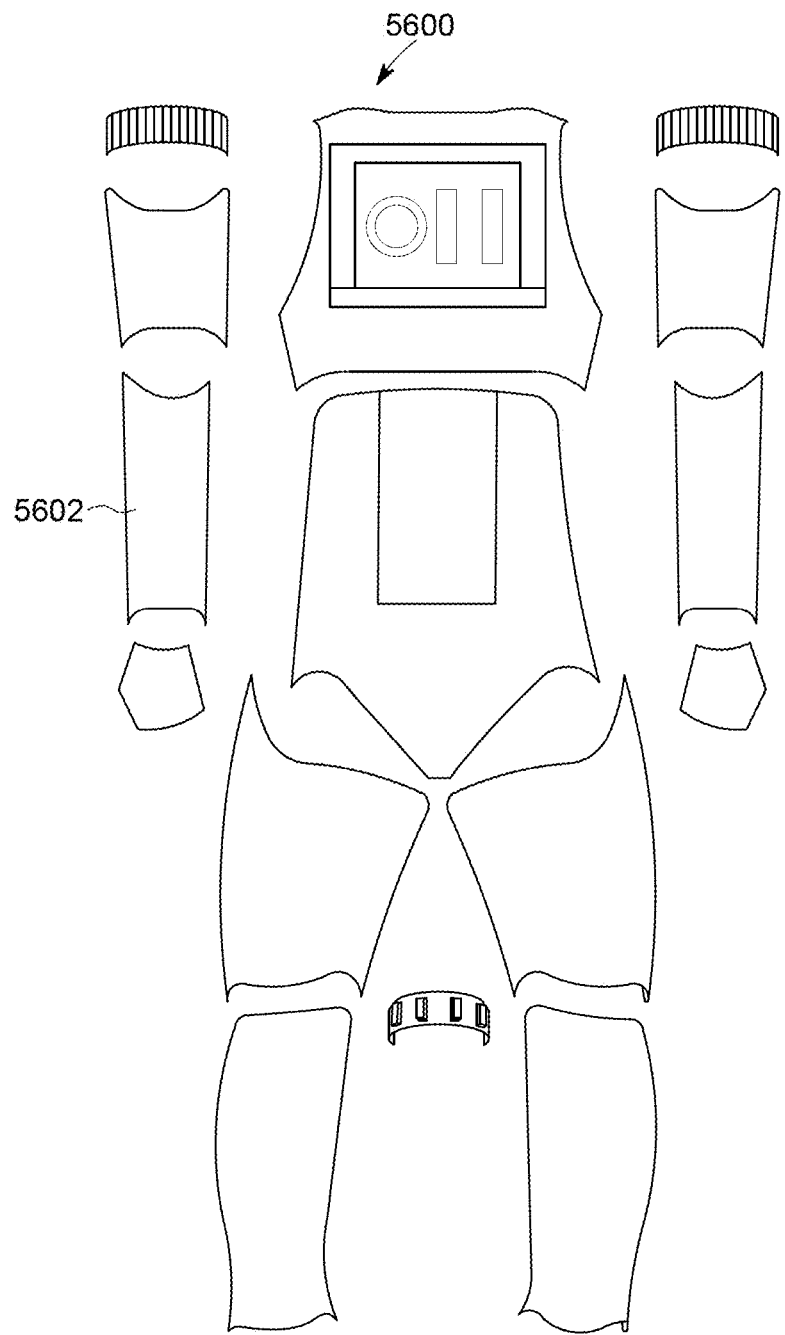
FIG. 57 is an illustration of a rear exploded view of an illustrative preparation device.
Figure 58:
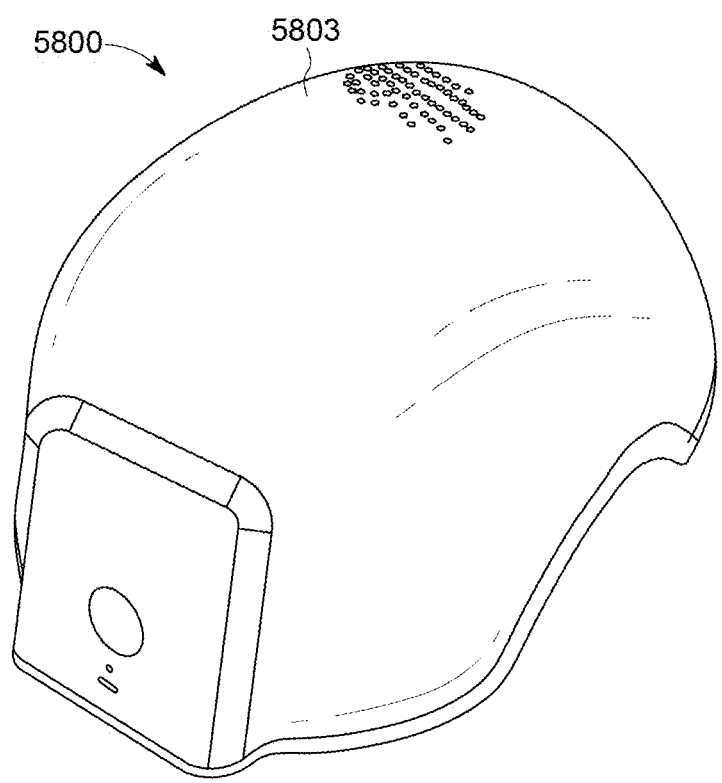
FIG. 58 is an illustration of an isometric view of a helmet for an illustrative preparation device.

As described above, the base station may be configured for use with multiple different types and/or styles of treatment devices (e.g., therapy devices, etc.). In some embodiments, the treatment plan may involve using different treatment devices and/or device attachments in a certain order. For example, the treatment plan may include application of a skin and/or soft tissue preparation device to the patient. The preparation device may include equipment that is structured to be worn by the patient. In one embodiment, the preparation device may include an outer shell (e.g., plastic, etc.) that is shaped to match the contour of a certain body area(s) (e.g., a patient's head, shoulder, thigh, etc.). An illustrative shell 5602 (e.g., armor, etc.) for a preparation device 5600 is shown in FIGS. 56-57. An illustrative helmet 5803 (e.g., head gear, etc.) for a preparation device 5800 is shown in FIG. 58. The preparation device 5600, 5800 may include soft padding that is coupled to an interior surface of the shell 5602 and/or helmet 5803 to improve patient comfort, and straps (e.g., a hook and loop fastener, cord, etc.) to help secure the preparation device 5600, 5800 to the patient during pre-treatment. The preparation device 5600, 5800 may be configured to pre-heat and/or soften the patient's tissue prior to the use of other treatment modalities. The preparation device 5600, 5800 may include lights (e.g., UV lights, infrared heating elements, etc.), gel-packs, ultrasonic transducer (e.g., vibrating elements), or another technology that is coupled to the shell 5602, helmet 5803 and/or padding and positioned to engage with a patient's skin. In some embodiments, the preparation device 5600, 5800 may also include nozzles and/or another dispensing device or system to apply lubricating oils or other agents to facilitate heat absorption to the skin and to prepare the skin/tissue for further treatment).

Figure 59:
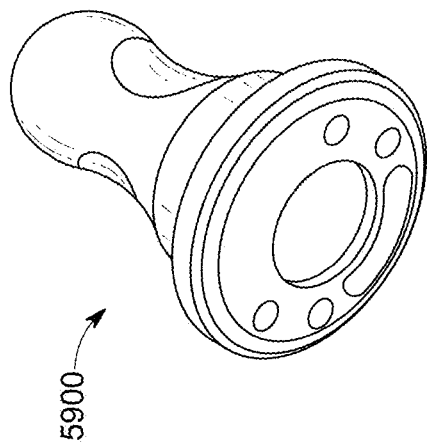
FIG. 59-62 are illustrations of various illustrative fascia tissue treatment devices for use with a therapy system.
Figure 60:
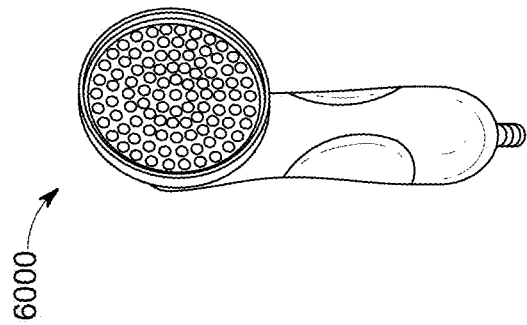

After pre-treatment, in at least one embodiment, the treatment plan may involve using a radio frequency (RF) device (e.g., RF head) as an initial treatment operation. The RF device may be configured to use energy waves (e.g., thermal energy) to help stimulate the superficial skin layers and/or to heat the deep layer of a patient's skin (e.g., to within a range between approximately 122° F. and 167° F., or another suitable temperature). Illustrative RF treatment devices 5900, 6000 are shown in FIGS. 59-60. The treatment plan may include using the RF treatment device(s) 5900, 6000 to apply heat for a prescribed period to stimulate the tissue and promote creation of new collagen fibers.

Figure 61:
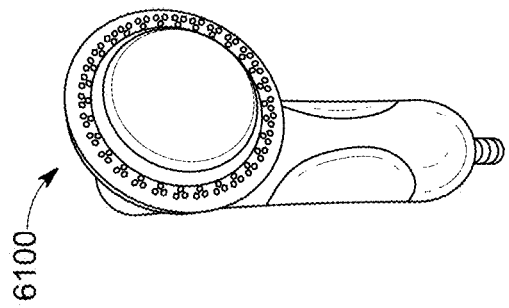

The treatment plan may also include using an ultrasound skin treatment to facilitate the removal of fat deposits under a patient's skin and/or heat the patient's tissue. For example, FIG. 61 shows an illustrative ultrasonic cavitation device 6100 for a tissue treatment that may be coupled to the tether and base station. The cavitation device 6100 may be configured to apply ultrasonic radio waves to the tissue, causing a disruptive vibration. Other example treatment device that may be used include vacuum devices that apply negative pressure to tissue during operation, and/or combination devices that utilize multiple treatment modalities (e.g., RF in combination with spinning or other movement). The treatment plan may also include application of infrared light (e.g., via an IR treatment device), pre-cancerous treatments (e.g., blue light therapy), acne treatment, and/or other tissue treatments. These treatment devices may be accessory heads that can be interchangeably coupled to a single treatment device or separate treatment devices that are coupled to the base station in place of the treatment device, as described above.

Figure 62:
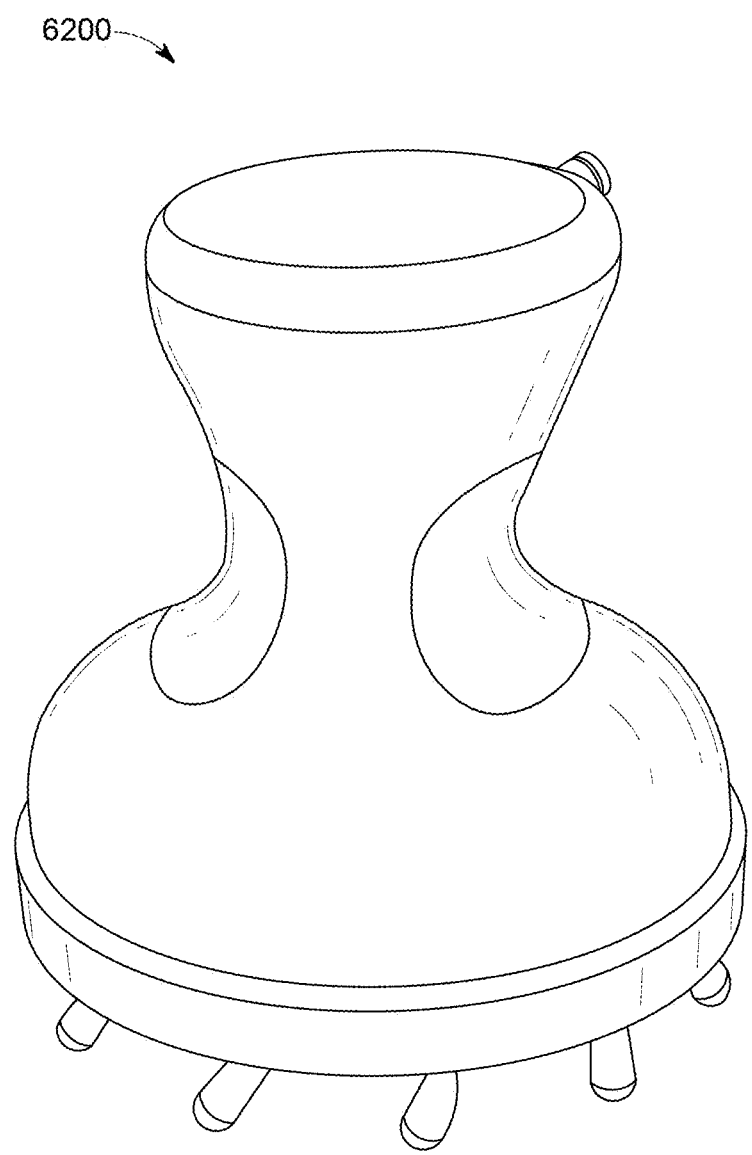
Figure 63:
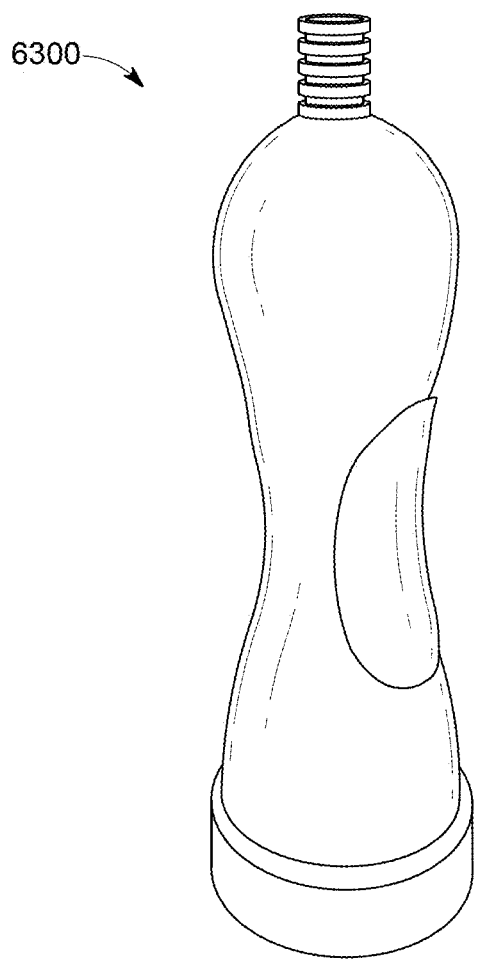
FIGS. 63-64 are illustrations of various illustrative fascia tissue treatment devices that may be used to treat smaller body areas.
Figure 64:
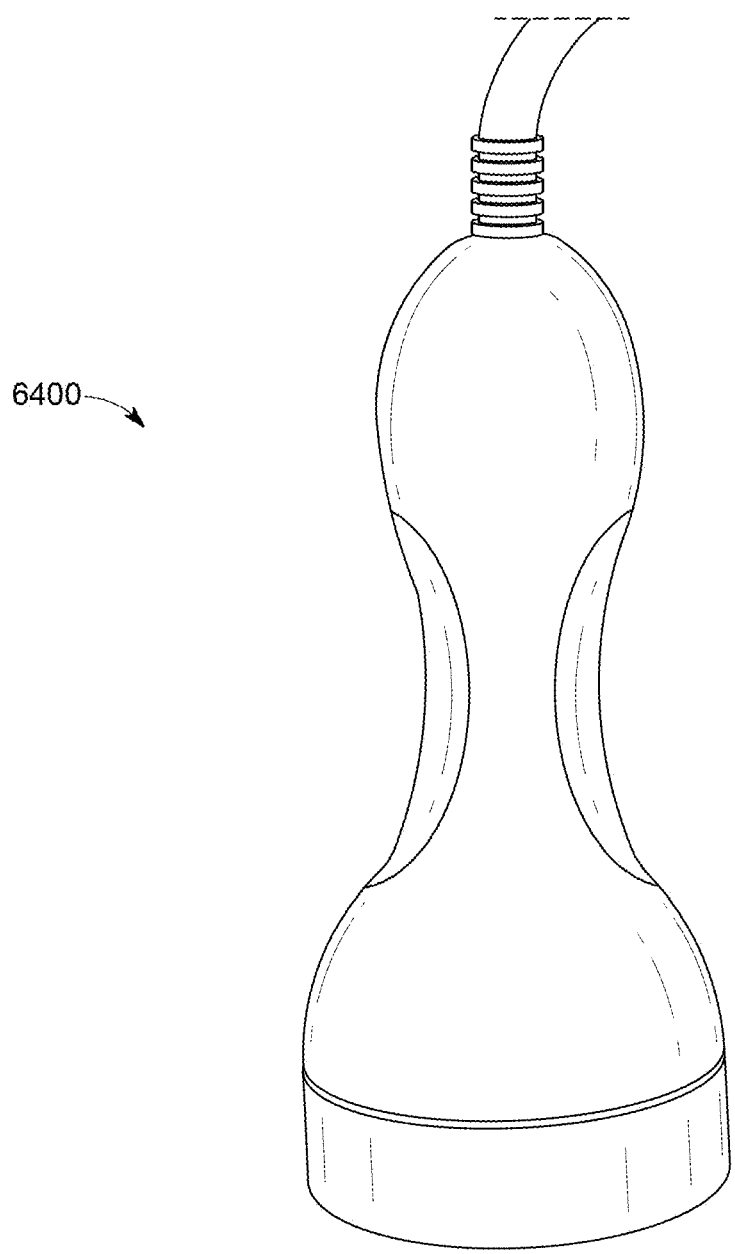
Figure 65A:
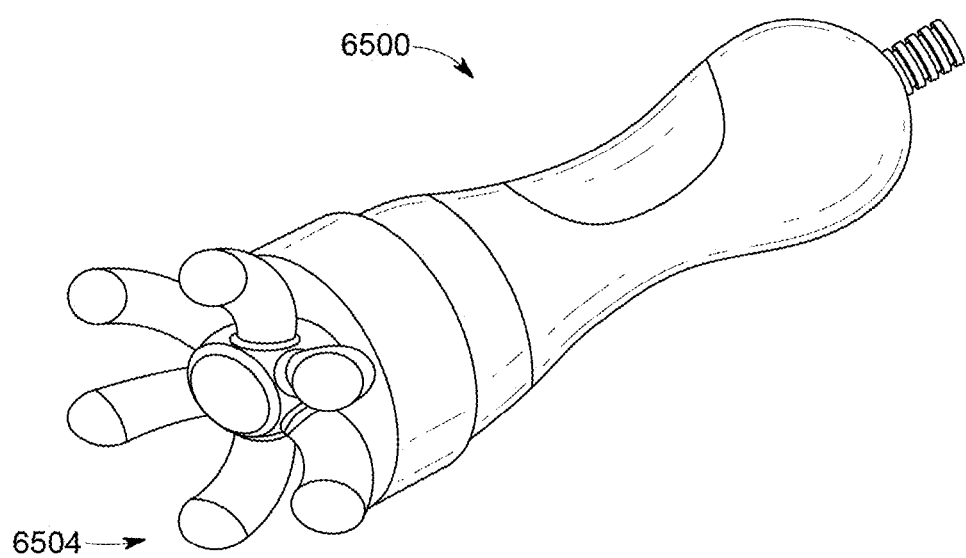
FIGS. 65A-65D are illustrations of yet another illustrative fascia tissue treatment device that may be used to treat smaller body areas.
Figure 65C:
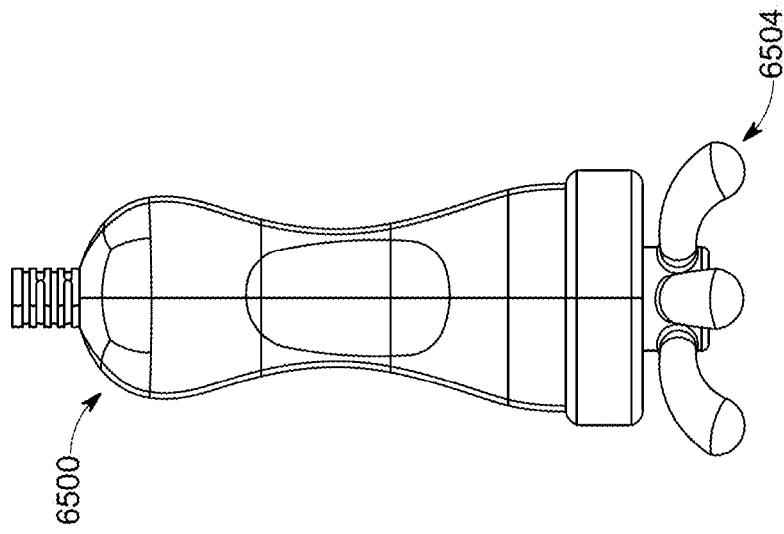
Figure 65B:
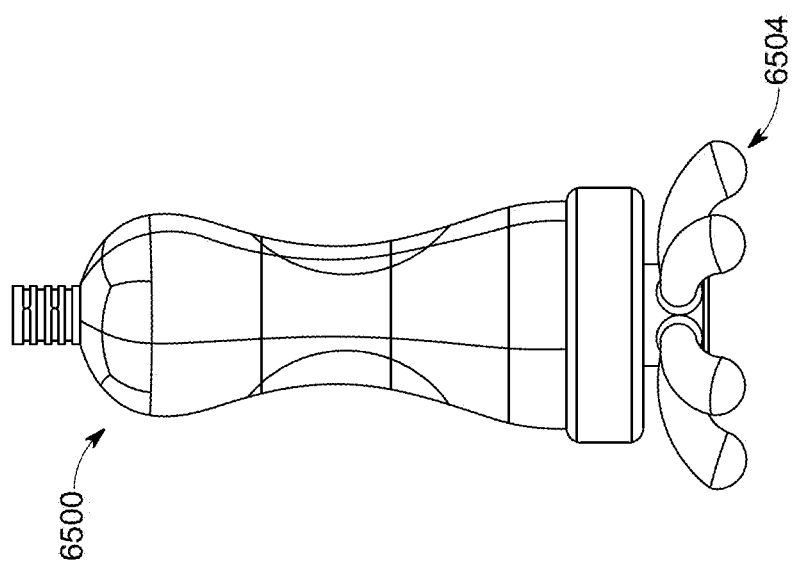
Figure 66:
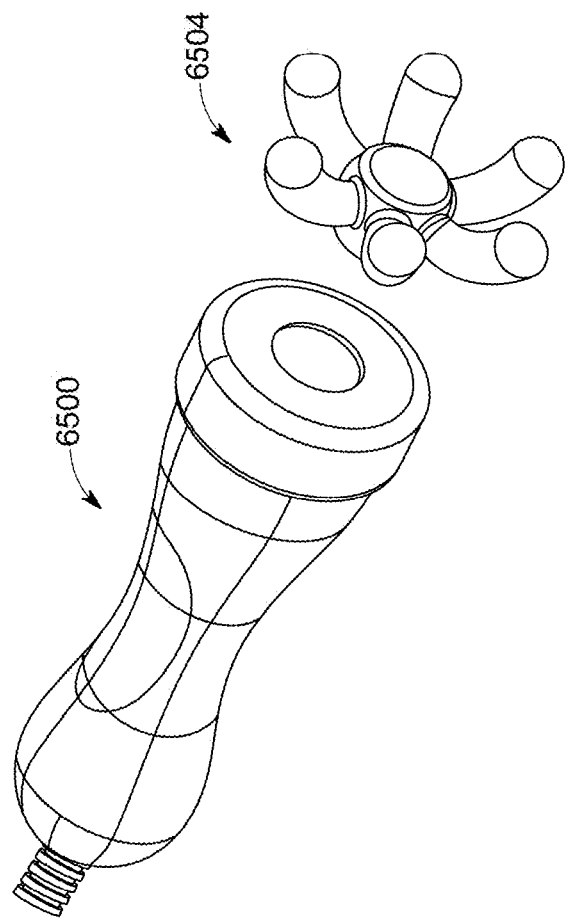
FIGS. 66-73 are illustrations of various illustrative fascia tissue treatment devices that may be used to treat smaller body areas.
Figure 65D:
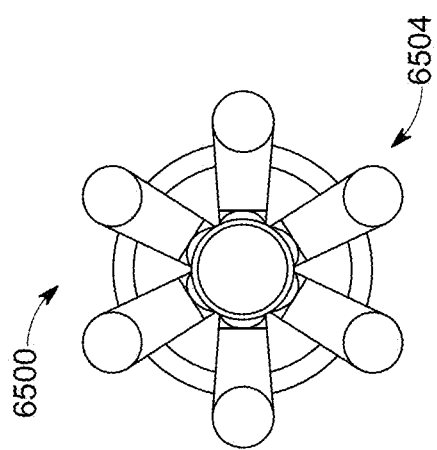
Figure 67:
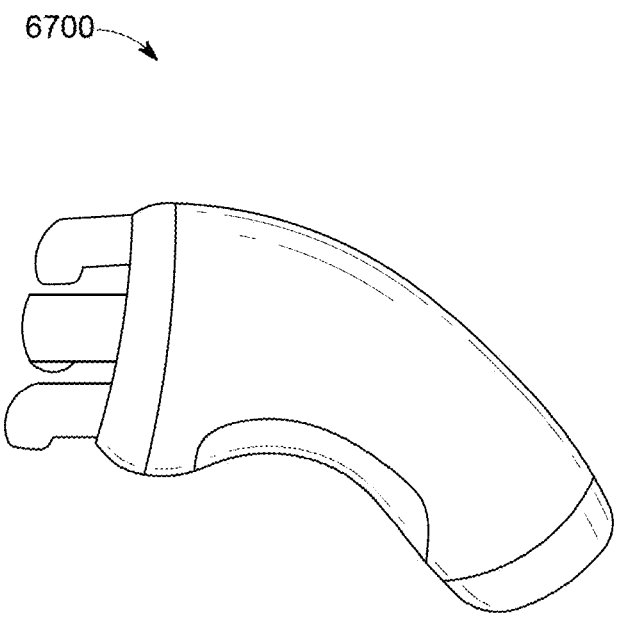
Figure 68:
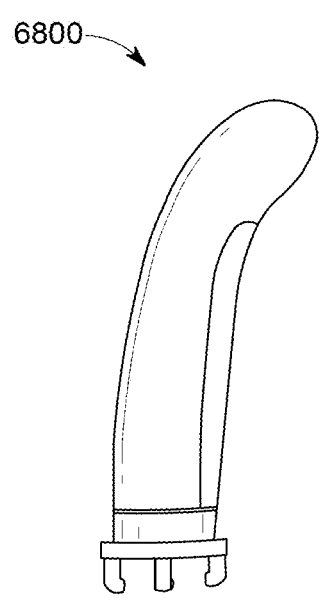
Figure 69:
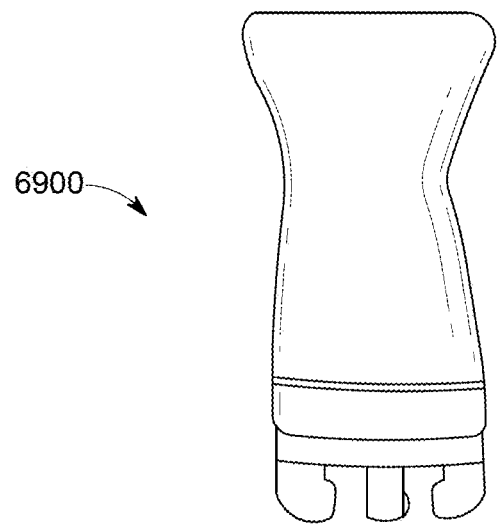
Figure 70:
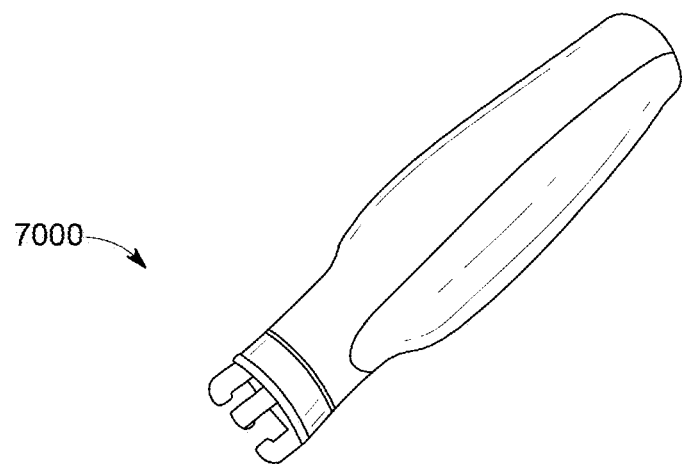
Figure 72:
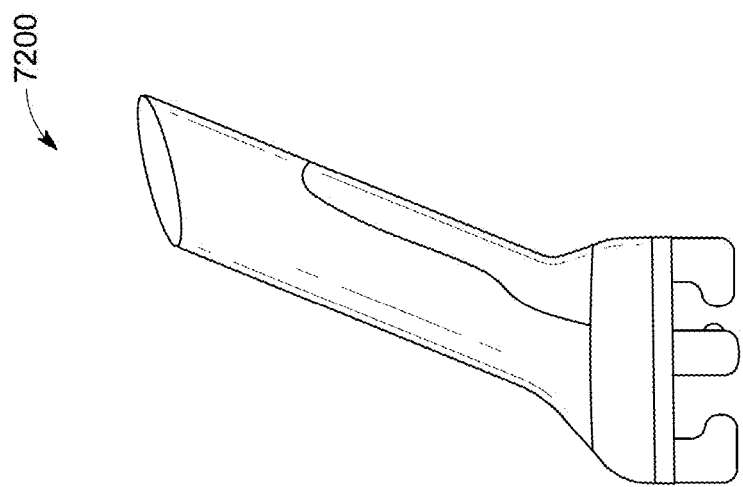
Figure 71:
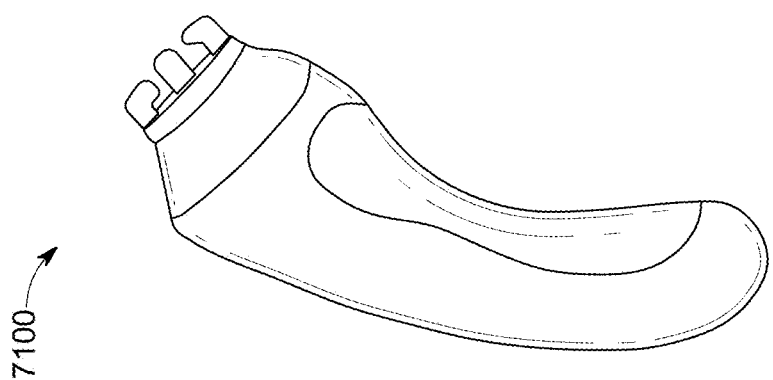
Figure 73:
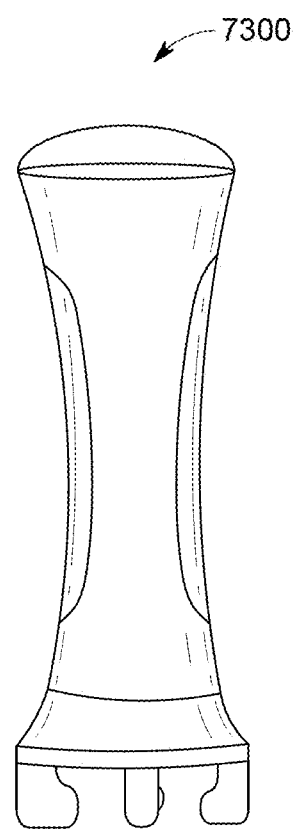
Figure 74:
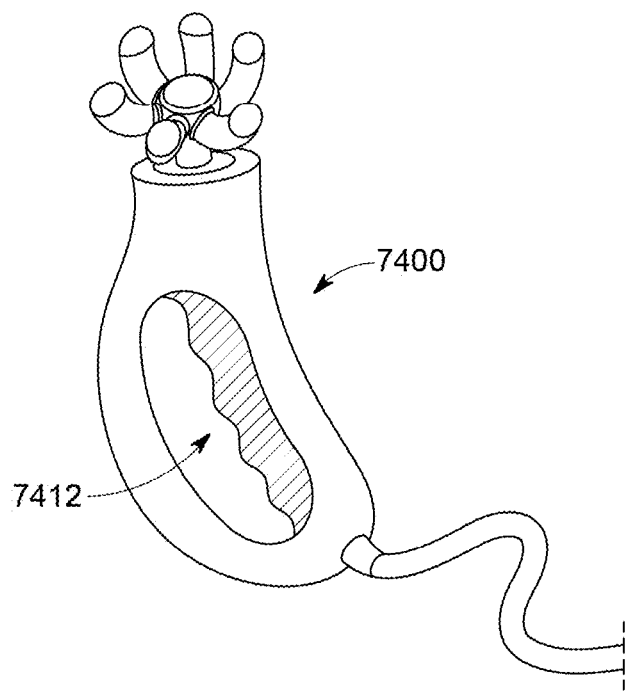
FIG. 74 is an illustration of a front isometric view of yet another illustrative fascia tissue treatment device.
Figure 75:
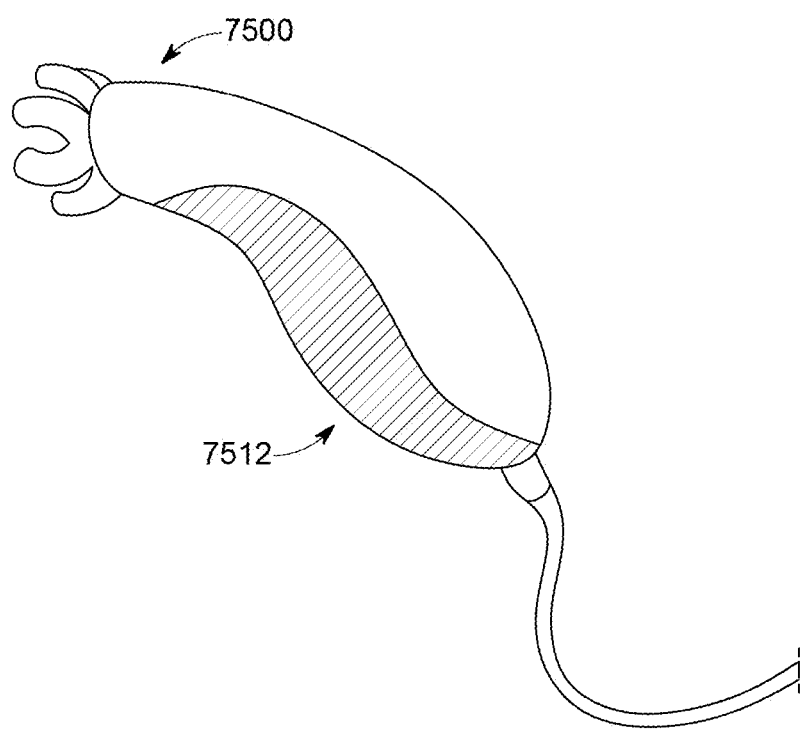
FIG. 75 is a rear isometric view of the illustrative fascia tissue treatment device of FIG. 74.

The size of the treatment device and tissue treatment assemblies may also be different in various embodiments. For example, FIG. 62 shows another illustrative fascia tissue treatment device 6200 that is designed to treat larger body areas (e.g., the back, legs, stomach, etc.). FIGS. 63-75 show various illustrative fascia tissue therapy devices 6300, 6400, 6500, 6700, 6800, 6900, 7000, 7100, 7200, 7300, 7400, 7500 that are designed to manipulate fascia tissue in smaller body areas or to focus application of treatment. These devices may have a smaller overall footprint that the treatment device 6200 of FIG. 62. As shown in FIGS. 65A-65D and FIG. 66, the tissue treatment assembly 6504 (e.g., the effector, etc.) for these smaller devices may include a single tissue treatment element (e.g., a panel with fingers forming a single claw, etc.) to support the treatment element. As shown in FIGS. 74-75, the size of the handles 7412, 7512 and/or grip for the treatment device 7400, 7500 may also differ depending on the size of the treatment device 7400, 7500 and/or its intended use. In some embodiments, the treatment system (e.g., computing device) may be configured to receive data from remote systems, such as other tissue treatment systems, medical devices, and/or data repositories and may be configured to use the received data to determine and/or adjust a treatment plan for the patient.

Figure 76:
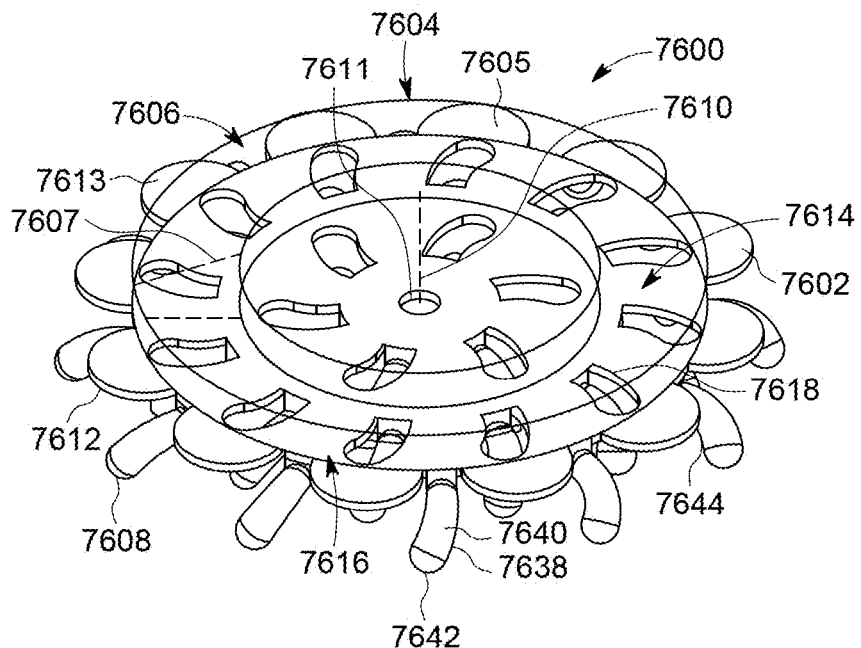
FIG. 76 is a top isometric view of an illustrative tissue treatment effector.
Figure 77:
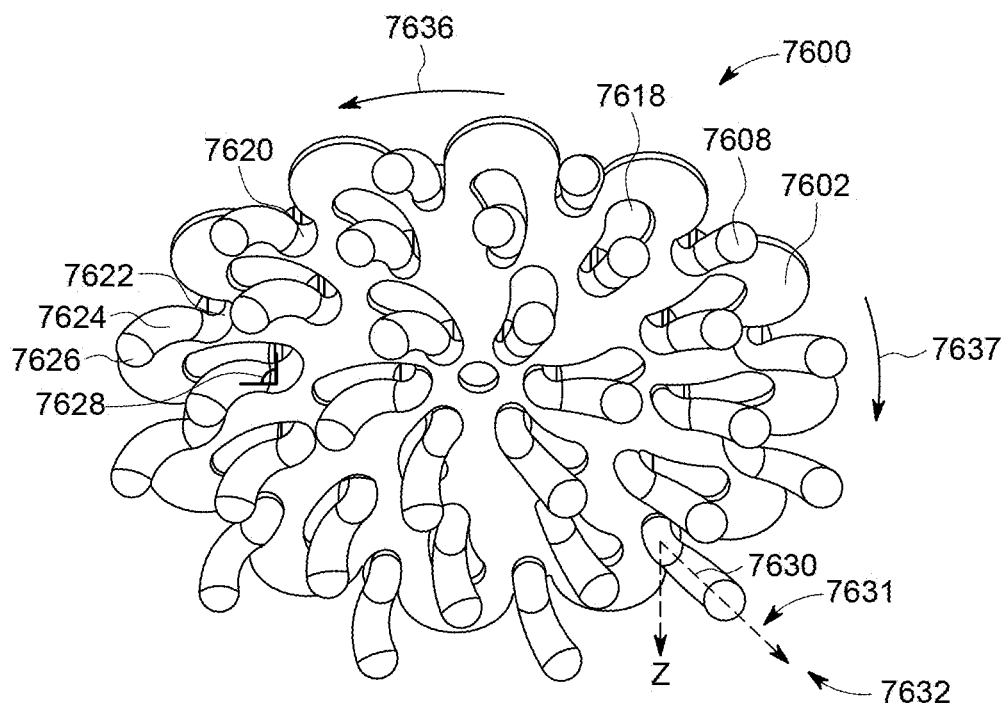
FIG. 77 is an illustration of a bottom isometric view of the illustrative tissue treatment effector of FIG. 76.
Figure 78:
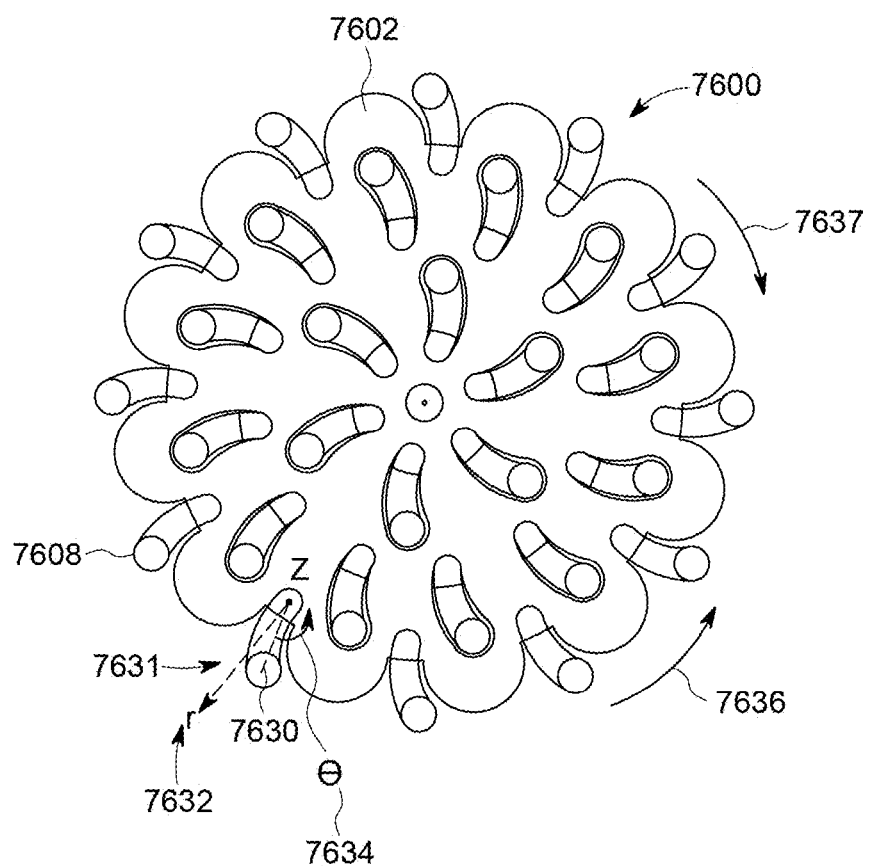
FIG. 78 is a bottom view of the illustrative tissue treatment effector of FIG. 77.

Referring to FIGS. 76-78, an illustrative tissue treatment assembly 7600 (e.g., an effector, etc.) for a fascia tissue treatment device is shown. The tissue treatment assembly 7600 may be made from separate pieces that are fastened or otherwise coupled together. In other embodiments, the treatment assembly may be formed may be a monolithic body formed from a single piece of material (e.g., from plastic via an injection molding process, etc.). The treatment assembly 7600 may include a panel 7602 (e.g., a board, a plate, etc.) that supports a plurality of fascia tissue treatment elements that extend at least partly axially away from the panel 7602. The panel 7602 may also include a support member 7604 (e.g., a support element, a quick-connect device, etc.) disposed on the panel 7602 that is configured to detachably couple the treatment assembly 7600 to an actuator of the treatment device.

The support member 7604 is configured to engage the actuator to mount the treatment assembly 7600 to the actuator. The support member 7604 may include a connecting element 7605 (e.g., a shaft, a mount point, a coupler, etc.) that is configured to detachably couple the support member 7604 to the actuator, as will be further described. In some embodiments, the support member 7604 is coupled to the panel 7602 at a central position along the panel 7602.

In some embodiments, the support member 7604 may be configured to increase the stiffness of the treatment assembly 7600 and to reduce torque and stress on the actuator during operation. For example, as shown in FIG. 76, the treatment assembly 7600 may include a plurality of support elements 7606 (e.g., support ribs, etc.) disposed between adjacent rings of finger members 7608 (e.g., rings of finger members 7608 extending in circumferential rows relative to a central axis 7610 of the panel 7602) and/or aligned with the rings of finger members 7608. The support elements 7606 may be disposed on a first surface (e.g., an upper surface, etc.) of the panel 7602, opposite from the finger members 7608. In some embodiments, support elements 7606 may also be included on a skin facing side of the panel (on the same side of the panel 7602 as the finger members 7608, on a second/lower surface of the panel 7602, etc.).

The support member 7604 may be coupled to the panel 7602 at a position that is spaced radially apart from a center 7611 of the panel 7602. For example, the support member 7604 may be arranged along the panel 7602 so that the connecting element 7605 is at least partially disposed at one of: (i) an outer perimeter 7612 of the panel 7602, or (ii) an intermediate radial position 7614 between the center 7611 of the panel 7602 and the outer perimeter 7612 of the panel 7602.

As shown in FIG. 76, the support elements 7606 include a plurality of cylindrical support ribs 7613 extending at least partially axially away from the panel 7602 and that are arranged concentric with a rotational axis (e.g., the central axis 7610) of the panel 7602. The cylindrical support ribs 7613 may be spaced radially apart from one another. In some embodiments, the support elements 7606 may also include planar ribs 7607 (e.g., spoke ribs, axial ribs, etc.) that engage with and extend between adjacent ones of the cylindrical support ribs 7613. In some embodiments, the support member 7604 (e.g., the support elements 7606 together) form a skeletal framework 7616 that is engageable with a connector on the treatment device (e.g., the actuator, etc.) to ensure that the load is more uniformly distributed across the surface of the panel 7602. The support elements 7606 (e.g., the cylindrical ribs) may include quick-connect fittings to attach the treatment assembly to the treatment device at the intermediate radial position 7614 along the panel 7602 or at along the outer perimeter 7612 of the panel 7602, as described in further detail above.

Figure 79:
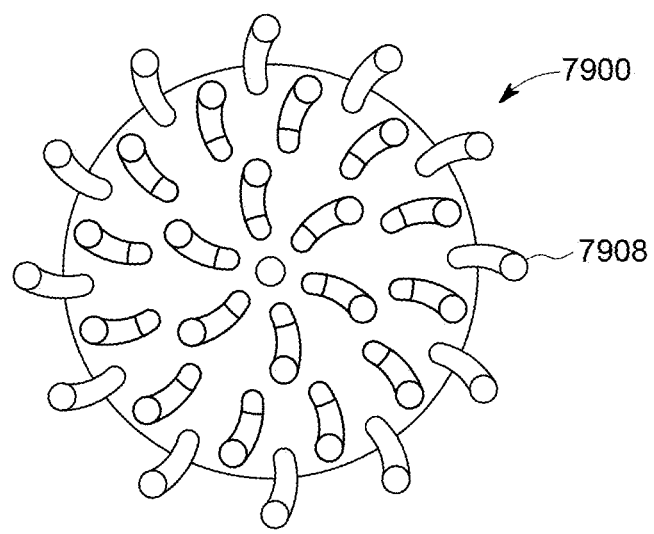
FIG. 79 is an illustration of another illustrative tissue treatment effector.
Figure 80:
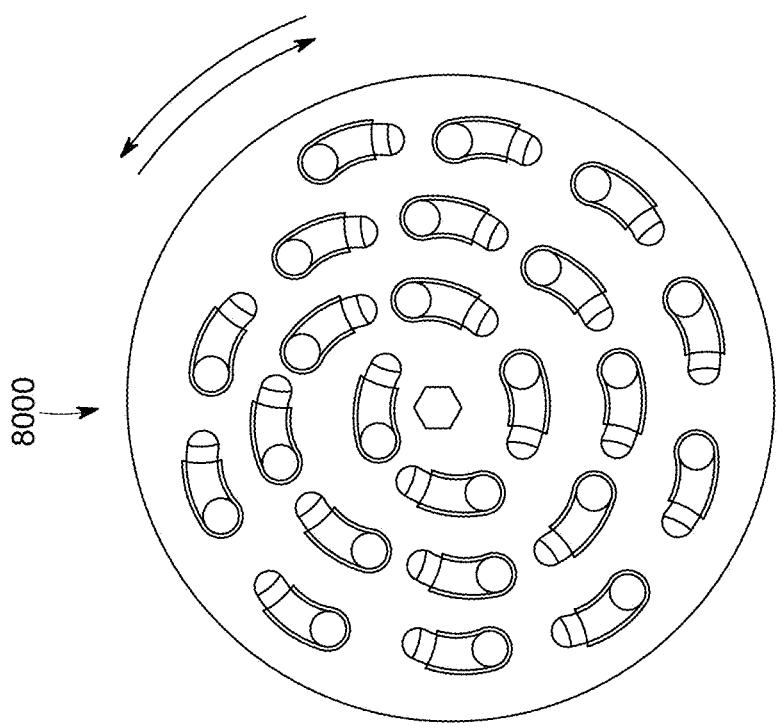
FIG. 80 is an illustration of a bottom view of yet another illustrative tissue treatment effector for a fascia tissue treatment device.
Figure 81:
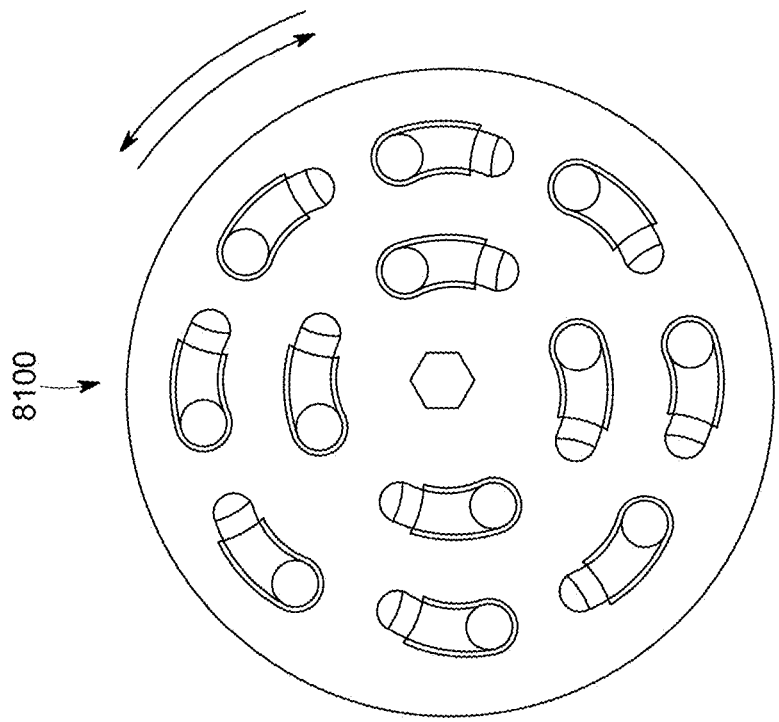
FIG. 81 is an illustration of a bottom view of yet another illustrative tissue treatment effector for a fascia tissue treatment device.

In the embodiment of FIGS. 76-78, the panel 7602 is a disk-shaped plate that includes an opening 7618 (e.g., cutouts, holes, etc.) at a location of each of the treatment elements (e.g., the finger members 7608). The panel 7602 may have an outer diameter within a range between approximately 0.5 inches and 12 inches. In other embodiments, the shape and/or size of the panel 7602 may be different. The treatment elements are uniformly distributed across the panel 7602 at approximately equal intervals. As shown in FIGS. 76-78, the treatment elements are arranged in concentric rows that are centered about a rotational axis (e.g., the central axis 7610) of the panel 7602. FIG. 79 shows another embodiment of a tissue treatment assembly 7900 that includes treatment elements (e.g., finger members 7908) arranged in concentric rows relative to a central axis of a panel. In other embodiments, the treatment elements may be arranged in a spiral shape (e.g., as shown in the tissue treatment assembly 8000 of FIG. 80) or another suitable shape. In some embodiments, adjacent rows of treatment elements are rotationally offset from one another (e.g., such that the treatment elements are not aligned along a radial direction, as shown in the tissue treatment assembly 8100 of FIG. 81) to distribute stress more uniformly across the surface of the panel. However, it will be appreciated that the shape, size, and arrangement of treatment elements may be different in other embodiments.

As shown in FIG. 77, the treatment elements include a plurality of rigid finger members 7608 that are fixedly coupled to the panel 7602 at a proximal end 7620 of the respective finger members 7608 and extend away from the panel in at least partly axial direction. The plurality of finger members 7608 may be elongated so that a cross-sectional diameter of the finger members 7608 is less than a length of the finger members 7608. The finger members 7608 may define a plurality of tip portions (e.g., tips, etc.) that are substantially co-planar to one another and are disposed along a reference plane that is parallel to and spaced apart from the panel 7602 and that is substantially perpendicular to the central axis 7610 of the panel 7602. As shown in FIGS. 76-78, the finger members 7608 may be at least partially curved and aligned or oriented along a direction of rotation of the panel 7602. As shown in FIG. 77, the finger members 7608 each include a first portion 7622 extending axially away from the panel 7602, a second portion 7624 extending at an angle 7628 relative to the first portion 7622 (e.g., radially and/or circumferentially away from the first portion 7622, and a third portion 7626 extending partly axially away from the second portion 7624. The third portion 7626 may be curved along a radial and/or circumferential direction (e.g., clockwise when viewed from above the panel 7602) along the panel and/or about the central axis 7610 of the panel 7602.

In at least one embodiment, as shown in FIGS. 77-78, each one of the finger members 7608 has a central axis 7630 (e.g., finger member axis, etc.) extending from the proximal end 7620 to a distal end 7621 of the respective finger member 7608. At least one of the central axes 7630 may extend at least partly along a radial direction 7632 and/or a circumferential direction 7634 of the panel 7602 (e.g., relative to a cylindrical coordinate system 7631 that is centered on the proximal end 7620 of the respective finger member 7608 and/or relative to the central axis 7610 of the panel 7602, etc.). The circumferential direction 7634 may be oriented along a direction of travel of the panel 7602 when the actuator is in the ON state so that at least a portion of each one of the finger members 7608 extends along the circumferential direction 7634. In at least one embodiment, the central axes 7630 of the finger members 7608 extend along the circumferential direction 7634. In some embodiments, the finger members 7608 extend away from the panel 7602 (e.g., are curved away from the panel 7602) toward a direction of rotation of the panel 7602 when the actuator is in an ON state (e.g., so that the finger members 7608 extend along a first circumferential direction 7636 relative to the central axis 7610 that is the same as a direction of travel of the panel 7602 when the actuator is in the ON state). By aligning the finger members 7608 with the direction of travel, the finger members 7608 can project into a patient's tissue during treatment, in a scooping or shoveling motion to facilitate the release of fascia tissue. However, it should be appreciated that the actuator may be configured to rotate the panel 7602 in multiple directions (e.g., both the first circumferential direction 7636 or clockwise direction and a second circumferential direction 7637 or counterclockwise direction) in some embodiments, and that the opposing alignment of finger members 7608 with the direction of travel of the panel 7602 can provide different effects depending on the rotational direction, which can further promote fascia tissue release in some circumstances.

The size, shape, and arrangement of finger members 7608 along the panel 7602 may be different in various embodiments. As shown in FIG. 76, at least one of the finger members 7608 may include a shaft 7638 having a convex surface 7640 extending between the proximal end 7620 and the distal end 7621 of the at least one finger member 7608. The at least one finger member 7608 may define a tip 7642, which may be monolithic with the shaft 7638 and at which the convex surface 7640 transitions to a concave surface 7644. The concave surface 7644 may be oriented with a direction of travel of the panel 7602 when the actuator is in the ON state so that the concave surface 7644 defines a leading surface/edge of the at least one finger member 7608.

In other embodiments, the size, shape, and arrangement of the finger members 7608 along the panel 7602 may be different. For example, the finger members 7608 may be rotated approximately 90 degrees from the orientation shown in FIGS. 76-78 such that the second portion 7624 and the central axis 7630 of the finger members 7608 extend at substantially along the circumferential direction 7634.

Figure 82:
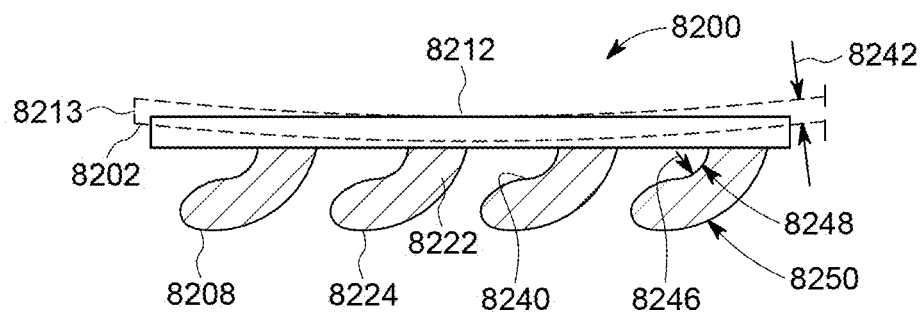
FIG. 82 is an illustration of a side view of yet another illustrative tissue treatment effector.

FIG. 82 shows an illustration of a side cross-sectional view of another illustrative tissue treatment assembly 8200 (e.g., an effector, etc.). As shown, the finger members 8208 each include a first portion 8222 engaged with a panel 8202 and of the treatment assembly 8200 extending axially away from the panel 8202, and a second portion 8224 engaged with the first portion 8222 and curved along a circumferential direction, and along a rotational direction of the panel. In this arrangement, each of the individual finger members 8208 have a convex surface 8240 extending between a proximal end and a distal end of the respective finger member 8208 that faces axially toward the panel 8202, so as to form small scooping elements having a smaller first radii 8246 along an inner surface 8248 than along an outer, skin facing surface 8250. Beneficially, angling and/or curving the finger members 8208 along the circumferential direction can facilitate manipulation of the fascia tissue layers and promote release and treatment of abnormal/damaged fascia tissue. Reversing the rotational direction of the panel 8202, so that the distal end of the finger members 8208 define a trailing surface and/or trailing edge of the finger members 8208 may alter the forces applied to the fascia tissue during treatment and may further effectuate the release of fascia tissue in certain treatment modalities.

As shown in FIG. 82, in some embodiments, the panel 8202 of the tissue treatment assembly is substantially planar. In other embodiments, the panel 8202 may be made from a flexible material (e.g., a material capable of bending easily without breaking, a pliant material, a material able to bend to form a radius of curvature that is at least 5%, 10%, 15%, or greater of an outer radius of the panel 8202, etc.) and may be curved along a radial direction in a neutral position of the panel 8202 (in which no forces are being applied to the panel 8202) such that a central region or center 8212 of the panel 8202 (e.g., proximate to a rotational axis of the treatment assembly) is raised above or protrudes axially away from an outer perimeter 8213 of the panel 8202. As the tissue treatment assembly 8200 is pressed toward (e.g., along an axial direction) a patient's skin during treatment, such as in response to an axial force applied to the center 8212 of the panel 8202, the center 8212 of the panel 8202 bends toward the skin and into axial alignment with the rest of the panel 8202 (e.g., such that the center 8212 and the outer perimeter 8213 of the panel 8202 are disposed along the same reference plane and/or are substantially flush with one another). A thickness 8242 of the panel 8202 may be sized such that a force required to substantially the center 8212 with the outer perimeter 8213 of the panel 8202 is less than or equal to a target force applied to the skin during treatment (e.g., 1N, 5N, 10N, or any force between or greater than the foregoing forces).

Figure 83:
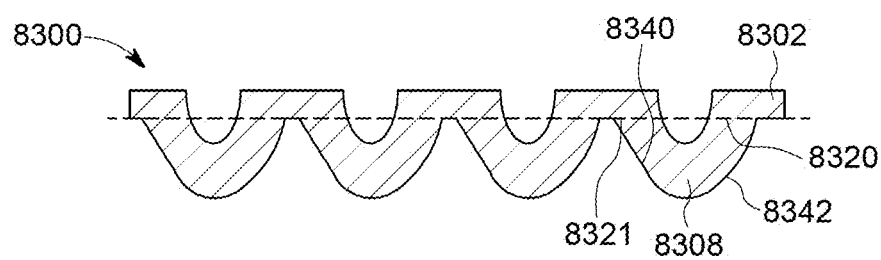
FIG. 83 is an illustration of a side view of yet another illustrative tissue treatment effector.

FIG. 83 shows a side cross-sectional view of yet another illustrative tissue treatment assembly 8300 (e.g., an effector, etc.). As shown, the treatment elements of the treatment assembly 8300 include a plurality of finger members 8308 that are curved back toward the panel such that at least one (or each) finger member 8308 engages the panel at opposing ends of the finger member 8308 (e.g., at both a proximal end 8320 and a distal end 8321 of the respective finger member 8308). At least one finger member 8308 may include a cutoff (e.g., straight section) along an outer surface of the respective finger member 8308, proximate to an end of the finger member 8308 such that the finger member 8308 includes a first edge 8340 extending substantially axially away from the panel 8302 and a second edge 8342 opposite from the first edge 8340 that curves back toward the panel 8302. In such an arrangement, the finger member(s) 8308 "scoop" or otherwise act against the tissue along a rotational direction of the treatment assembly 8300 (e.g., along a single rotational direction when the first edge 8340 is a leading edge of the finger member 8308 during operation). As such, reversing the rotational direction of the treatment assembly 8300 may reduce how aggressively the finger members engage with the patient's tissue. In such an arrangement, concave surfaces of the finger members 8308 lead the finger members 8303 along the rotation of the finger members 8308, thereby causing tips of the finger members 8308 (e.g., a point along the finger members 8308 that is farthest from the panel 8302) to follow the shafts (e.g., main body portion, etc.) of the finger members 8303 rather than lead the shafts of the finger members 8308. In some embodiments, by aligning the orientation of the finger members 8308 with the rotation direction, rotational stress of each of the finger members 8308 may be reduced.

Figure 84:
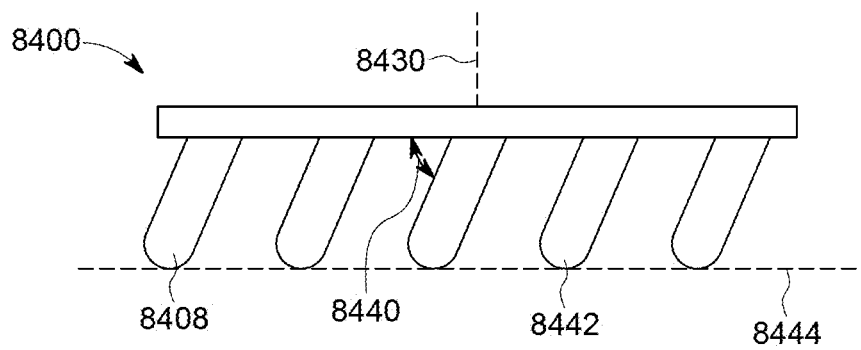
FIG. 84 is an illustration of a side view of yet another illustrative tissue treatment effector.

FIG. 84 shows a side cross-sectional view of yet another illustrative tissue treatment assembly 8400 (e.g., an effector, etc.). The treatment assembly 8400 includes a plurality of finger members 8408 that extend away from the panel at an oblique angle 8440. As shown in FIG. 84, the finger members 8408 are angled along a circumferential direction toward the direction of rotation of the panel when the actuator is in an ON state. As shown, the plurality of finger members 8408 may define respective tip portions 8442, which may be substantially co-planar. The tip portions 8442 may define a plane 8444 (e.g., a tip-contact plane, etc.) that is spaced apart (e.g., axially, etc.) from the panel and that is substantially perpendicular to a central axis 8430 of the panel. In other embodiments, such as when the panel is made from a flexible material, the panel may bend under an applied force to bring the tip portions 8442 into alignment with the plane 8444. In yet other embodiments, such as during application to curved body areas, the panel may remain curved.

Figure 85:
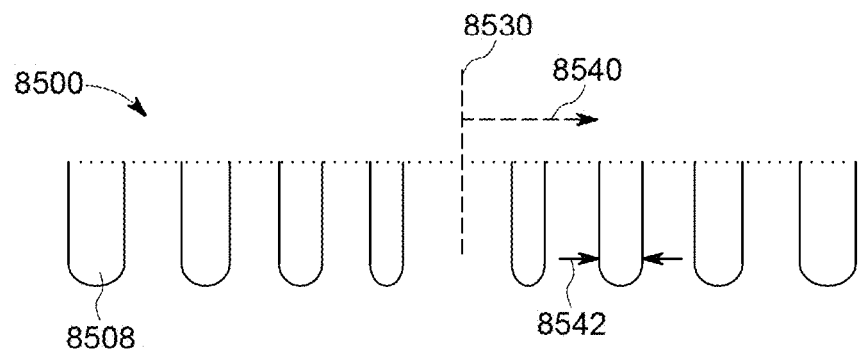
FIG. 85 is an illustration of a side cross-sectional view of yet another illustrative tissue treatment effector.

FIG. 85 is a side cross-sectional view of yet another illustrative embodiment of a tissue treatment assembly 8500 (e.g., an effector, etc.) for a fascia tissue therapy system. As shown, the tissue treatment assembly 8500 includes a panel or base and multiple tissue treatment elements that are coupled to the panel. In at least one embodiment, the tissue treatment elements are finger members 8508 that extend axially away from the panel. In other embodiments, at least one finger member 8508 is angled with respect to a central axis of the panel. In yet other embodiments, at least one finger member 8508 curves away from the panel. The panel may include a circular, planar disc or another suitable support structure for the finger members 8508 (e.g., a skeletal framework, etc.). The finger members 8508 are shown as cylindrical elements but may have a different geometry or size in other embodiments.

For example, the size of the finger members 8508 may increase with increasing radial position 8540 along the panel, relative to a central axis 8530 of the panel. In at least one embodiment, an outer diameter 8542 of the finger members 8508 increases (e.g., continuously) with increasing radial position 8540 along the panel. In this way, a contact area between each finger member 8508 and a person's skin increases with increasing radial position 8540 along the panel. This arrangement can reduce the risk of tissue damage in areas of the panel where the speed is greatest (e.g., approaching the outer diameter of the panel). By using different finger profiles based on distance from a center location, the treatment assembly may be used in different manners.

Figure 86:
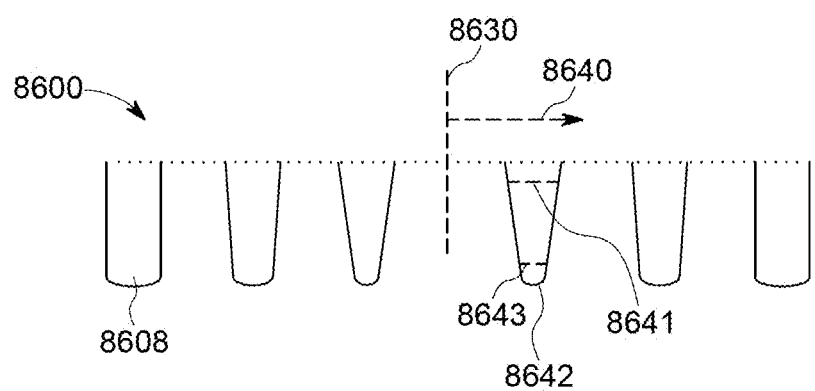
FIG. 86 is an illustration of a side cross-sectional view of yet another illustrative tissue treatment effector.

FIG. 86 shows a side cross-sectional view of yet another illustrative treatment assembly 8600 (e.g., an effector, etc.). The treatment assembly 8600 includes finger members 8608 that have different shapes. The shape of the finger members 8608 may vary with radial position 8640 along the panel, relative to a central axis 8630 of the panel. As shown in FIG. 86, the finger members 8608 are arranged in concentric rows that each extend along a circumferential direction, and the shape of the finger members 8608 varies between the rows. In other embodiments, the shape of the finger members 8608 may also vary within a single row (e.g., along a circumferential direction within the row, etc.). The finger members 8608 may taper to form different sized and/or shaped finger member tips 8642 at a distal end (e.g., outermost end, etc.) of the finger members 8608. A size of the finger member tips 8642 may increase with increasing radial position 8640 along the panel such that outer finger members 8608 can perform slightly different treatment than the inner finger members 8608. In the embodiment of FIG. 86, an innermost set of finger members 8608 (e.g., tapered finger members, etc.) nearest a central axis 8630 of the panel have a substantially triangular shape (with a rounded or curved tip), whereas an outermost set of finger members 8608 (e.g., untampered finger members, etc.) farthest from the central axis 8630 of the panel have a substantially rectangular shape (e.g., a rectangular body with a curved lower surface or face that forms a tip at a tip region).

Figure 87:
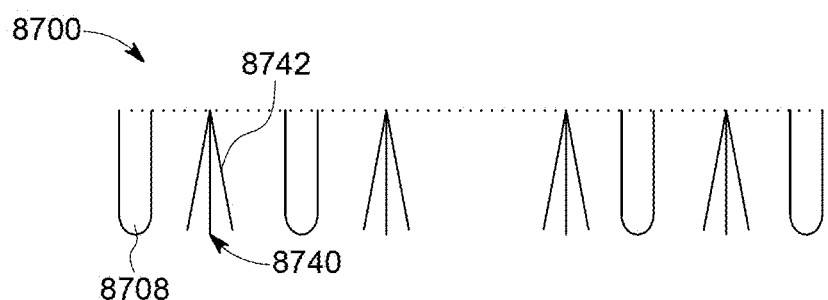
FIG. 87 is an illustration of a side cross-sectional view of yet another illustrative tissue treatment effector.
Figure 92A:
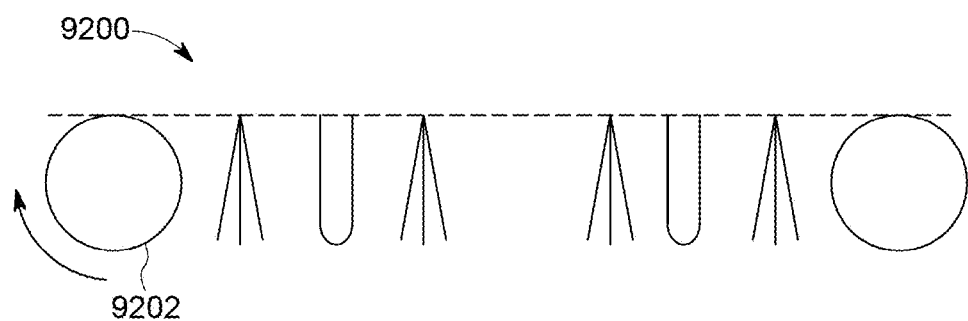
FIG. 92A is an illustration of a side cross-sectional view of yet another illustrative tissue treatment effector.
Figure 92B:
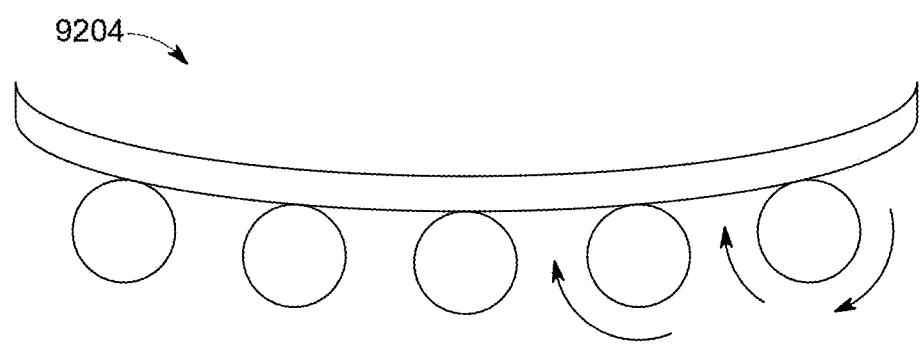
FIG. 92B is an illustration of a side cross-sectional view of yet another illustrative tissue treatment effector.
Figure 92C:
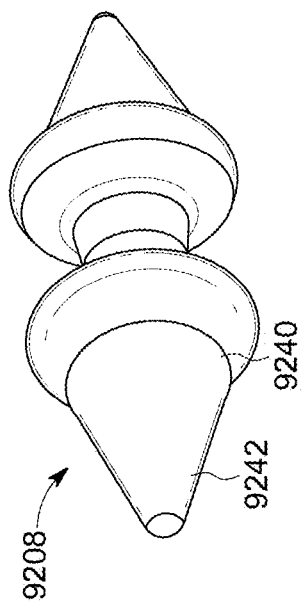
FIG. 92C is an illustration of an isometric view of a tissue treatment element for a fascia tissue treatment device.

It should be appreciated that the shape of the finger members 8608 may be different in other embodiments. For example, the finger members 8608 may be cylinders, polygons, or have any other suitable cross-sectional geometry. The finger members 8608 may include at least one finger member 8206 that rotates or otherwise moves independently from the panel. For example, as shown in FIG. 92A, a tissue treatment assembly 9200 may include at least one finger member 9202 that includes, or is formed as, a roller ball (e.g., a spherical element, etc.) that may rotate independently from the panel (e.g., in a clockwise direction as shown in FIG. 92A, in a counterclockwise direction, etc.). In other embodiments, the roller ball(s) may be stationary with respect to the panel. The roller ball(s) may be included with other finger members of various alternative geometries, thereby enabling the other finger members to perform the fascia tissue treatment and the roller ball(s) to support movement of the finger members 8608 during treatment, for example. In other embodiments, as shown in FIG. 92B, a tissue treatment assembly 9204 may include a plurality of roller ball elements spaced apart along the panel. Referring again to FIG. 86, the finger members 8608 may be tapered and have a larger, first cross-sectional area 8641 near the panel (e.g., at a proximal end of the finger member 8608) and a smaller, second cross-sectional area 8643 away from the panel (e.g., at a distal end of the finger member 8608). For example, as shown in FIG. 92C, at least one finger member (e.g., treatment element 9208) may be shaped as a nugget tip or may be a straight cylindrical finger nub as shown in FIG. 85. In some embodiments, as shown in FIG. 87, the finger members 8708 are individual elements that are spaced apart across the face of the panel.

The finger members may be formed separately from the panel as individual elements that are fastened or otherwise coupled to the panel, or integrally formed with the panel from a single piece of material (i.e., monolithic with the panels). In other embodiments, at least two of the finger members may be integrally formed with one another from a single piece of material. For example, at least two finger members may be formed in a sinusoidal shape from a single piece of material via an injection molding process or another suitable manufacturing process. In some embodiments, the treatment assembly may include multiple subpanels coupled thereto. Each subpanel may include a plurality of finger elements. The subpanels may be circular panels having a smaller diameter than the panel, or may be rings that form a single continuous row of finger members of the panel. The subpanels may be removably coupled to the panel and arrangements of subpanels may be tailored to the treatment needs of the patient.

In some embodiments, the treatment assembly includes other elements beyond the finger members to facilitate or enhance the effectiveness of the treatment. For example, FIG. 87 shows a side cross-sectional view of yet another illustrative treatment assembly 8700 that includes a plurality of finger members 8708 (e.g., a first plurality of treatment elements) and a plurality of secondary treatment elements 8740 in between the finger members 8708. In at least one embodiments, the finger members 8708 and secondary treatment elements 8740 are arranged in alternating concentric rows along the panel (e.g., where each "row" extends along a circumferential direction relative to the central axis of the panel). In other embodiments, the finger members 8708 and secondary treatment elements 8740 are positioned along the same row (e.g., in alternating arrangement along the row, etc.). It should be appreciated that any other arrangement of finger members 8708 and secondary treatment elements 8740 may be used to improve treatment performance.

The secondary treatment elements 8740 may be any form of skin treatment element or device. For example, the secondary treatment elements 8740 may include brush elements 8742 that are configured to engage the skin to remove particles (e.g., dirt, oil, dead tissue, etc.) and/or to facilitate application of a lubricant, lotion, and/or other tissue treatment solution. The brush elements 8742 may also perform other functions such as relaxing a patient's skin at a treatment site, performing micro-dermabrasion, or another use. The bristles of the brush elements 8742 may be made of any suitable material including nylon, polypropylene, horse hair, feather, or any other natural or synthetic filament material.

The tips of the bristles for at least one brush element 8742 may be flocked (split) or unflocked. The tips of the bristles may also be rounded, bulbous, flat, pointed, etc. The bristles may be soft and flexible for a comfortable and soothing treatment, or may be rigid and stiff for a more aggressive tissue treatment. In some embodiments, the bristles include both soft/flexible bristles and rigid/stiff bristles for a combined treatment. In other embodiments, a first brush of the treatment device may have a first type of bristles and a second brush having a different type of bristles. The brush elements 8742 may also have different types of bristles in the same brush elements 8742.

In some embodiments, the secondary treatment elements 8740 form part of a soft tissue stimulation system configured to provide electrical current to the treatment area by placing (i) a plurality of electrodes on the skin surface and (ii) providing electrical impulses via the electrodes to the skin and soft tissue (such as fascia tissue) below the skin's surface, as described above. In some embodiments, the stimulation system employs circuitry and hardware elements that can execute traditional TENS (transcutaneous electrical nerve stimulation) and/or NMES (neuromuscular electrical stimulation) therapy. In such embodiments, at least one lead wire may be electrically coupled to the device, with a transcutaneous electrode at the distal end for delivering the electrical impulses to the patient. The transcutaneous electrode may adhere to the skin. The device may be configured to provide a pre-determined stimulation waveform having a pre-determined frequency (Hz), pulse width (μs), and amplitude (mA). Alternatively the device may be configured to allow a user to modify one or more parameters of the stimulation waveform.

In some embodiments, the electrodes may alternatively be positioned on the panel (e.g., in between finger members along each row, in separate rows from the finger members, etc.). In other embodiments, the electrodes may be positioned on the finger members themselves (e.g., at least one finger member may include an electrode positioned thereon).

Figure 89:
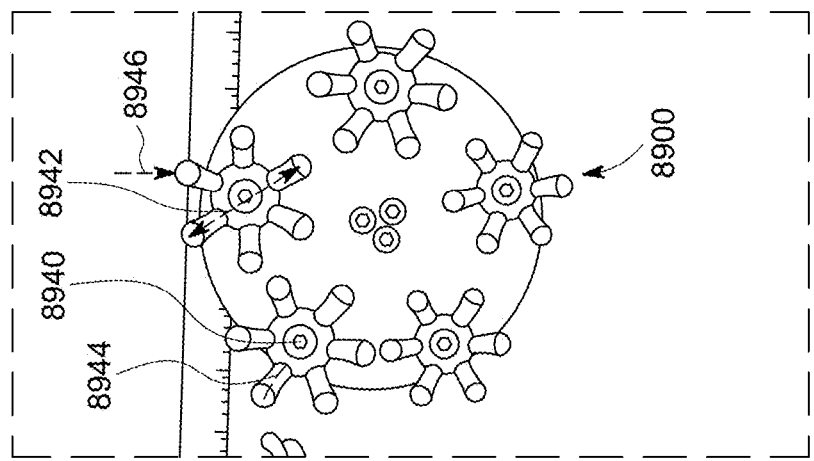
FIGS. 88-91 are illustrations of various illustrative tissue treatment effectors for a fascia tissue treatment device.
Figure 88:
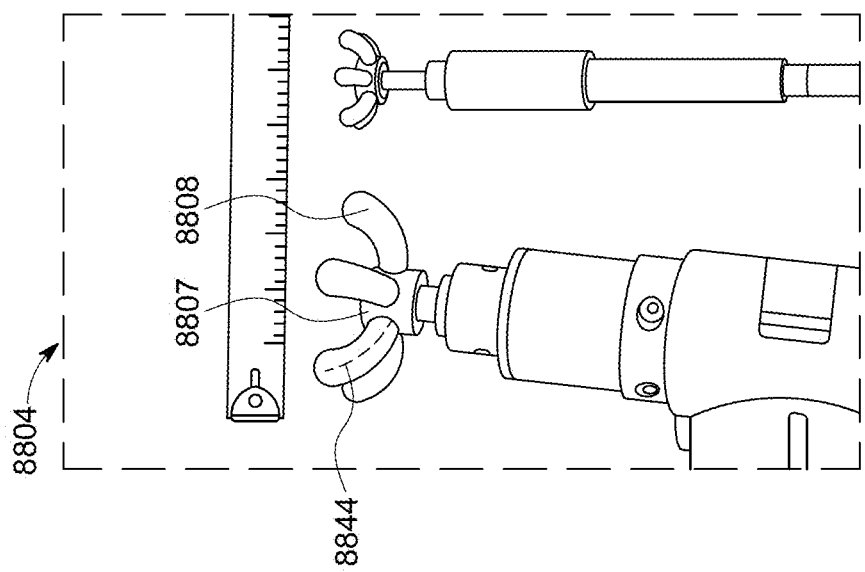
Figure 91:
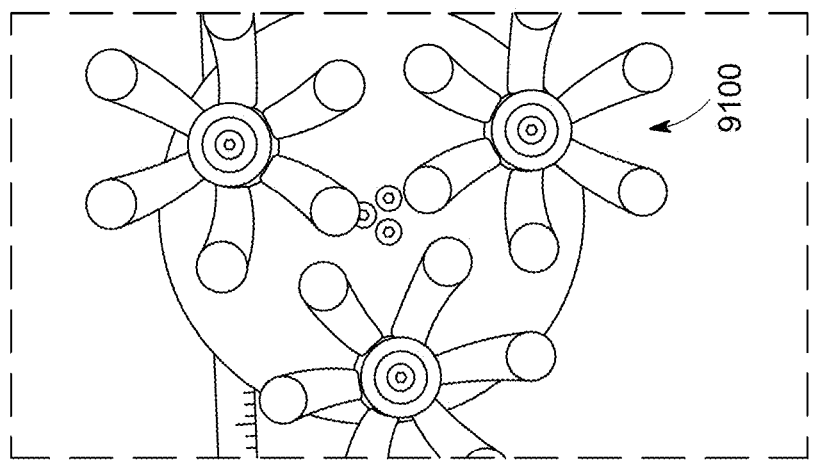
Figure 90:
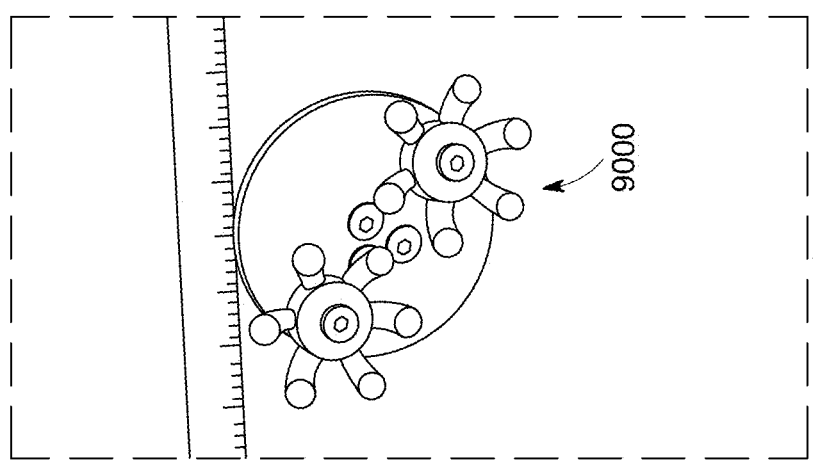

Referring to FIGS. 88-91, various additional illustrative treatment assembly (e.g., effector, etc.) designs are shown. In the embodiment of FIG. 88, the treatment assembly 8804 includes a single tissue treatment element (e.g., flower member, claw, etc.) having a central body 8807 and a plurality of finger members 8808 extending axially and curving radially away from the central body 8807. FIGS. 89-91 each show an illustrative treatment assembly 8900, 9000, 9100 that includes a panel and a plurality of tissue treatment elements coupled to the panel and extending axially away from one side of the panel. The tissue treatment elements may be arranged in at least one ring concentric with a rotational axis of the effector, arranged in rows along a radial direction, or any other suitable arrangement. In one embodiment, and as shown in FIG. 89, the treatment elements are mounted to the panel using a fastener 8940 (e.g., screw, bolt, etc.) extending through the central body of each individual tissue treatment element. In other embodiments, the tissue treatment elements may be glued, welded to the panel, or otherwise coupled to the panel. In yet other embodiments, the tissue treatment elements may be integrally formed with the panel from a single piece of material. The treatment elements, including the finger members, may be formed of metal or another material that may be sanitized after use without damage. In other embodiments, the treatment elements may be formed from acrylic, PVC, hard rubber, or any other material that is stiff and does not cut or scrape skin of a patient on which the effector is being utilized to help treat or adjust fascia tissue. It will be appreciated that alternative numbers of treatment members may be utilized in accordance with the principles of the present disclosure. The treatment elements are also shown to be substantially identical. However, it will be appreciated that alternative configurations of the treatment elements may be utilized to provide for treating different size anatomical regions.

The treatment elements shown in FIG. 89 have an outer diameter 8942 of approximately 1½ inches. However, the outer diameter 8942 of the treatment elements may have a fairly wide range (e.g., ½ inch to 6 inches in diameter, etc.). Illustrative treatment elements shown have a length 8944 about ¾ of an inch long and have heads or tips that have a head diameter 8946 of about ⅜ of an inch. The dimensions and configurations (e.g., curves) of the treatment elements, finger members, and tips of the finger members may vary depending on the anatomical region on which the treatment assembly is to be used. The tips of the finger members may have one or more same or different dimensions as the finger members (e.g., the tips may have a larger diameter by being bulbous). The finger members are shown to be curved. Alternative configurations, such as finger members being straight may be utilized as well. The treatment elements are each shown to be a single member. However, in other embodiments, the treatment elements may be formed from multiple elements. Still yet, rather than the treatment assembly using treatment elements that have a flower, claw, or cactus-like appearance (i.e., central portion with extending finger members), treatment elements with non-flower-like appearance may be utilized, as well, that still provides a user with a number of closely spaced pressure-point elements that can be pressed and guided along a patient's skin to cause fascia tissue to be released or perform a non-therapeutic function. The finger members may be substantially the same length (e.g., less than 0.1 inch difference in length between finger length) such that the tips of the finger members are substantially co-planer and parallel to a support structure (in the case of a flat support structure) so that a pressure load applied to the skin and fascia tissue is substantially equally applied by each of the finger members.

Each of the treatment elements is shown to have six finger members. Alternative numbers of finger members may be utilized in accordance with the principles of the present disclosure. The finger members may be stiff or rigid (e.g., inflexible, etc.), thereby having minimum bend or deformation during usage of the device on fascia tissue of a patient.

The panel may have openings (not shown) defined by the panel through which a screw or other fastening mechanism may extend through treatment elements into the panel. After fastening the treatment elements to the panel, glue or other fastening material, such as epoxy, may be utilized to secure the treatment elements to the panel. A cover (not shown) above the fastening mechanisms may be utilized to limit the ability for someone to access or remove the fastening mechanisms of the treatment elements. Alternatively, the treatment elements may be configured to allow for a user to more easily replace the treatment elements to change size, replace broken flower members, or otherwise.

In an embodiment, the treatment assemblies 8900, 9000, 9100 may be configured such that the tissue treatment elements themselves may spin by themselves or in addition to the panel spinning or being stationary. In an embodiment, the tissue treatment elements may be mounted on rotatable shafts that extend through the panel and are mounted to hubs that secure the shafts to the panel such that the tissue treatment elements are maintained at a fixed vertical position.

Gears may be mounted to the rotatable shafts to cause the tissue treatment elements to spin as other gears apply rotational force to the gears connect to the rotatable shafts. The other gears may be driven by separate motors, a common motor, the same motor that drives the panel to rotate, or otherwise. In an embodiment, all of the tissue treatment elements may be configured to rotate at the same speed. In an alternative embodiment, a portion of the tissue treatment elements may be configured to rotate. In yet another embodiment, some or all of the tissue treatment element(s) may be configured to rotate at different speeds. In an embodiment, rotation of the tissue treatment elements may be selectively turned ON or OFF. In other words, an operator may be able to engage or disengage rotation of tissue treatment elements, as desired. In a stationary or OFF state, the panel may spin or rotate and the tissue treatment elements may remain in a fixed position relative to the panel. In an ON state, the tissue treatment elements may rotate relative to the panel. In an embodiment, speed of rotation may be constant or a motor that drives the gears to which the tissue treatment elements may be selectably altered to operate at different speeds, which may or may not be related to the speed of rotation of the panel. Gear ratio for driving the treatment elements may be set to a speed ranging from 1 revolution per minute (RPM) to 1000 RPMs. Alternative rotational speeds of the tissue treatment elements may be utilized. The gears may be singular or allow for multiple gear ratios.

The tissue treatment elements may be in the shape of a claw having a base with finger members extending therefrom. It should be understood that alternative configurations of the finger members may be utilized. The shapes may have a wide range of geometries that may be configured to perform "fascial shearing" for different layers of fascia tissue. In an embodiment, a tight latex or other material wrap may be applied to the body part in performing the process. The different layers of fascia tissue may be based on the anatomical region at which the fascia tissue is located. For example, fascia tissue on a person's scalp is much closer to the person's skin than fascia tissue on the person's leg or torso. Moreover, the physical dimensions of the patient may also necessitate tissue treatment elements of different configurations. For example, if the patient has minimal body fat (e.g., less than 10% body fat), then the tissue treatment elements may be shorter than if the patient has a lot of body fat (e.g., over 50% body fat). Moreover, a patient with higher density of muscle (e.g., young male who in good physical condition) may also demand tissue treatment elements that have tips with a broader circumference than a patient with less density of muscle (e.g., senior female). Hence, the configuration of the tissue treatment elements may vary considerably for different patients.

Although tissue treatment elements that are rigid with rigid finger members (i.e., finger members and base members) may be utilized in some embodiments, finger members with some amounts of compliance (i.e., bendable or rotatable) are possible. Such compliant finger members may be possible with finger members formed of certain flexible material (e.g., rubber, silicone, etc.) or are mounted to the base member via a flexible member of attachment mechanism. Although some compliance may be provided, the tissue treatment elements may be configured to treat fascia tissue at particular anatomical regions and possibly of particular type. For example, fascia tissue on a person's forehead may be treated with tissue treatment elements with different configurations than fascia tissue on a person's cheek or neck. Although the finger members shown have an arcuate shape extending between the proximal end at the panel and distal end at the tip with a fairly uniform diameter shaft between the proximal and distal ends, it should be understood that a wide variety of shapes of finger members may be utilized. For example, the diameter between the proximal end and tip may vary from a first diameter at the proximal end to a second diameter at the distal end, where the first diameter is larger than the second diameter. The transition between the first and second diameters may be smooth with no discontinuities or the transition may be more abrupt (e.g., step between two or more diameters along the length of the shaft of the finger members).

Curvature or other configuration of the finger members may vary between different treatment assemblies such that an operator may select from amongst several different treatment assemblies based on the patient (e.g., high body fat versus low body fat), depth of fascia and/or type of fascia at an anatomical region being treated, speed of the rotation of the treatment assembly. It should be understood that the various configurations of the finger members being described with regard to the tissue treatment elements may be applied to finger members that are directed connected to a panel, such as shown in FIGS. 76-87.

Referring to FIG. 92, another illustrative treatment element structure is shown (treatment element 9208) that may be used in place of one or more finger members of the treatment assembly, and/or as a standalone treatment element 9208 that may be used by the treatment device to manipulate fascia tissue. In the embodiment shown, the treatment element 9208 is a refining tool that is used to target small or stubborn areas of fascia tissue. The treatment element 9208 includes a base 9240 and a conically-shaped extension 9242 engaged with and extending away from the base 9240. The treatment device (e.g., actuator) may be configured to press a tip of the conically-shaped element into a patient's tissue and then move the treatment element 9208 along a circular path to work the affected area. In other embodiments, the treatment device (e.g., actuator) may be configured to rotate the tip of the treatment element 9208 by pivoting the element from the base 9240. It will be appreciated that various treatment element shapes and sizes may be used in other embodiments.

Figure 94:
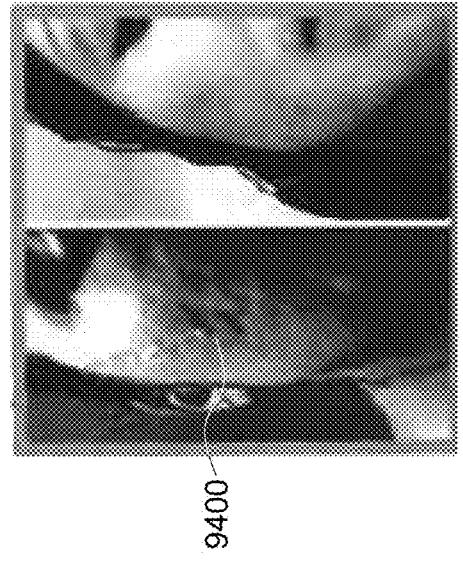
FIGS. 93-100 and 119 are various before and after photographs of patients after using a fascia tissue therapy system.
Figure 93:
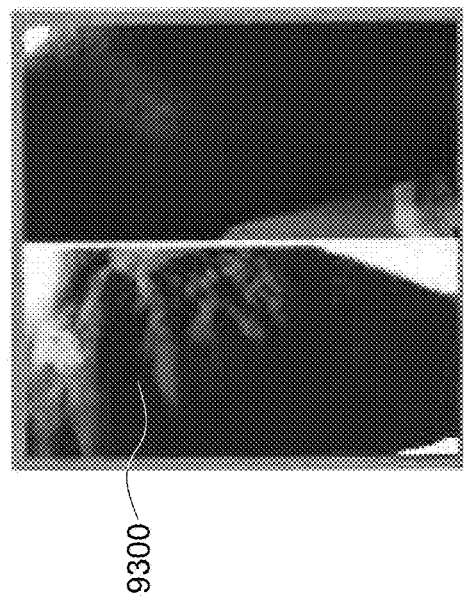
Figure 96:
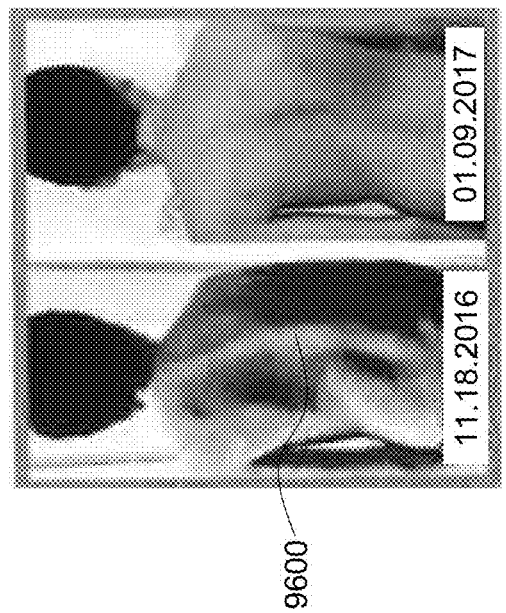
Figure 95:
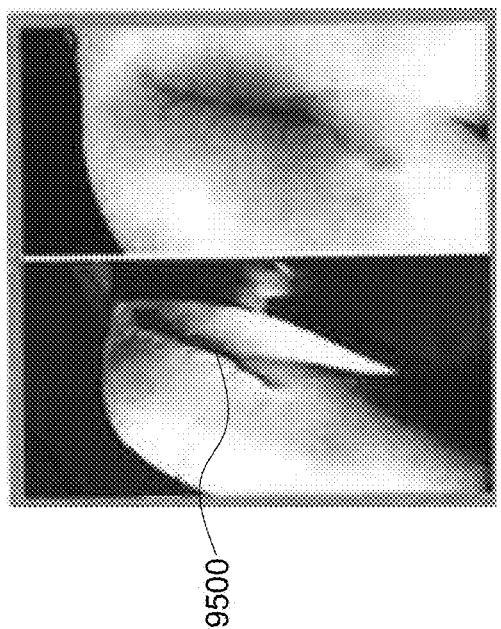
Figure 97:
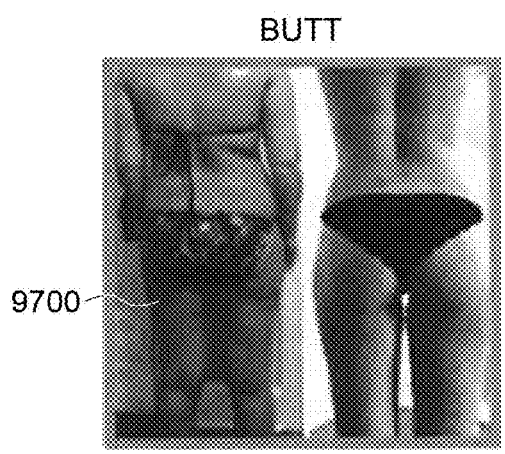
Figure 98:
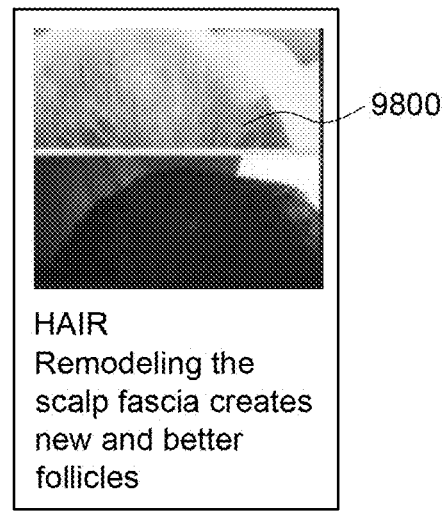
Figure 99:
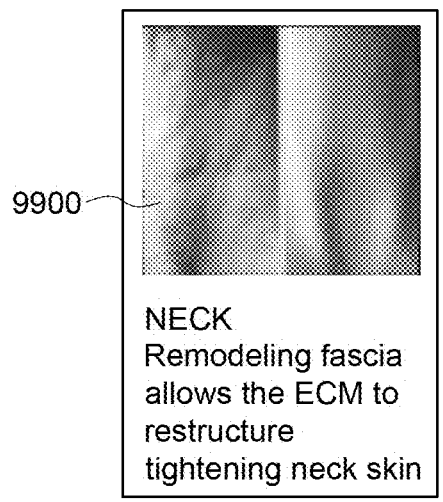
Figure 100:
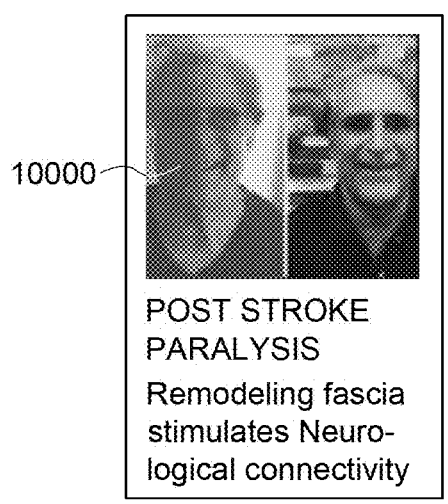
Figure 102C:
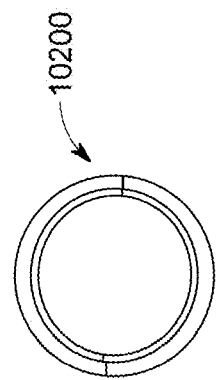
FIGS. 102A-102F are illustrations of perspective, another perspective, top, side, front, and bottom views of yet another illustrative fascia tissue therapy system.
Figure 102F:
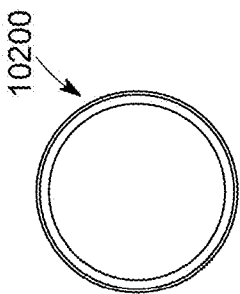
Figure 102E:
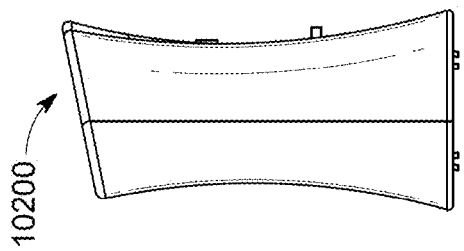
Figure 102D:
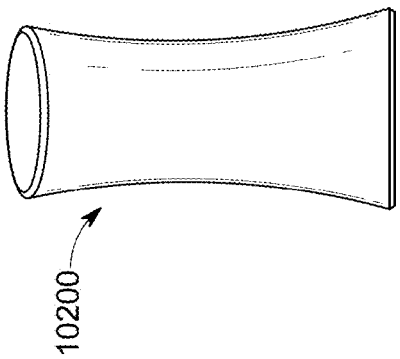
Figure 102A:
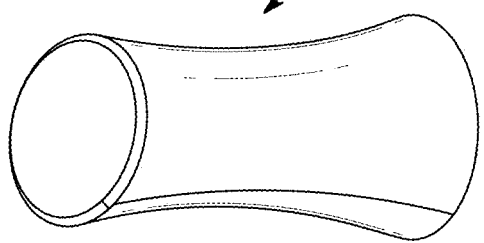
Figure 102B:
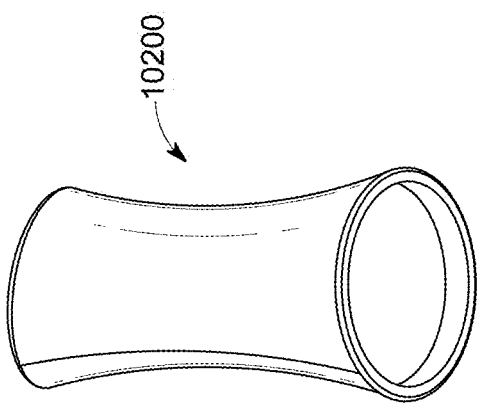
Figure 103B:
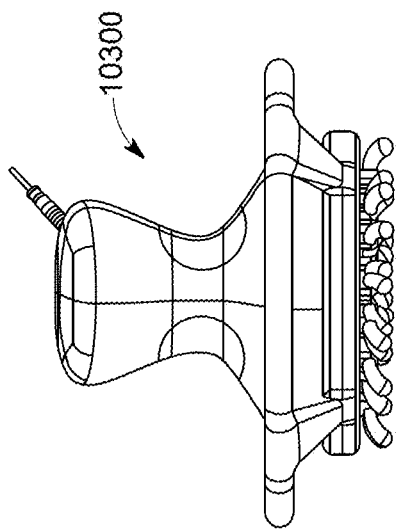
Figure 103D:
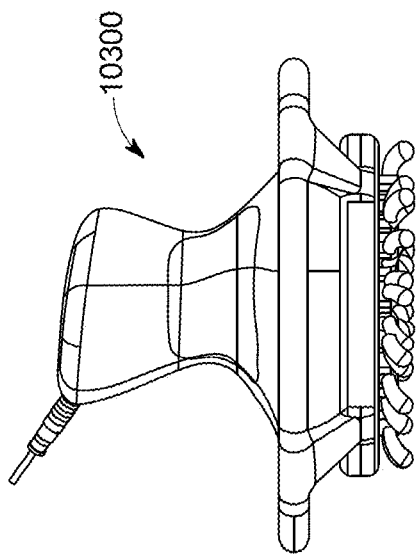
Figure 103A:
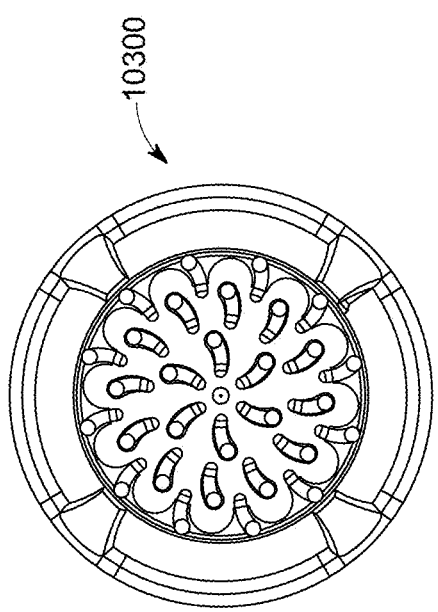
Figure 103C:
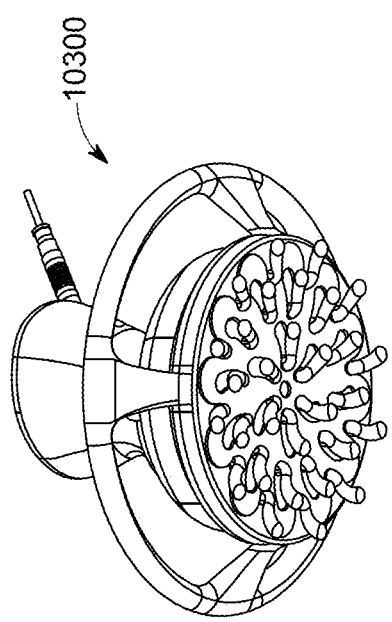
Figure 105A:
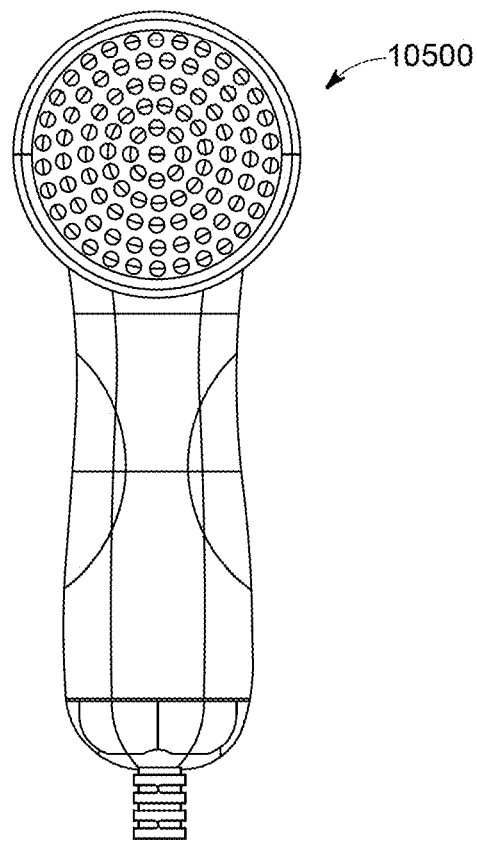
Figure 105B:
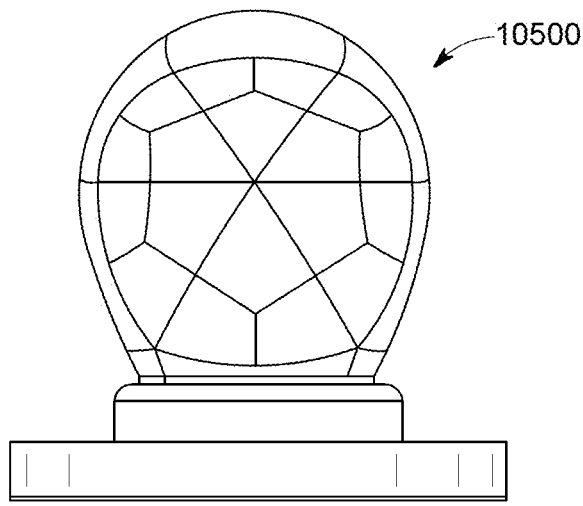
Figure 105C:
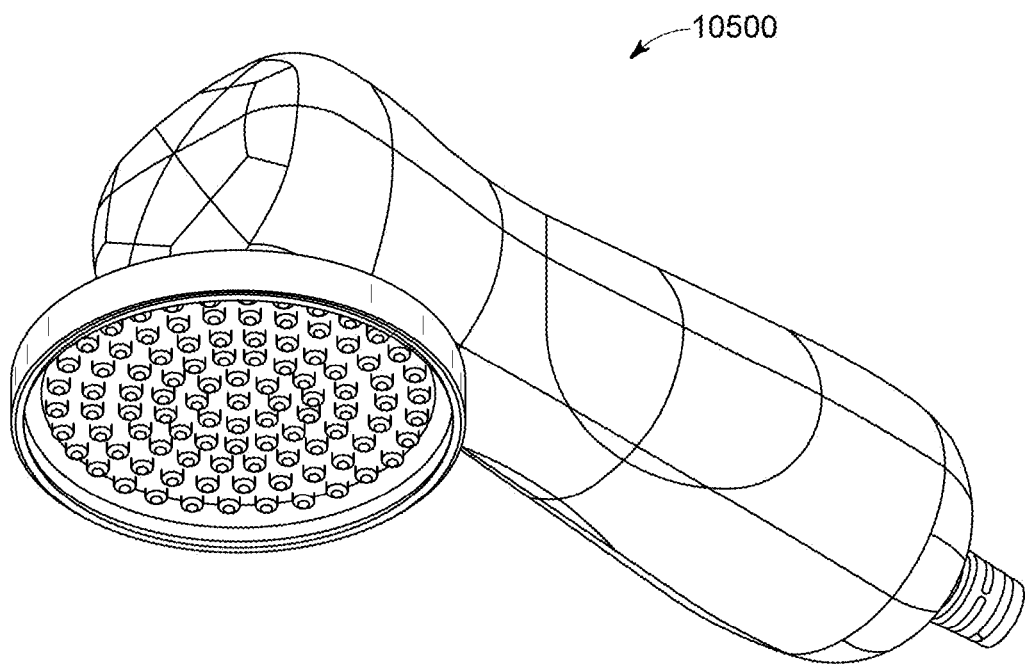
Figure 105D:
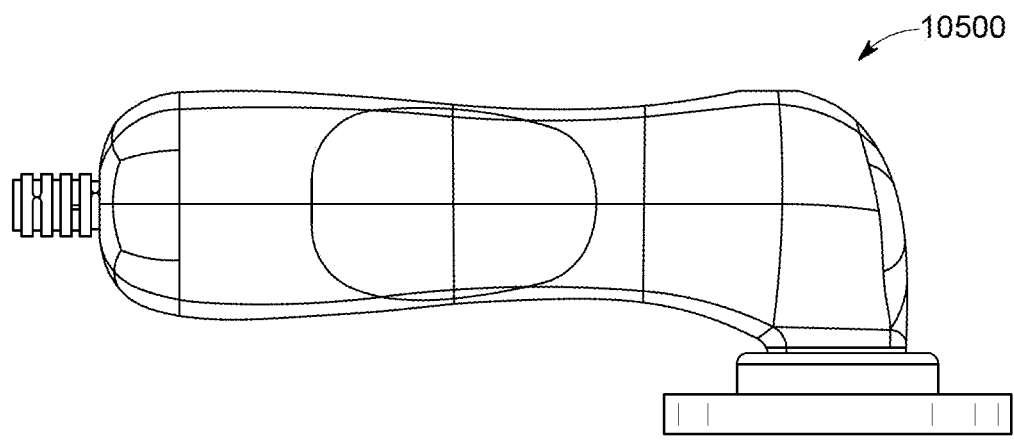
Figure 106B:
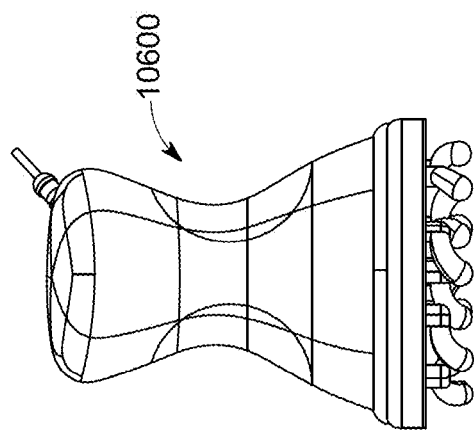
FIGS. 106A-106G are illustrations of bottom, front, perspective, left, rear, right, and top views of yet another illustration fascia tissue fitness device.
Figure 106D:
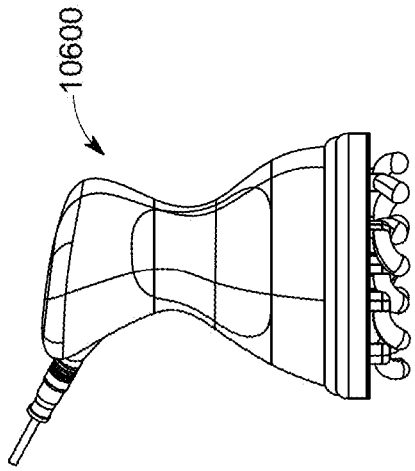
Figure 106A:
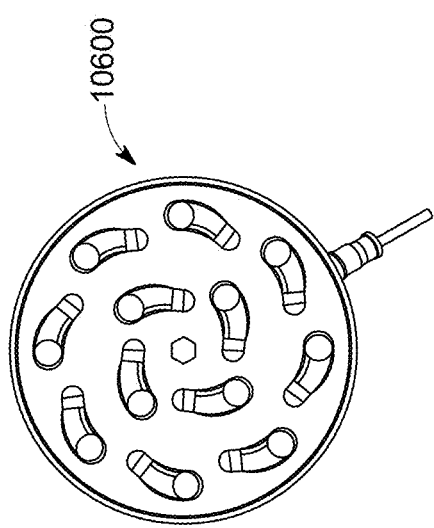
Figure 106C:
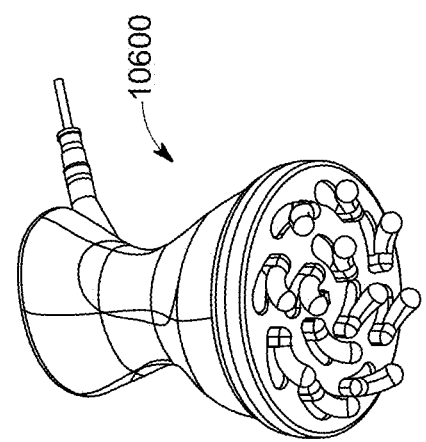
Figure 106F:
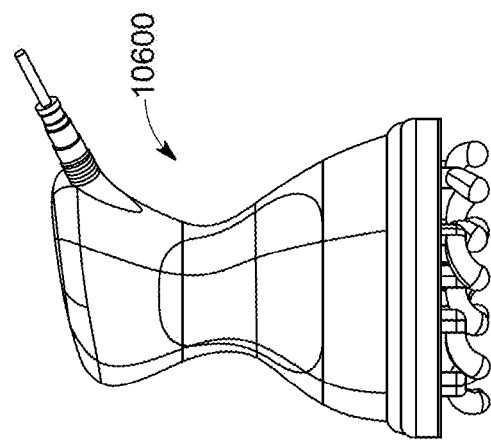
Figure 106G:
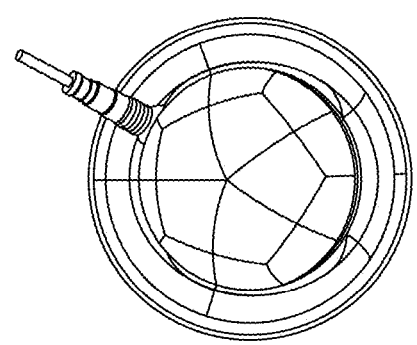
Figure 106E:
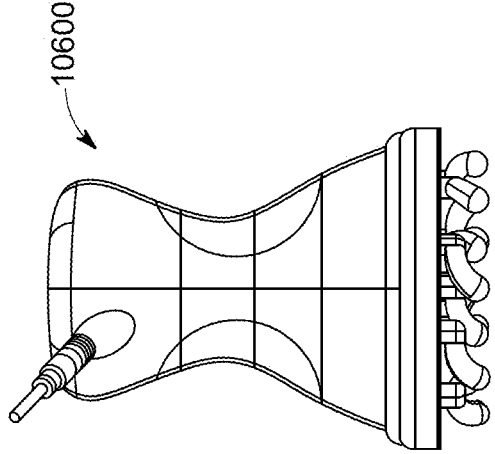
Figure 107A:
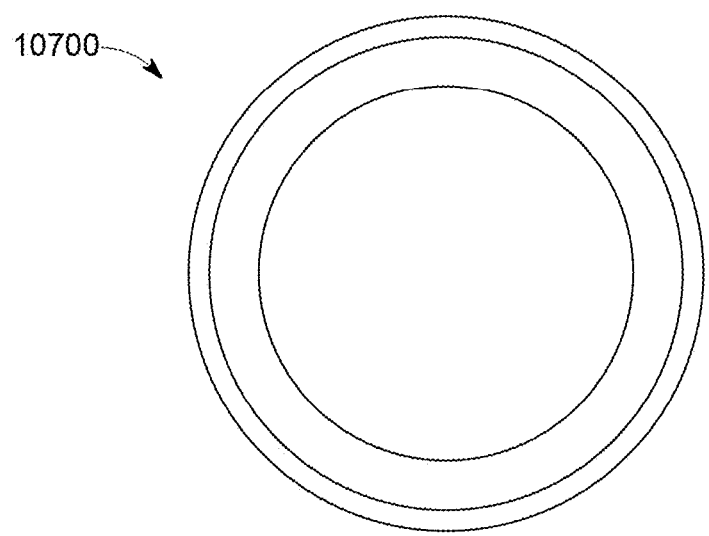
FIGS. 107A-107G are illustrations of bottom, front, perspective, left, rear, right, and top views of yet another illustrative fascia tissue fitness device.
Figure 107B:
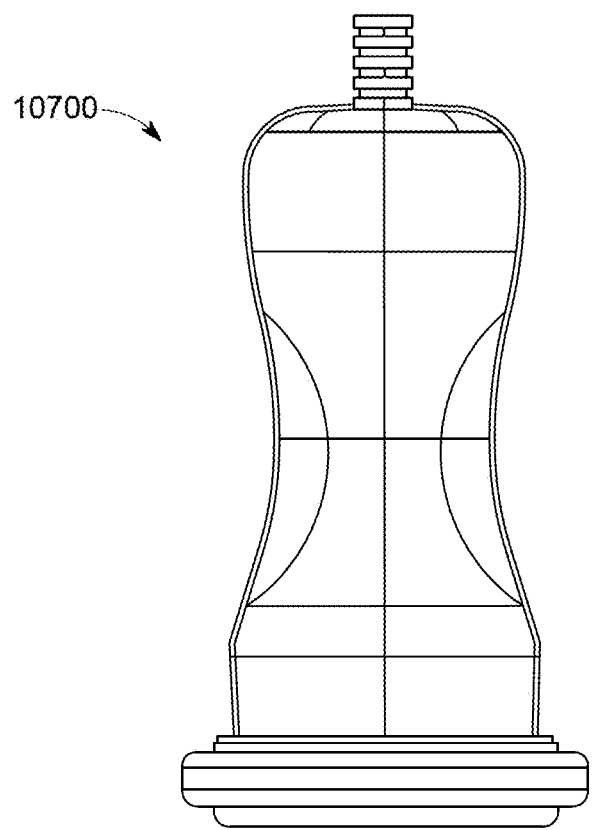
Figure 107C:
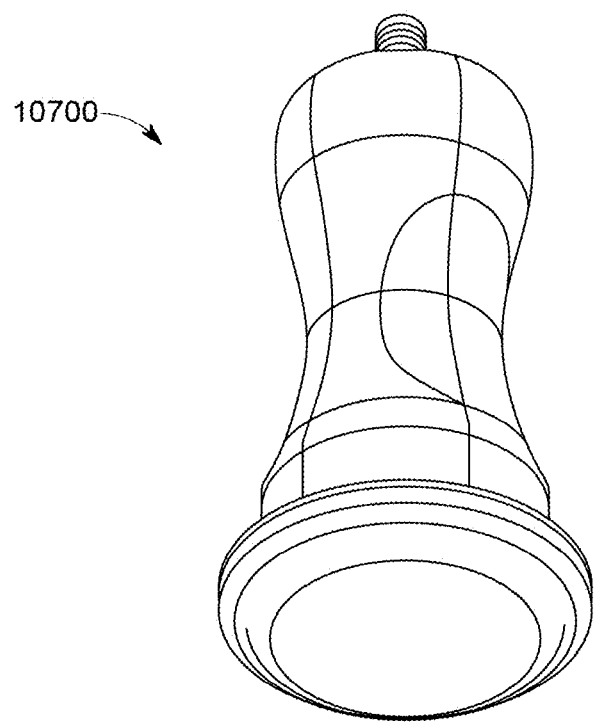
Figure 107D:
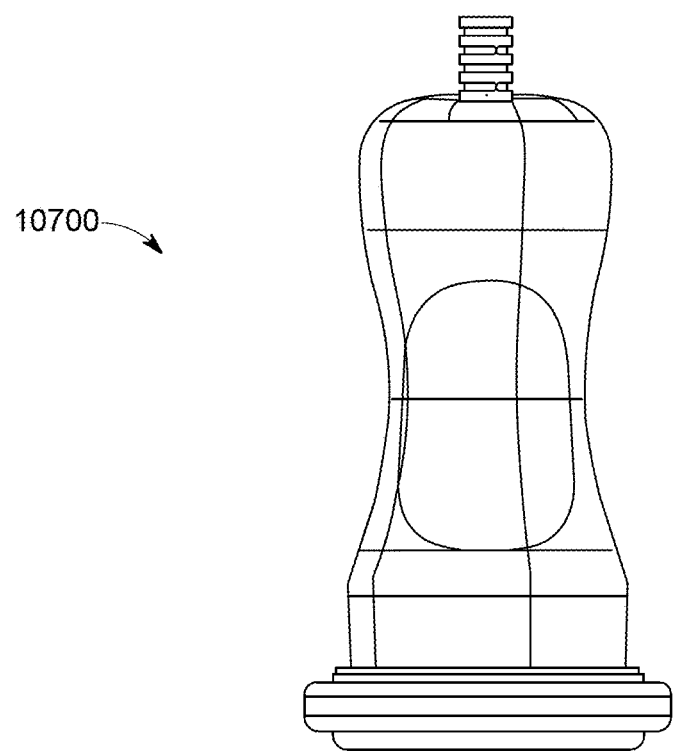
Figure 107E:
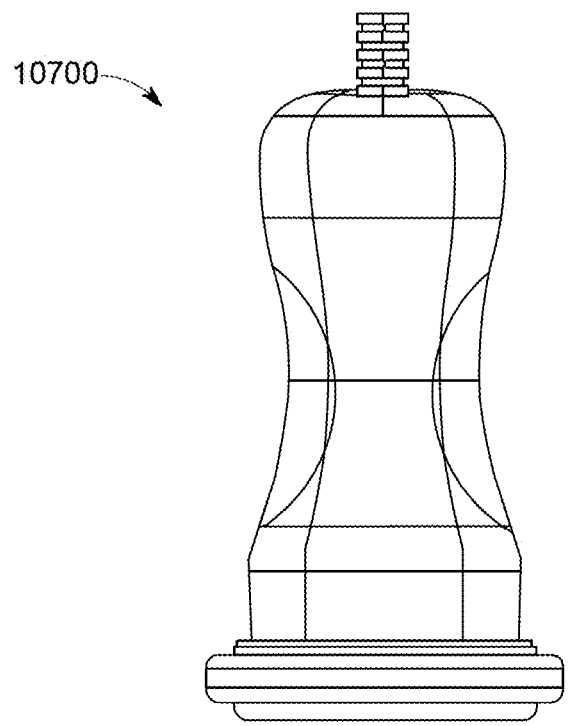
Figure 107F:
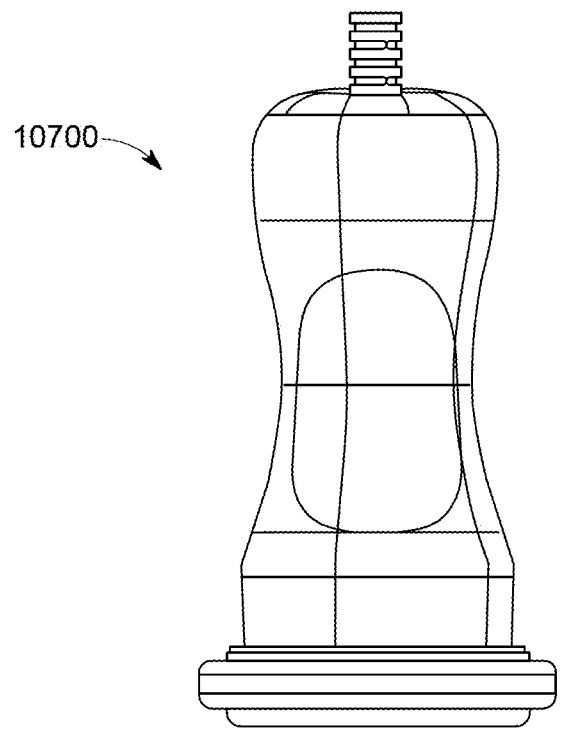
Figure 107G:
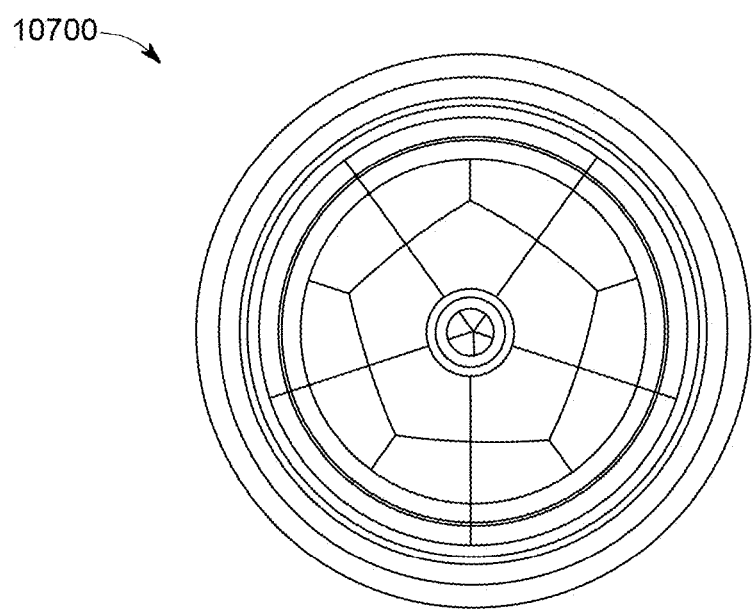
Figure 108A:
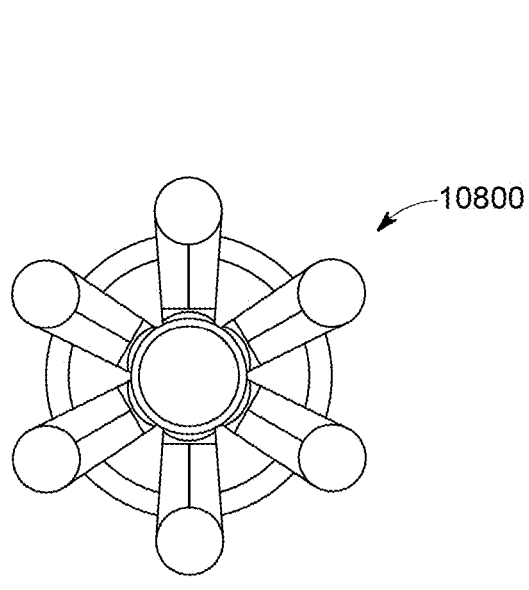
FIGS. 108A-108G are illustrations of bottom, front, perspective, left, rear, right, and top views of yet another illustrative fascia tissue fitness device.
Figure 108B:
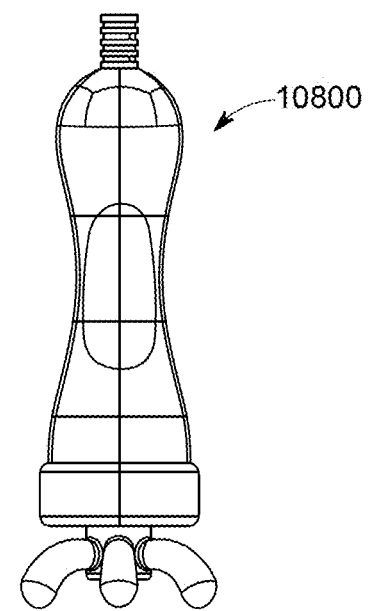
Figure 108C:
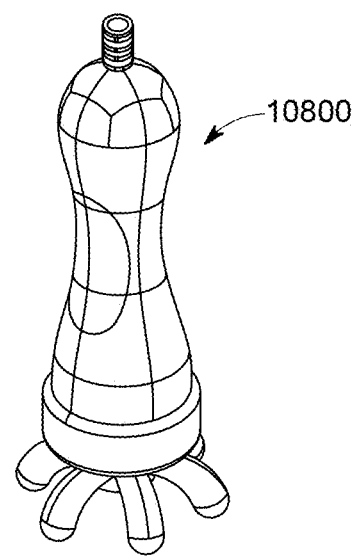
Figure 108D:
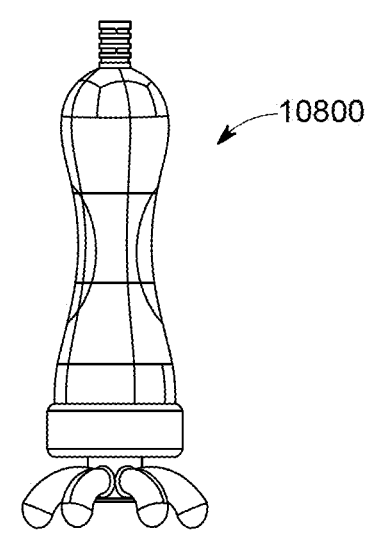
Figure 108F:
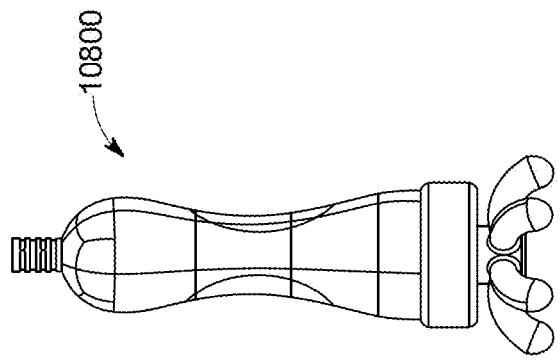
Figure 108G:
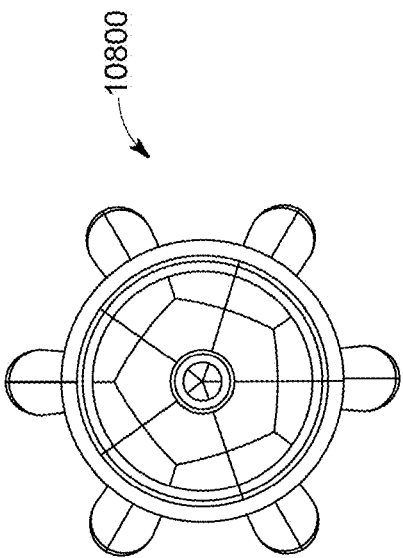
Figure 108E:
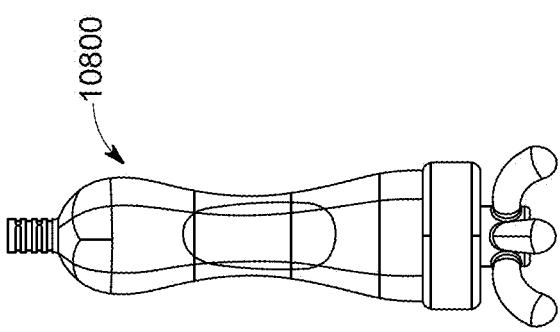
Figure 109B:
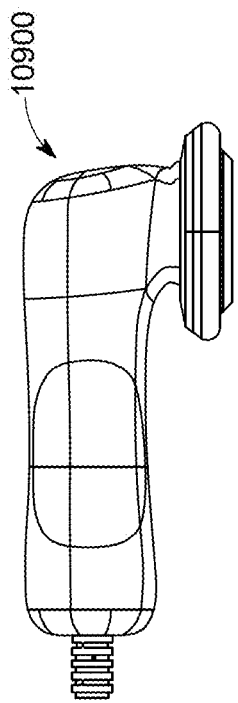
FIGS. 109A-109G are illustrations of bottom, front, perspective, left, rear, right, and top views of yet another illustrative fascia tissue fitness device.
Figure 109D:
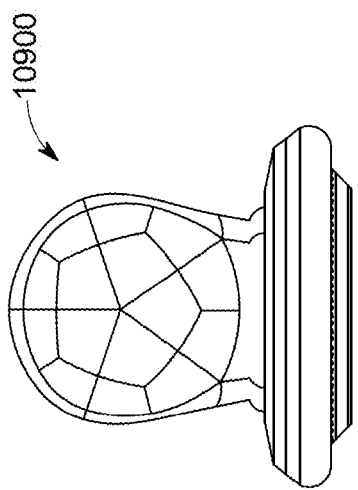
Figure 109A:
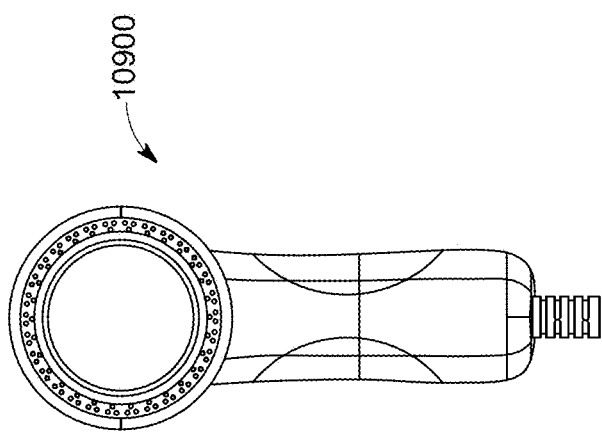
Figure 109C:
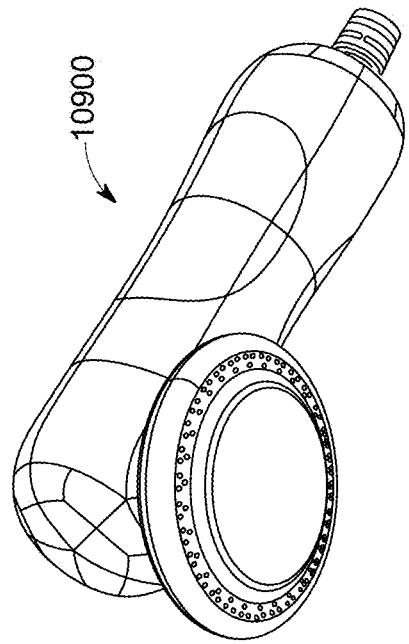
Figure 109F:
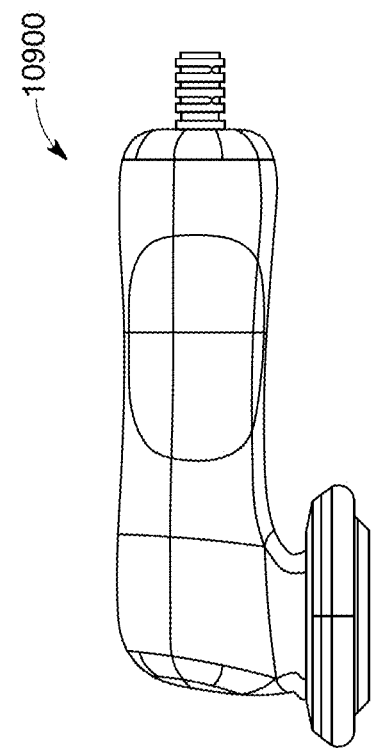
Figure 109G:
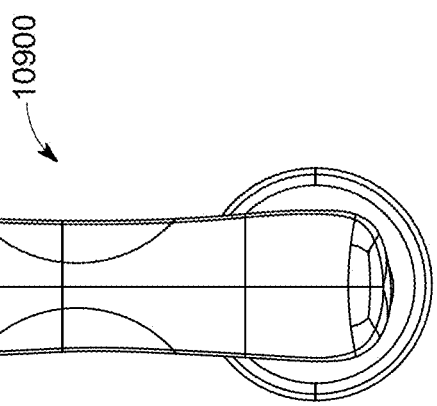
Figure 109E:
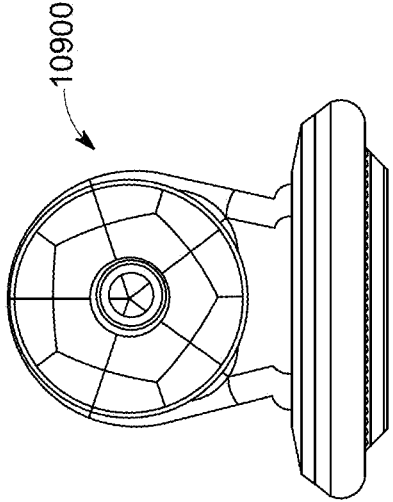
Figure 119:
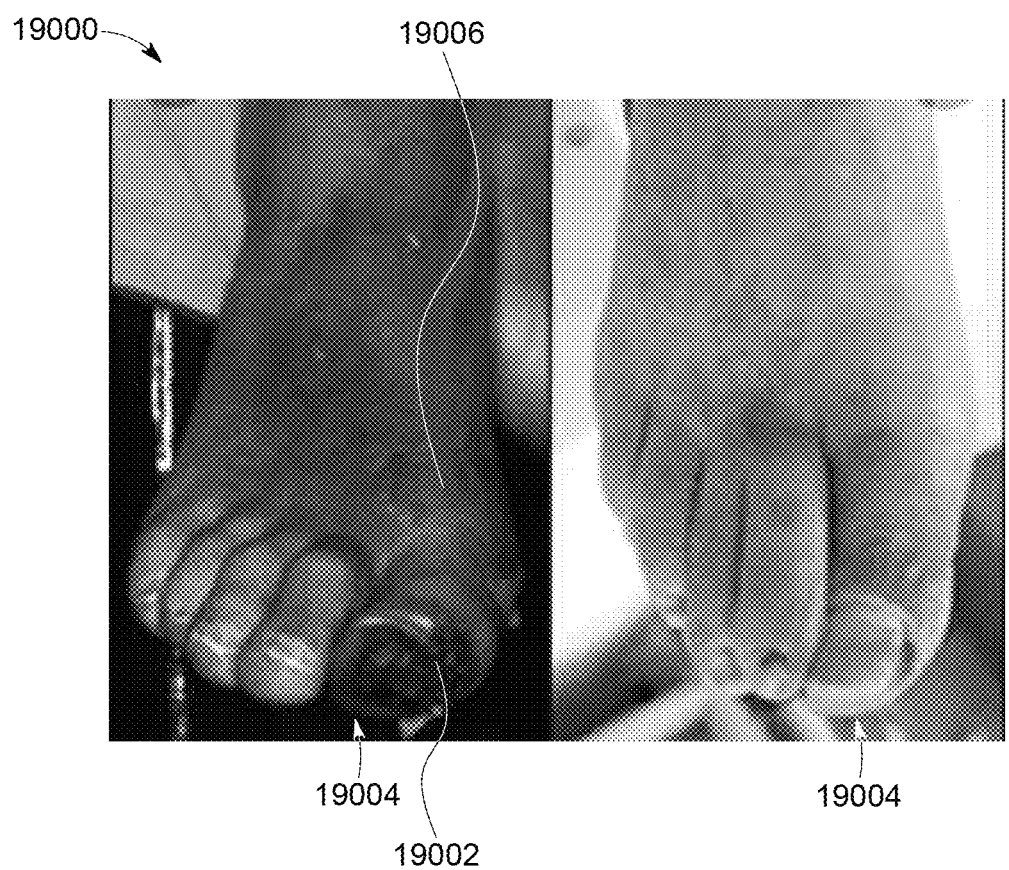

While certain features of the treatment device (e.g., therapy device, etc.) are configured to be optimal usage on fascia tissue, the features also provide for ornamental appearance. It should be understood that the treatment device may be used for increasing overall myo-fascial fitness to loosen fascia tissue that is constrained, improve health and/or beauty purposes (e.g., provide a satisfactory feeling to a user and/or alter the appearance of cellulite and skin smoothness). Moreover, usage of the fascia tissue fitness device may open, loosen, restore, and/or revitalize fascia tissue of men and women, young and old. FIGS. 96-100 show photographs demonstrating some of the various benefits that can be provided by using the treatment system (e.g., therapy system, etc.). For example, FIG. 93 shows a significant reduction in the amount of cellulite 9300 presenting through a patient's skin along a leg after treatment. The treatment system can also be used to treat acne 9400 (FIG. 94), scar tissue 9500 (FIG. 95), and/or other dermatological conditions. FIG. 96 shows improvements in patients that are suffering from scoliosis 9600 and/or other forms of postural misalignment. The treatment system can be used to redistribute fatty tissues 9700 (FIG. 97), promote and restore hair growth (FIG. 98) (e.g., improving blood circulation to hair follicles 9800, reducing stress on tissue from realignment of the fascia layers, etc.), restructure and remodel fascia (e.g., neck skin 9900, etc.) to improve skin tightening (FIG. 99) in different body areas, and to stimulate neurological connectivity and/or improve motor control for patient's suffering from paralysis 10000 (e.g., as a result of a stroke as shown in FIG. 100 or other injury). For people with underlying health conditions, such as diabetes, the system may be used to improve circulation to extremities, such as feet and hands, to improve circulation thereto. As shown in FIG. 119, before and after photos of (i) a foot 19000 having poor circulation such that necrosis 19002 has set in on the big toe 19004 and skin 19006 on the remainder of the foot is showing significant cellular damage, and (ii) the foot 19000 after fascia tissue treatment such that circulation has improved and the skin on the big toe 19004 and rest of the foot 19000 shows significant amounts of improvement to the point that amputation has been averted.

While various embodiments of the treatment system have been described in the context of use in medical environments, it will be appreciated that the treatment system may be also used in other applications. For example, the treatment system could be installed in a workout and/or training facility and used as part of a person's workout regimen, to improve physical appearance, stimulate blood flow, and/or improve recovery times. A miniaturized version of the treatment system could also be used for home use or in various other applications. Data from the computing device could be transmitted wirelessly to a personal device (e.g., smart phone, tablet, etc.) for additional review and analysis through applications installed on the user device (e.g., software as a service, etc.). The application may be configured to ensure compliance with health information privacy policies (e.g., the health insurance portability and accountability act (HIPPA), etc.) and may limit user access to certain data.

FIGS. 101A-101F are illustrations of perspective, another perspective, top, side, front, and bottom views of yet another illustrative fascia tissue treatment system 10100.

FIGS. 102A-102G are illustrations of perspective, another perspective, top, side, front, and bottom views of yet another illustrative fascia tissue treatment system 10200.

FIGS. 103A-103G are illustrations of bottom, front, perspective, left, rear, right, and top views of yet another illustrative fascia tissue treatment device 10300.

FIGS. 104A-104G are illustrations of bottom, front, perspective, left, rear, right, and top views of yet another illustrative tissue treatment assembly 10400.

FIGS. 105A-105G are illustrations of bottom, front, perspective, left, rear, right, and top views of yet another illustrative fascia tissue treatment device 10500. The fascia tissue treatment device 10500 may include LED lights that are used for heating up fascia tissue of a patient.

FIGS. 106A-106G are illustrations of bottom, front, perspective, left, rear, right, and top views of yet another illustration fascia tissue treatment device 10600.

FIGS. 107A-107G are illustrations of bottom, front, perspective, left, rear, right, and top views of yet another illustrative fascia tissue treatment device 10700. In this case, the fascia tissue treatment device 10700 may be an ultrasound device configured to generate (and optionally receive) ultrasound signals. The ultrasound signals may be used for causing fascia tissue to be stimulated, thereby loosening up the fascia tissue prior to or during treatment. If the ultrasound device includes an ultrasound sensor, then ultrasound images of fascia and other tissue may be captured by the sensor and used to manage current and future treatments, for example, along with storing images for a medical professional to review current status, progress from previous treatments, and projecting and planning future treatments.

FIGS. 108A-108G are illustrations of bottom, front, perspective, left, rear, right, and top views of yet another illustrative fascia tissue treatment device 10800. In this case, the tissue treatment element of the treatment device 10800 includes a single "claw" that includes fingers that have an arc so as to apply vertical pressure to skin of a patient, thereby allowing for deeper penetration into fascia tissue. Alternative sizes and numbers of claws may be utilized. In an alternative embodiment, rather than the fingers extending from side walls of a central extension member, fingers may extend directly from a base plate and maintain a same curved, vertical orientation for applying pressure to a patient.

FIGS. 109A-109G are illustrations of bottom, front, perspective, left, rear, right, and top views of yet another illustrative fascia tissue treatment device 10900. In this case, the fascia tissue treatment device 10900 may be an RF device that include RF LEDs that heat up fascia tissue of a patient. The treatment device 10900 may also include an ultrasound signal generator, thereby enabling a combination of treatments (i.e., RF and ultrasound). It should be understood that additional treatment signaling, such as low current signals, may also be applied by the fascia tissue fitness device, and an operator may select one or more of the treatments to be performed simultaneously.

Figure 110:
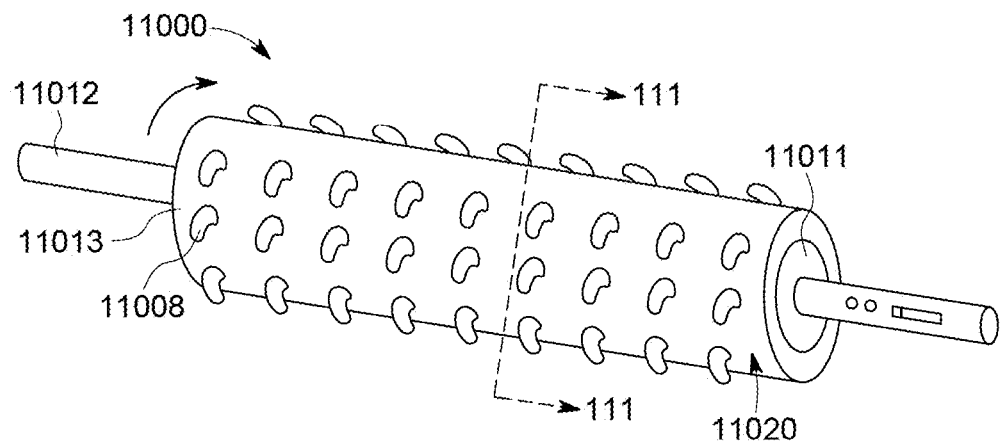
FIG. 110 is an illustration of an isometric view of yet another illustrative fascia tissue treatment device.

FIG. 110 shows a perspective view of yet another illustrative fascia tissue treatment device 11000. The treatment device 11000 is configured to rotate a panel 11020 (e.g., a tubular member, etc.) on which finger members 11008 are connected that extends at least partially along an axial direction so as to move the finger members 11008 toward and away from the surface of the patient's skin so that only a portion of the finger members 11008 may be engaged with the skin at an instant in time.

As shown in FIG. 110, the treatment device 11000 may include a base 11011 including handles 11012 and a movable and rotatable element 11013 supported by the base 11011. In one embodiment, the movable element 11013 is disposed between the handles 11012. In other embodiments, the base 11011 includes only a single handle 11012 on one side of the movable element 11013. The handles 11012 may be tubular or have any other configurations to enable a user (e.g., treatment professional) to handle and maneuver the device while performing a treatment. The shape of the treatment device 11000 may allow for treatment in areas that are more difficult to access using other treatment assembly (e.g., effector, etc.) designs.

The movable element 11013 may include a cylindrical sleeve that extends axially in between the handles 11012. The sleeve is rotatably coupled to or supported by the base 11011 and is arranged coaxially with the base 11011 and handles 11012. The movable element 11013 also includes a plurality of finger members 11008 that are coupled to the sleeve and extend away from an outer surface of the sleeve. The finger members 11008 may extend radially or at an angle, and may be straight or curved (e.g., the finger members 11008 may extend along a circumferential direction relative to a central axis of the panel, etc.). In at least one embodiment, the finger members 11008 are arranged in substantially linear rows along the sleeve (e.g., between opposing ends of the sleeve). In other embodiments, the finger members 11008 may be staggered or disposed in any other desired arrangement along the sleeve. In the embodiment of FIG. 101, the finger members 11008 curve away from a direction of rotation of the sleeve, along a circumferential direction (e.g., counterclockwise when viewed from the side of the sleeve). In other embodiments, the finger members 11008 may curve toward the direction of rotation (e.g., counterclockwise when viewed from the side of the sleeve). It should be appreciated that the direction of rotation of the sleeve may be controlled by a user (e.g., clockwise or counterclockwise depending on the desired treatment and/or user preferences).

The finger members 11008 may be formed separately from the sleeve and coupled to the sleeve using screws, adhesive products, and/or another suitable fastener. In other embodiments, the finger members 11008 may be integrally formed with an outer portion of the sleeve from a single piece of material. For example, the finger members 11008 may be injection molded or otherwise formed onto a flat surface of a formable material, such as plastic, that can be heated and rolled back onto itself to form the outer portion.

As the sleeve rotates, each row of finger members 11008 moves in a circumferential direction around a central axis of the sleeve to periodically engage the patient's skin. The cylindrical roller arrangement of the movable element 11013 allows for approximately uniform application of treatment across large body areas such as the legs and back. The cylindrical roller arrangement also contours to body areas near joints, such as the back of the leg at the knee and/or the elbow pit on an anterior side of a patient's arm.

As shown in FIG. 110, the base 11011 may include a user interface to facilitate control of the fascia tissue treatment device 11000. The user interface may include actuator(s) (e.g., switches, knobs, capacitive sensors, levers, etc.) to allow the user to control rotation of the sleeve relative to the base 11011 (e.g., operating speed, torque, rotational direction, etc.).

Figure 111:
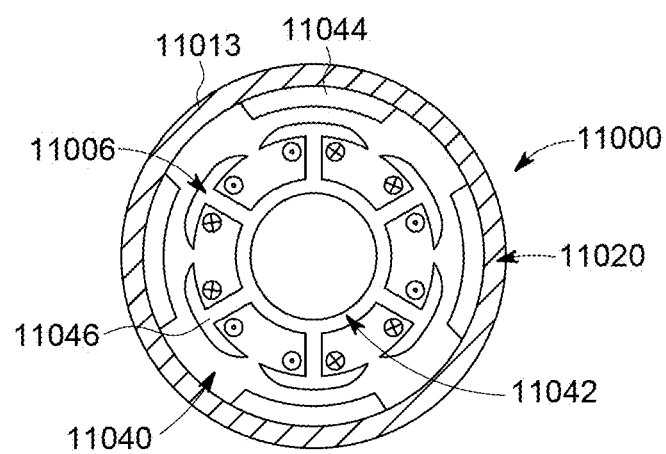

FIG. 111 shows a side cross-sectional view through the sleeve and the base 11011. The sleeve defines a cavity 11040 that may be tubular shaped and that extends longitudinally between the handles 11012. A central portion of the base 11011 is disposed within the cavity 11040. The sleeve completely surrounds (e.g., circumscribes, etc.) the base 11011 along a central portion of the base 11011 between the handles 11012. In some embodiments, the treatment device 11000 includes at least one bearing (e.g., ball bearing, roller bearing, etc.) engaged with the base 11011 and the sleeve to support the sleeve and allow movement of the sleeve relative to the base 11011. The bearings may be sized to accommodate radial loading due to applied pressure between the sleeve (e.g., finger members) and a patient's skin. In some embodiments, the bearings may be sealed and/or self-enclosed bearings to eliminate the need for periodic lubrication and to prevent ingestion of dirt or other debris.

Continuing with FIG. 111, the treatment device 11000 may further include an actuator 11006 to cause rotation of the sleeve with respect to the base 11011. The actuator 11006 may be an electric motor that is separate from the base 11011 and the sleeve. The electric motor may be a direct drive motor 11042 (e.g., a brushless direct current (BLDC) motor, an AC synchronous motor if powered via tether to the base station, or another suitable motor type) that engages the sleeve and/or base 11011 without any intervening transmission or gear set. In other embodiments, the actuator 11006 includes another form of electromechanical, electromagnetic, pneumatic, hydraulic, or other device. In at least one embodiment, the actuator 11006 is disposed at least partially within the cavity 11040 or at the end(s) of the sleeve and is at least partially concealed by the sleeve. In other embodiments, the actuator (e.g., the electric motor) is at least partially formed by the sleeve and the base 11011. For example, the sleeve may form part of a rotor 11044 of the actuator 11006 and the central portion of the base 11011 at least partially forms a stator 11046 of the actuator 11006.

In some embodiments, the treatment device 11000 further includes a control system to selectively power electrical coils of the stator 11046 and/or rotor 11044 based on the relative position between the sleeve and the central portion. The control system may include a controller and at least one sensor (e.g., a Hall Effect sensor, optical sensor, etc.) coupled to the controller to determine a rotational position of the sleeve relative to the stator 11046. The control system may further include a user interface to control operation of the treatment device 11000. As shown in FIG. 110, the user interface may be disposed on at least one handle 11012 of the treatment device 11000. In other embodiments, the user interface may be integrated with or accessible from the control system of the base station.

In embodiments where the treatment device 11000 is portable and/or detachable from the base station, the treatment device 11000 may further include a power source (e.g., battery), which may be disposed within the handles 11012 or in the cavity 11040. Beneficially, integrating the motor with the sleeve and the base 11011 can reduce the size and weight of the powered treatment device 11000. The direct drive motor configuration can also reduce heat produced by the treatment device 11000 and wear on the internal components. In other embodiments, power via a cable may be connected to one or both handles 11012 of the treatment device 11000.

Figure 112:
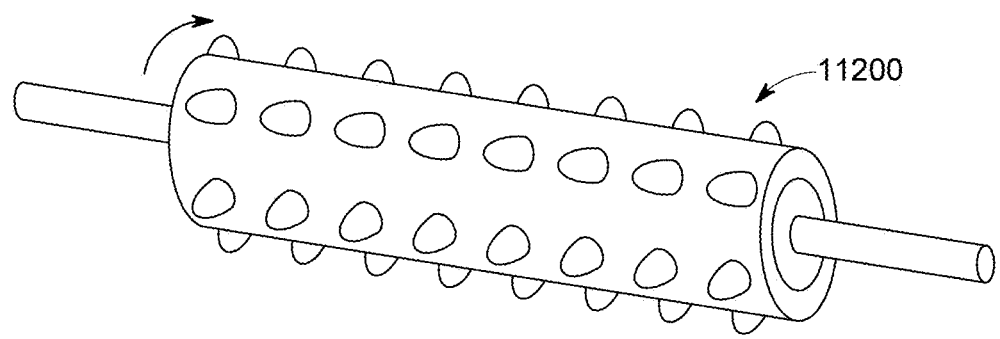
FIG. 112 is an illustration of an isometric view of yet another illustrative fascia tissue treatment device.

It should be appreciated that the geometry of the device (e.g., sleeve, finger members, etc.) may be different in other embodiments. For example, FIG. 112 shows yet another illustrative powered tissue treatment device 11200 that includes finger members in the form of tapered nubs that extend substantially radially away from the sleeve (instead of curving along a circumferential direction as described with reference to FIG. 110). In other embodiments, the shape, size, and/or position of the finger members along the sleeve may be different. In yet other embodiments, the sleeve may include a flexible belt that is fastened around the base or an outer roller for the sleeve. In this way, other shapes can also be used for the sleeve (e.g., an oval shape, racetrack shape, etc.).

Figure 113:
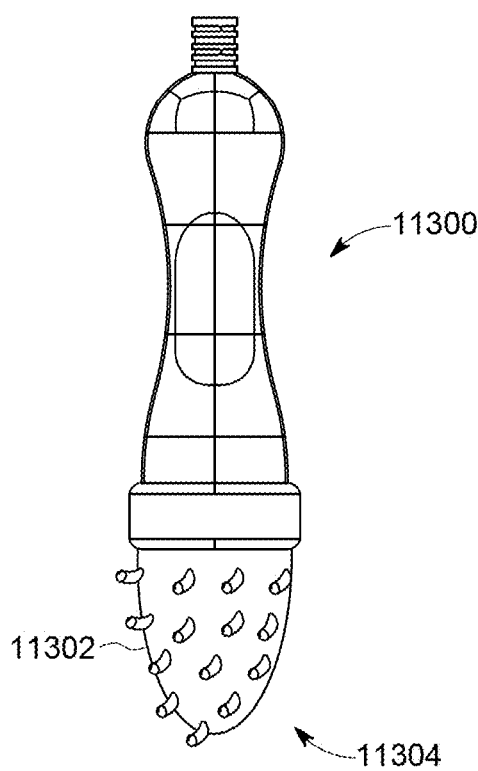
FIGS. 113-116 are illustrations of side views of yet other illustrative fascia tissue treatment devices.

FIGS. 113-116 show various illustrative powered tissue treatment devices that are configured to facilitate treatment of other (e.g., non-planar, etc.) body areas that might be difficult to access with a cylindrical or planar interface. For example, FIG. 113 shows an illustrative powered treatment device 11300 that is configured to facilitate treatment of curved body areas (e.g., near the arm pit, neck, shoulders, joints, etc.). The treatment device 11300 may be the same as or similar to the illustrative fascia tissue treatment devices described with reference to FIGS. 59-75, but include a different treatment assembly (e.g., effector, etc.) design.

As shown in FIG. 113, a treatment assembly 11304 of the treatment device 11300 includes a panel 11302 (e.g., a main body, etc.) and a plurality of finger members engaged with and extending away from the panel 11302. In at least one embodiment, the panel 11302 is shaped as half of an ellipsoid (e.g., an elongated or stretched sphere) having a curved distal end (e.g., outer end) and that tapers between the proximal and distal ends (e.g., so that an outer diameter of the main body reduces continuously between the proximal and distal ends). In some embodiments, a central axis of the panel 11302 is co-linear with a rotational axis of the treatment device 11300 (e.g., a powered treatment head portion of the treatment device 11300).

Figure 114:
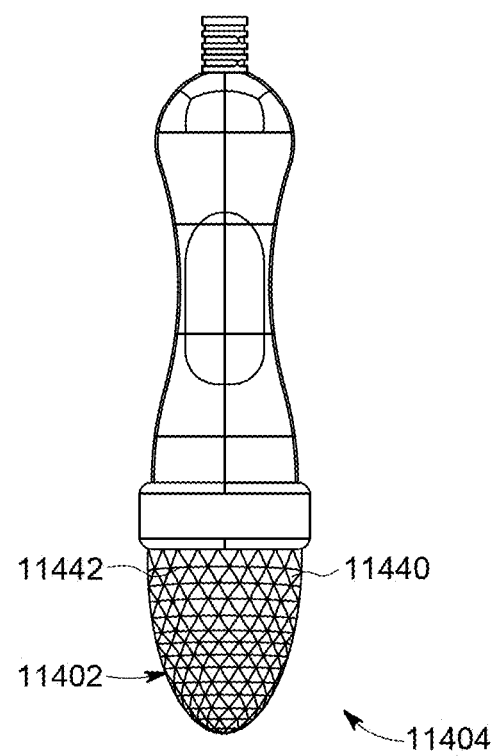

The finger members may be coupled to the panel 11302 and extend away from the panel 11302. The finger members may be curved along (or opposite to) a rotational direction of the treatment assembly 11304. The finger members may be arranged in rows that extend along a circumferential direction around the panel 11302 or positioned in any other suitable arrangement. The shape and/or size of the finger members may also differ in other embodiments. For example, the FIG. 114 shows an embodiment of a tissue treatment assembly 11404 that is shaped as a geodesic polyhedron that includes triangular protrusions 11440 and indentations 11442 along an entire outer surface of the panel 11402. The protrusions 11440 may be continuous along the outer surface, spaced apart at periodic intervals, or positioned in any other suitable arrangement.

Figure 115:
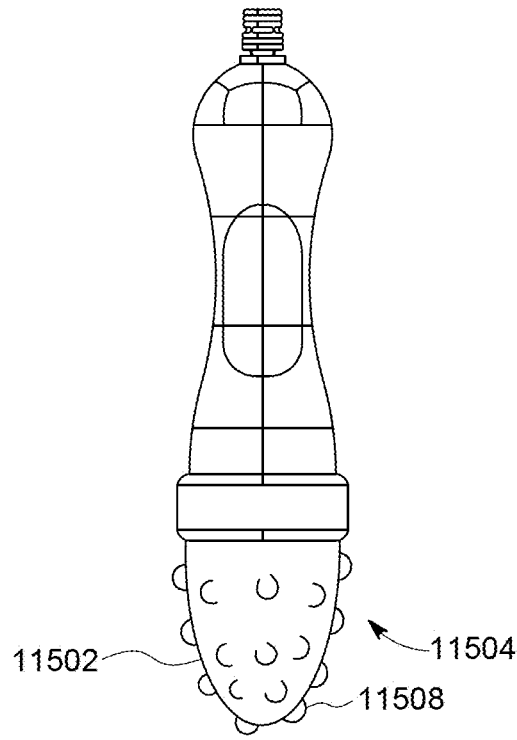

In other embodiments, the finger members may include triangular protrusions 11440 (e.g., tips), rounded protrusions, dimpling, and/or another suitable shape. For example, FIG. 115 shows a tissue treatment assembly 11504 that includes rounded spherical protrusions 11508 that extend away from an outer surface of the panel 11502.

Figure 116:
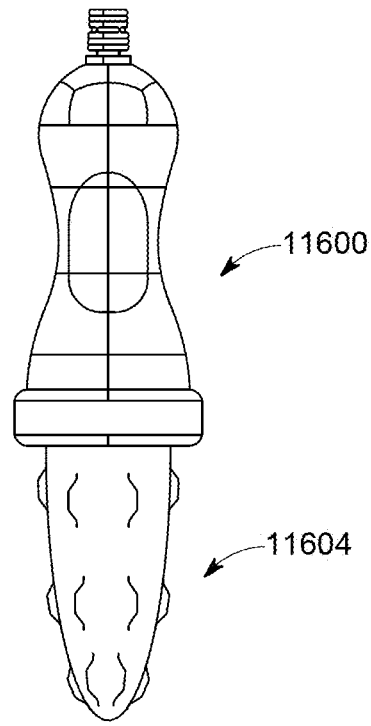

The size and/or shape of the panel may also be different in other embodiments. For example, FIG. 116 shows an illustrative powered tissue treatment device 11600 that includes an elongated tissue treatment assembly 11604 (e.g., an elongated effector, etc.) having a longitudinal length that is approximately equal to a longitudinal length of the treatment head (e.g., housing, etc.). The increased length of the panel can facilitate manipulation of larger curved areas such as behind the knee or within an arm pit. The treatment assembly may also include finger members that are elongated in an axial direction and that form a substantially sinusoidal pattern across the outer surface of the panel (and extending along the axial direction). In other embodiments, the pattern formed by the finger member may be different (e.g., wave crests, sawtooth with rounded tips, etc.).

Figure 117:
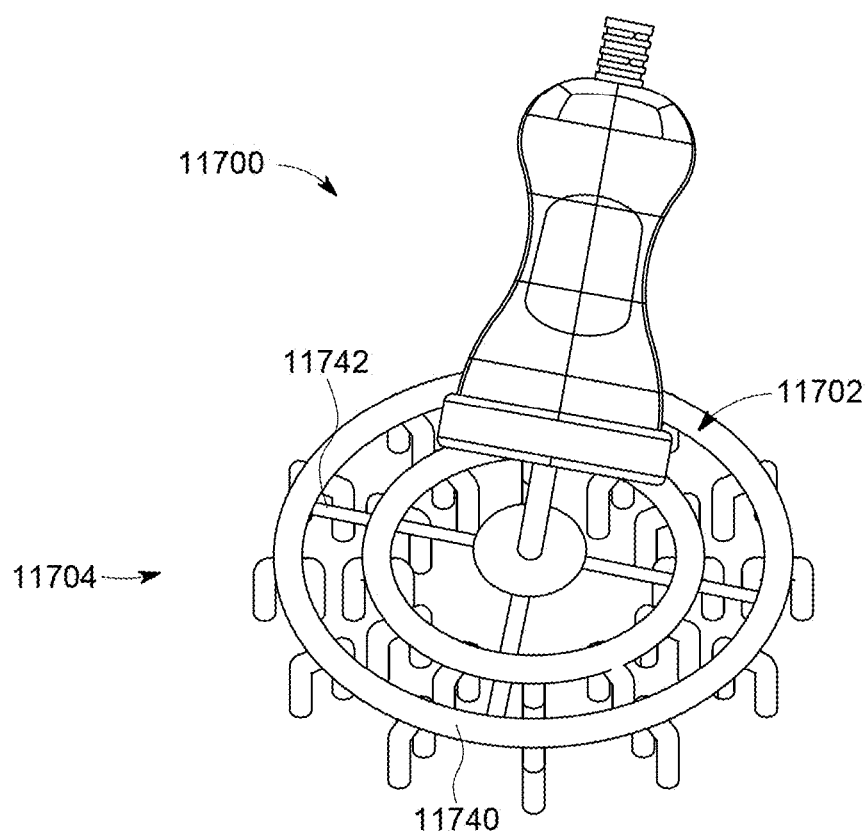
FIG. 117 is an illustration of a top isometric view of yet another illustrative fascia tissue treatment device.
Figure 118:
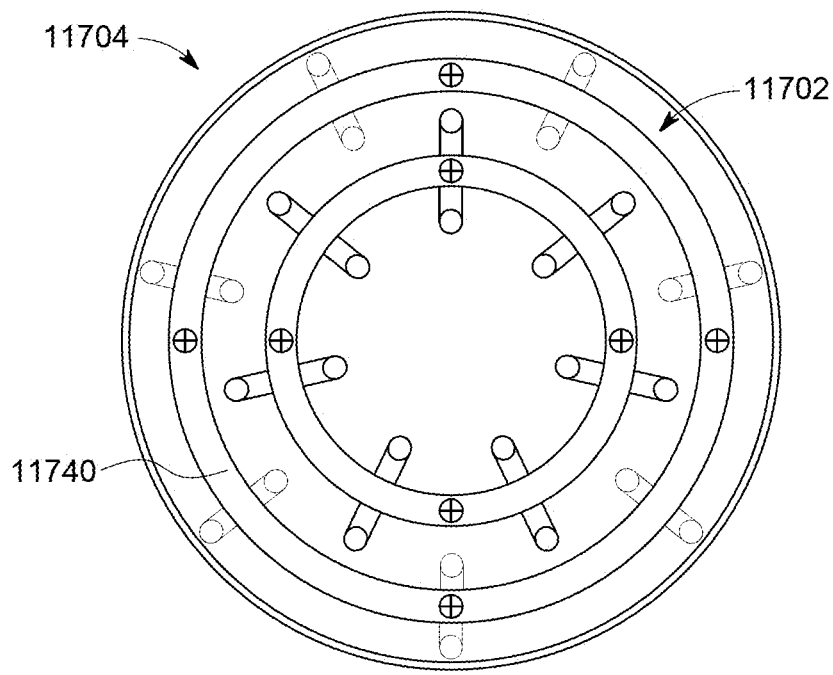
FIG. 118 is an illustration of a bottom view of an effector of the illustrative fascia tissue treatment device of FIG. 117.

FIG. 117 shows yet another illustrative embodiment of a powered fascia tissue treatment device 11700. The treatment device 11700 includes a powered treatment head, which may be the same as or similar to any of the powered treatment heads/devices described herein. The treatment assembly 11704 includes a framework 11702 instead of a panel to support the tissue treatment elements. The framework 11702 has a circular outer shape but may be shaped differently in other embodiments. The framework 11702 may be lighter than a panel, thereby reducing load on a motor of the device used to rotate the framework 11702. The framework 11702 includes a plurality of concentric ring elements 11740 (e.g., ring plates, etc.) that are arranged concentrically about a rotational axis of the powered treatment assembly 11704 (e.g., a central axis of the framework). The framework 11702 may also include a plurality of support elements 11742 (e.g., ribs, radial extensions, etc.) that extend radially (or otherwise) between adjacent ones of the ring elements 11740 and support the ring elements 11740. Although the powered treatment head is shown as being coupled to a central support element (e.g., central panel) of the framework 11702, it should be appreciated that the powered treatment head may be coupled to other parts of the treatment assembly 11704. For example, the powered treatment head may be directly coupled to a concentric ring element 11740 (e.g., the inner most ring, the outer most ring, etc.). Connecting the treatment head directly to the treatment assembly 11704 at a greater radial position along the treatment assembly 11704 can improve structural support and provide torque farther out from the center of the treatment assembly 11704 (thereby reducing stress on the support elements of the treatment assembly 11704). As shown in FIG. 118, the treatment elements may include a plurality of finger members that are engaged with and extend away from the framework 11702. The finger members may be engaged with the concentric ring elements 11740 along both an inner and outer perimeter surface of the ring elements 11740. The finger members may be arranged in opposed pairs that are radially aligned on either side of the ring elements 11740. The finger members may extend at least partially radially away from the ring elements 11740 and also axially away from the framework 11702 (e.g., substantially parallel to a central axis of the framework 11702). The finger members protrude radially beyond and inwardly from the ring elements 11740. In some embodiments, the ring elements 11740 may be removably coupled (e.g., via screws, bolts, or another suitable fastener) to the support elements 11742 so that they can be individually removed and replaced. In other embodiments, at least one of the ring elements 11740, support elements 11742, and treatment elements are integrally formed from a single piece of material.

Figure 120:
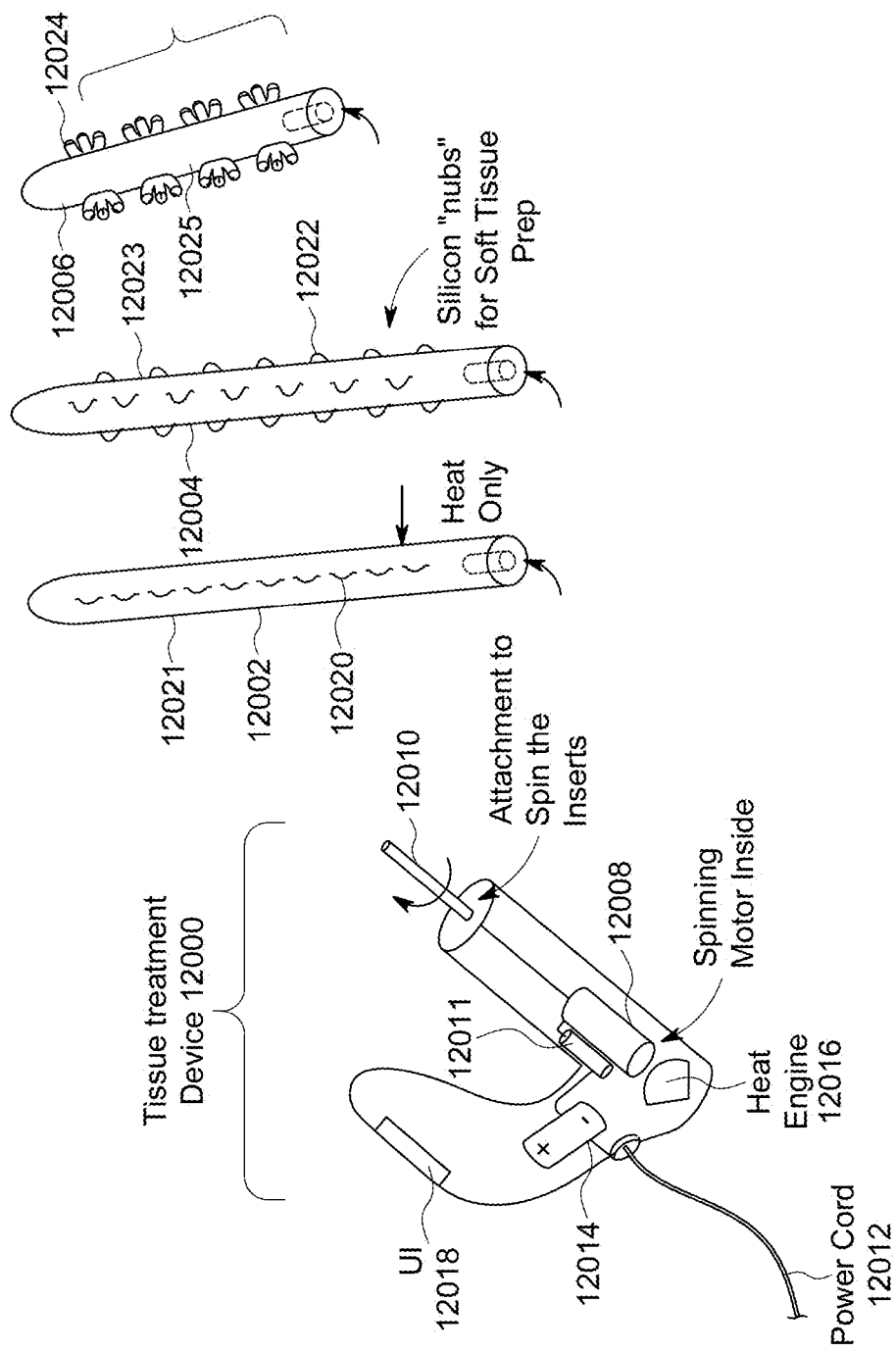
FIG. 120 is an illustration of an inter-vaginal fascia tissue treatment device including various treatment effectors that may be driven thereby for performing fascia tissue treatment within a vagina. In an embodiment, the device 12000 may have an adapter configured to receive an extension handle to enable the user to treat herself while laying down.

FIG. 120 is an illustration of an inter-vaginal fascia tissue treatment device 12000 including various illustrative treatment effectors 12002, 12004, and 12006. The device 12000 may be configured with a motor 12008 configured to rotate a shaft 12010 on which each of the treatment effectors 12002, 12004, and 12006 may be detachably connected for performing inter-vaginal fascia tissue treatment. The motor 12008 may be configured to rotate the shaft 12010 between 1 RPM and 1000 RPM, and a motor controller 12011 may be configured to control the spin of the motor 12008 in a variety of spin profiles (e.g., spline start and finish, linear increase/decrease, parabolic increase/decrease, etc.), such that the patient is safe during treatment. The treatment may include treating fascia tissue that is located along and adjacent to the vaginal walls of a patient. For example, it is possible for women to suffer certain types of injuries or have natural occurrences that distort and/or cause adhesions in the fascia tissue within the vagina region. In other words, fascia tissue in the vagina walls or region accessible via the vagina may become unstructured, thereby causing pain or discomfort during sex or other physical activities. Once such type of injury may occur during child birth as vaginal tears or perineal lacerations may occur. In the event of a tear to the vaginal wall, injury to the transverse perineal muscles (e.g., tear to fascia sheath or muscle), and/or fascia tissue thereat, adhesions or other misalignment of the fascia tissue may occur and scar tissue may be created. For any of these abnormalities, the tissue treatment device 12000 along with the various effectors 12002, 12004, and 12006 may be utilized for treatment.

The tissue treatment device 12000 may be handheld and be powered with a power cord 12012 to charge a battery 12014 that may be used to power the motor 12008. In an embodiment, the device 12000 may include a heat engine 12016 (e.g., electric coils that produce heat from electricity, FAR infrared heating elements that produce infrared signals) that may output heat from the device 12000 that is used to heat vaginal or skin tissue to be treated prior to and/or during treatment. The tissue treatment device 12000 may further include a user interface 12018 that may be a touch screen, push buttons, knobs, switches, and/or any other device that provides an operator or user with the ability to control functional operation of the device 12000 and components therein. For example, to ensure that the vaginal tissue is properly prepared to be treated by the device 12000, vaginal walls and tissue may be heated for a period of time to ensure that the fascia tissue is prepared to be manipulated during treatment. The heating may be performed by an operator (or user of the device 12000) turning on a heating element, such as the heat engine 12016. The user interface 12018 may also include a switch or trigger that controls spin state (e.g., ON state or OFF state) of the motor 12008 along with spin profile of the controller 12011 that controls the motor 12008. During the pretreatment, the motor 12008 may be in an OFF state, thereby allowing for the effector 12002 to be utilized to perform heating without spin.

Alternative to the heating element 12016 being used to heat the vaginal tissue, the effector 12002 that include a heating mechanism, such as a heating coil 12020 that are encased within a wall 12021 or extend through a cavity defined by the wall 12021 of the effector 12002 to cause an external surface of the wall 12021 of the effector 12002 to heat to a particular temperature (e.g., 108 degrees Fahrenheit). To cause the heating coil 12020 to heat, an electrical connection may be made to the heat engine 12016, which may control an amount of electrical current to pass through the heating coil 12020. The electrical connection may be a physical or wireless (e.g., inductor). The wall, which may be formed of a monolithic material, such as stainless steel, silicone, plastic, or combination thereof, may (i) be a single component to avoid seams or other discontinuities to avoid vaginal tissue damage during operation, and (ii) be capable of being sterilized and operate safely in the temperature range (e.g., up to 120 degree Fahrenheit) of the effector. It should be understood that the temperature may be static or the heat engine 12016 may be capable of ramping the temperature up over time (e.g., from 98.6° F. to 110° F.), thereby making the heating treatment easier for the patient. It should be understood that alternative passive (e.g., ceramic) or active (e.g., FAR infrared) heating elements may be configured to be disposed within the effector 12002 so as to apply heat to the patient's vaginal tissue prior to and/or during treatment. It should be understood that heating elements, such as the heating coil 12020, may also be included in the effectors 12004 and 12006 so that heat may be applied during treatment of the vaginal tissue.

The effector 12002 may be have a smooth outer surface of the wall. Effector 12004 may be configured with protrusions or nubs 12022 along the outside wall. The nubs 12022 may be formed of the same material of a wall 12023 of the effector and be U-shaped, sinusoidal shaped, pyramid shaped (with a curved tip), or have a spline shape to avoid having any sharp edges to minimize risk of damage to vaginal tissue yet perform fascia tissue treatment. In an embodiment, the nubs 12022 may be a different material (e.g., silicone) from that of the wall 12023 of the effector 12022. In an embodiment, the nubs 12022 may be integrated with a sheath or condom-like cover that is extended over the wall 12023 of the effector, thereby allowing for an effector to be created and different protrusions to be used in a more cost-effective manner. In an embodiment, the sheath may be a stiff or rigid material (e.g., strong plastic or metal) that is attachable to the effector. In the event of the nubs 12022 being pliable (e.g., soft silicone), the effector 12004 may be used for vaginal tissue preparation.

The length of the nubs 12022 (measured perpendicular to the wall of the effector 12002) may range from a quarter-inch to two-inches depending on the treatment being performed and physical characteristics of the vaginal area of the patient. The diameter of the effector 12002 may range from one-half inch to four-inches. Although shown as a constant diameter along the entirety of the effectors 12002, 12004, and 12006, it should be understood that non-constant diameters and non-linear shaped (e.g., curved with a waist in the middle and bulbous on the distal end from the proximal end that attaches to the shaft 12010) may also be possible. The length of the effectors 12002, 12004, and 12006 may vary in length from 2-inches to 10-inches. Alternative dimensions may also be possible.

The effector 12006 may be configured with tissue treatment elements 12024 connected to or molded with the external surface of a wall 12025 of the effector 12006. The tissue treatment elements 12024 may have the same or similar configurations as the tissue treatment element of FIGS. 108A-108D, as previously described. In an alternative embodiment, the tissue treatment elements 12024 may be in the form of fingers that connect directly to the wall 12025 of the effector 12006. The configuration of the fingers may be similar or the same as those described with regard to FIGS. 113-116. For example, the fingers may be curved along a shaft of the fingers with a concave surface facing a direction of forward rotation of the effector 12006 while the shaft 12010 is spinning. It should be understood that the motor 12008 may be capable of spinning in both directions. In an embodiment, a vibratory element (not shown) may be disposed with the tissue treatment device 12000 such that the effectors 12004 and 12006 may be capable of vibrating or projecting axially forwards and backwards during treatment of the vaginal tissue. Lubrication of the vaginal tissue may be applied prior to and during treatment to avoid injury to the vaginal tissue.

The principles described herein may include, but is not limited to, features and combinations of features described herein and recited in the following paragraphs. It should be understood that the following paragraphs should not be interpreted as limiting the scope of the claims One embodiment may include a powered treatment device for treating fascia tissue including a housing, an actuator coupled to and disposed substantially within the housing, the actuator configured to rotate. A tissue treatment assembly may include a panel detachably coupled to the actuator so as to be rotated with respect to the housing when the actuator is in an ON state, and multiple finger members fixedly coupled to the panel at a proximal end of the respective finger members, the finger members being rigid and extending away from the panel, where each one of the finger members may have a respective central axis extending from the proximal end to a distal end of the respective finger member. At least one of the central axes may extend at least partly along a radial direction and/or a circumferential direction of the panel.

The circumferential direction may be oriented along a direction of travel of the panel when the actuator is in the ON state. A portion of each one of the finger members may extend along the circumferential direction. Each of the central axes may extend along the circumferential direction. At least one of the finger members may include a first portion, a second portion, and a third portion, the first portion extending axially away from the panel, the second portion extending away from the first portion at a first angle, and a third portion extending away from the second portion at a second angle and at least partially axially away from the panel.

At least one of the finger members may include a shaft having a convex surface extending between the proximal end and the distal end of the respective finger member, the at least one finger member defining a tip being monolithic with the shaft and at which the convex surface transitions to a concave surface, the concave surface being oriented with a direction of travel of the panel when the actuator is in an ON state.

At least one of the finger members may include a shaft having a convex surface extending between the proximal end and the distal end of the respective elongated finger member, the convex surface facing axially toward the panel. At least one of the finger members may include a concave surface facing axially away from the panel. The panel may be substantially circular and planar, and wherein the finger members define respective tip portions, the tip portions being substantially co-planar and defining a plane that is spaced apart from the panel and substantially perpendicular to a central axis of the panel. In an embodiment, the finger members are elongated.

The powered treatment device may further include a plurality of force sensors configured to measure force applied to quadrants of the panel, and a controller communicably coupled to the force sensors, the controller configured to determine forces being applied to the quadrants of the panel while the actuator is in the ON state based on sensor data from the force sensors.

A user interface may be communicatively coupled to the controller, and be configured to receive signals from the controller to notify a user of the determined forces. The user interface may include at least one light that is configured to visually indicate a difference in forces between two quadrants of the tissue treatment assembly. The actuator may include a direct drive motor that is coupled to the tissue treatment assembly without an intervening gear set.

The powered treatment device may further include a heating device that is configured to deliver heat toward a side of the tissue treatment assembly when the actuator is in the ON state. The tissue treatment assembly may further include a support member that engages the actuator, wherein the support member is coupled to the panel at a position that is spaced radially apart from a center of the panel. At least one of the finger members may extend along a first circumferential direction relative to a central axis of the panel, the actuator configured to rotate the panel along the first circumferential direction.

A tissue treatment assembly may include a panel, a support member disposed on the panel, where the support member may include a connecting element configured to detachably couple the support member to an actuator. Multiple finger members may be coupled to the panel at a proximal end of the finger members, where the finger members may be rigid and extend away from the panel. Each one of the plurality of finger members may have a respective central axis extending from the proximal end to a distal end of the respective finger member. At least one of the central axes may extend at least partly along a radial direction and/or a circumferential direction of the panel.

The finger members may define respective tip portions, where the tip portions may be substantially co-planar and disposed along a reference plane that is spaced apart from the panel and that is substantially perpendicular to a central axis of the panel. A size of a first one of the tip portions may be different from a size of a second one of the tip portions. The panel may be substantially planar. The finger members may be arranged in approximately equal intervals along a surface of the panel.

At least one of the finger members may extend radially beyond an outer perimeter of the panel. Each of the central axes may extend along the circumferential direction. At least one of the finger members may include a first portion extending axially away from the panel, a second portion extending at an angle relative to the first portion and substantially parallel to the panel, and a third portion extending at least partially axially away from the second portion.

The panel may define an opening at a location of at least one of the finger members. At least one of the finger members may include a shaft having a convex surface extending between the proximal end and the distal end of the respective finger member, the finger member(s) defining a tip being monolithic with the shaft and at which the convex surface transitions to a concave surface, the concave surface being orientated with a circumferential direction of the panel.

The finger members may be arranged in multiple circumferential rows along the panel. Adjacent rows of the finger members may be rotationally offset from one another. The finger members may be arranged in a spiral pattern along the panel. At least one of the finger members may curve back toward the panel so that the respective finger member engages the panel at both the proximal end and the distal end of the respective finger member. At least one of the finger members may include a first edge extending substantially axially away from the panel and a second edge opposite the first edge that curves back toward the panel.

The finger members may form part of a tissue treatment element that is detachably coupled to the panel. The finger members may be integrally formed with the panel as a single monolithic piece. At least one of the finger members may define a frustoconical shape. The support member may be coupled to the panel at a position that is spaced radially apart from a center of the panel. The support member may further include multiple cylindrical support ribs extending at least partially axially away from the panel, the cylindrical support ribs may be concentric with a central axis of the panel. The support member may further include at least one substantially planar rib that extends radially between adjacent ones of the cylindrical support ribs. The support member may further include a skeletal framework that is configured to distribute loading across the panel.

The connecting element may be at least partially disposed at one of: (i) an outer perimeter of the panel, or (ii) an intermediate radial position between a center of the panel and the outer perimeter of the panel. The panel may be curved along a radial direction in a neutral position so that a center of the panel protrudes axially away from an outer perimeter of the panel. The panel may be made from a flexible material, wherein the center of the panel is axially alignable with the outer perimeter of the panel in response to an axial force applied to the center of the panel.

The previous description is of a preferred embodiment for implementing the invention, and the scope of the invention should not necessarily be limited by this description. The scope of the present invention is instead defined by the following claims.

What is claimed is:

1. A powered treatment device for treating fascia tissue, comprising:
   a housing;
   an actuator coupled to and disposed substantially within the housing, the actuator configured to rotate;
   a tissue treatment assembly, including:
      a panel detachably coupled to the actuator so as to be rotated with respect to the housing when the actuator is in an ON state; and
      a plurality of finger members fixedly coupled to the panel at a proximal end of the respective finger members, the finger members being rigid and extending away from the panel, each one of the plurality of finger members having a respective central axis extending from the proximal end to a distal end of the respective finger member away from the panel, the central axes of the finger members extending at least partly along a common circumferential direction of the panel.

2. The powered treatment device according to claim 1, wherein the circumferential direction is oriented along a direction of travel of the panel when the actuator is in the ON state.

3. The powered treatment device according to claim 1, wherein the finger members include:
 a first portion of extending parallel to the panel; and
 a second portion extending from a distal end of the first portion and axially away from the panel.

4. The powered treatment device according to claim 1, wherein at least one of the finger members includes a first portion, a second portion, and a third portion, the first portion extending axially away from the panel, the second portion extending away from the first portion at a first angle, and the third portion extending away from the second portion at a second angle and at least partially axially away from the panel.

5. The powered treatment device according to claim 1, wherein at least one of the finger members includes a shaft having a convex surface extending between the proximal end and the distal end of the respective finger member, the at least one finger member defining a tip being monolithic with the shaft and at which the convex surface transitions to a concave surface.

6. The powered treatment device of claim 5, wherein the concave surface is oriented with a direction of travel of the panel when the actuator is in an ON state.

7. The powered treatment device according to claim 1, wherein at least one of the finger members includes a shaft having a convex surface extending between the proximal end and the distal end of the respective elongated finger member, the convex surface facing axially toward the panel.

8. The powered treatment device according to claim 1, wherein at least one of the finger members includes a concave surface facing axially away from the panel.

9. The powered treatment device according to claim 1, wherein the panel is substantially circular and planar, and wherein the finger members define respective tip portions, the tip portions being substantially co-planar and defining a plane that is spaced apart from the panel and substantially perpendicular to a central axis of the panel.

10. The powered treatment device according to claim 1, wherein the finger members are elongated.

11. The powered treatment device according to claim 1, further comprising:
 a plurality of force sensors configured to measure force applied to quadrants of the panel; and
 a controller communicably coupled to the force sensors, the controller configured to determine forces being applied to the quadrants of the panel while the actuator is in the ON state based on sensor data from the force sensors.

12. The powered treatment device according to claim 11, further comprising a user interface communicatively coupled to the controller, and configured to receive signals from the controller to notify a user of the determined forces.

13. The powered treatment device according to claim 12, wherein the user interface comprises at least one light that is configured to visually indicate a difference in forces between two quadrants of the tissue treatment assembly.

14. The powered treatment device according to claim 1, wherein the actuator includes a direct drive motor that is coupled to the tissue treatment assembly without an intervening gear set.

15. The powered treatment device according to claim 1, further comprising a heating device that is configured to deliver heat toward a side of the tissue treatment assembly when the actuator is in the ON state.

16. The powered treatment device according to claim 1, wherein at least one of the finger members extends along a first circumferential direction relative to a central axis of the panel, the actuator configured to rotate the panel along the first circumferential direction.

17. The powered treatment device of claim 1, wherein a height of the finger members normal to the panel is greater than a dimension of the finger members engaged with the panel.

18. A tissue treatment assembly, comprising:
 a panel;
 a support member disposed on the panel, the support member including a connecting element configured to detachably couple the support member to an actuator; and
 a plurality of finger members coupled to the panel at a proximal end of the respective finger members, the finger members being rigid and extending away from the panel, each one of the plurality of finger members having a respective central axis extending from the proximal end to a distal end of the respective finger member away from the panel, the central axes of the finger members extending at least partly along a common circumferential direction of the panel.

19. The tissue treatment assembly according to claim 18, wherein the finger members define a plurality of tip portions, the tip portions being substantially co-planar and disposed along a reference plane that is spaced apart from the panel and that is substantially perpendicular to a central axis of the panel.

20. The tissue treatment assembly according to claim 18, wherein the panel is substantially planar.

21. The tissue treatment assembly according to claim 18, wherein the finger members are arranged in approximately equal intervals along a surface of the panel.

22. The tissue treatment assembly according to claim 18, wherein at least one of the finger members includes a first portion extending axially away from the panel, a second portion extending at an angle relative to the first portion and substantially parallel to the panel, and a third portion extending at least partially axially away from the second portion.

23. The tissue treatment assembly according to claim 18, wherein the panel defines an opening at a location of at least one of the finger members.

24. The tissue treatment assembly according to claim 18, wherein at least one of the finger members includes a shaft having a convex surface extending between the proximal end and the distal end of the respective finger member, the at least one finger member defining a tip being monolithic with the shaft and at which the convex surface transitions to a concave surface, the concave surface being orientated with the circumferential direction.

25. The tissue treatment assembly according to claim 18, wherein the finger members are arranged in a plurality of circumferential rows along the panel.

26. The tissue treatment assembly according to claim 25, wherein adjacent rows of the finger members are rotationally offset from one another.

27. The tissue treatment assembly according to claim 18, wherein the finger members form part of a tissue treatment element that is detachably coupled to the panel.

28. The tissue treatment assembly according to claim 18, wherein the finger members are integrally formed with the panel as a single monolithic piece.

* * * * *